United States Patent
Ando et al.

(10) Patent No.: US 6,743,352 B2
(45) Date of Patent: Jun. 1, 2004

(54) METHOD AND APPARATUS FOR CORRECTING A GAS SENSOR RESPONSE FOR MOISTURE IN EXHAUST GAS

(75) Inventors: Masashi Ando, Nishikasugai-gun (JP); Noboru Ishida, Kagamigahara (JP); Satoshi Sugaya, Inuyama (JP); Takafumi Oshima, Nagoya (JP); Norihiko Nadanami, Kasugai (JP); Takaki Otsuka, Komaki (JP); Yoshikuni Sato, Nagoya (JP); Tatsuo Okumura, Hashima-gun (JP); Yasuhisa Kuzuya, Ichinomiya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 10/066,684

(22) Filed: Feb. 6, 2002

(65) Prior Publication Data

US 2002/0130053 A1 Sep. 19, 2002

Related U.S. Application Data

(62) Division of application No. 09/045,938, filed on Mar. 23, 1998, now Pat. No. 6,375,828.

(30) Foreign Application Priority Data

Mar. 21, 1997 (JP) ............................................. 9-87361
May 2, 1997 (JP) ............................................ 9-130354
Aug. 6, 1997 (JP) ............................................ 9-224225
Sep. 11, 1997 (JP) ............................................ 9-264972

(51) Int. Cl.$^7$ ........................................... G01N 27/407
(52) U.S. Cl. ................... 205/781; 205/784.5; 73/23.31; 204/425; 204/426
(58) Field of Search ................. 204/425, 426, 204/427; 205/781, 784.5, 785, 788; 73/23.31; 123/693, 694

(56) References Cited

U.S. PATENT DOCUMENTS

| | | | |
|---|---|---|---|
| 4,645,572 A | | 2/1987 | Nishizawa et al. |
| 4,762,605 A | * | 8/1988 | Tanaka et al. ............... 204/406 |
| 4,770,760 A | | 9/1988 | Noda et al. |
| 4,851,103 A | * | 7/1989 | Usami et al. ............... 204/406 |
| 4,902,400 A | | 2/1990 | Usami et al. |
| 4,909,072 A | | 3/1990 | Logothetis et al. |
| 4,927,517 A | | 5/1990 | Mizutani et al. |
| 4,953,390 A | * | 9/1990 | Krempl et al. ................. 73/116 |

(List continued on next page.)

FOREIGN PATENT DOCUMENTS

| | | |
|---|---|---|
| DE | 37 36 259 | 7/1988 |
| DE | 39 24 644 | 1/1991 |
| DE | 43 11 851 | 10/1994 |

(List continued on next page.)

OTHER PUBLICATIONS

"Thick Film ZrO2 NOx Sensor for the Measurement of Low NOx Concentration", SAE Technical Paper Series, 980170, N. Kato, h. Kurachi and Y. Hamada, International Congress and Exposition, Feb. 23–26, 1998.

(List continued on next page.)

*Primary Examiner*—Kaj K. Olsen
(74) *Attorney, Agent, or Firm*—Sughrue Mion, PLLC

(57) ABSTRACT

A method for detecting the concentration of a specific gas (NOx) in an engine exhaust gas using a gas sensor and a process of correcting the gas sensor. According to the correcting process, the amount of moisture in the exhaust gas is estimated, then a a gas concentration detection signal output by the gas sensor on the basis of an estimated amount of moisture is corrected.

Finally, the effect of the amount of moisture in the exhaust gas is removed or reduced from the detected value of gas concentration.

8 Claims, 29 Drawing Sheets

U.S. PATENT DOCUMENTS

| | | |
|---|---|---|
| 5,028,309 A | 7/1991 | Nishizawa et al. |
| 5,034,112 A | 7/1991 | Murase et al. |
| 5,049,254 A | 9/1991 | Logothetis et al. |
| 5,080,765 A | 1/1992 | Wang et al. |
| 5,089,113 A | 2/1992 | Logothetis et al. |
| 5,145,566 A | 9/1992 | Logothetis et al. |
| 5,182,907 A | 2/1993 | Kuroda et al. |
| 5,217,588 A | 6/1993 | Wang et al. |
| 5,250,169 A | 10/1993 | Logothetis et al. |
| 5,288,375 A | 2/1994 | Logothetis et al. |
| 5,304,294 A | 4/1994 | Wang et al. |
| 5,339,627 A | 8/1994 | Baier |
| 5,397,442 A | 3/1995 | Wachsman |
| 5,763,763 A | 6/1998 | Kato et al. |
| 5,780,710 A | 7/1998 | Murase et al. |
| 5,866,799 A | 2/1999 | Kato et al. |
| 5,925,088 A | 7/1999 | Nasu |
| 6,071,393 A | 6/2000 | Oshima et al. |

FOREIGN PATENT DOCUMENTS

| | | |
|---|---|---|
| EP | 0060944 | 9/1982 |
| EP | 0257842 | 3/1988 |
| EP | 0 351 960 | 1/1990 |
| EP | 02 293655 | 4/1990 |
| EP | 0 678740 | 10/1995 |
| EP | 0 719 918 | 7/1996 |
| EP | 0 841562 | 5/1998 |
| GB | 92 035235 | 12/1991 |
| JP | 61-294350 A | 12/1986 |
| JP | 63-38154 | 2/1988 |
| JP | 64-27751 | 1/1989 |
| JP | 64-39545 | 2/1989 |
| JP | 03-070839 | 8/1989 |
| JP | 2-1543 | 1/1990 |
| JP | 2-122255 | 5/1990 |
| JP | 3-73839 | 3/1991 |
| JP | 03-070849 | 3/1991 |
| JP | 3 277961 | 12/1991 |
| JP | 04-116241 A | 4/1992 |
| JP | 5-18059 | 3/1993 |
| JP | 08-029387 A | 2/1996 |
| JP | 08 201 334 | 8/1996 |
| JP | 8-271476 | 10/1996 |
| JP | 09-113484 A | 5/1997 |
| JP | 09-318597 A | 12/1997 |
| JP | 10-073563 A | 3/1998 |
| JP | 10-142194 A | 5/1998 |
| JP | 10-221298 A | 8/1998 |

OTHER PUBLICATIONS

NOx Meter Utilizing $ZrO_2$ Pumping Cell, H. Inagaki, T. Oshima, S. Miyata and N. Kondo, International Congress and Exposition, Feb. 23–26, 1998, pp. 1–6.

960334, Nobuhide Kato, Kunihiko Nakagaki & Noriyuki Ina, Thick Film ZrO2 NOx Sensor, 1996.

970858, Nobuhide Kato, Yasuhiko Hamada & Hiroshi Kurachi, Performance of Thick Film NOx Sensor on Diesel and Gasoline Engines, 1997, pp. 199–206.

S.L. Somov et al., Separation of Electrode Reactions in Multielectrode Amperometric Sensors, Ionics 1 (1995), pp. 514–520.

* cited by examiner

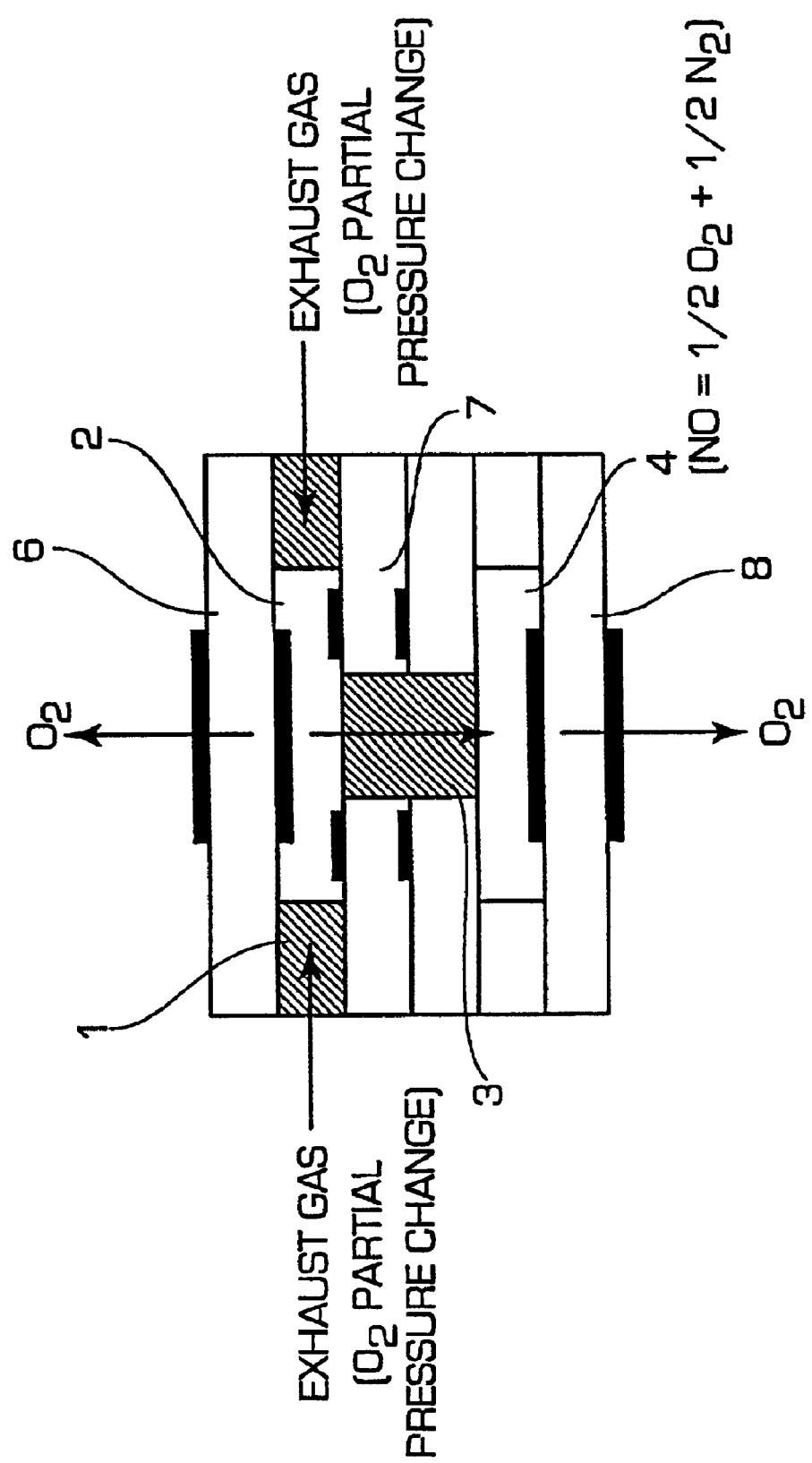

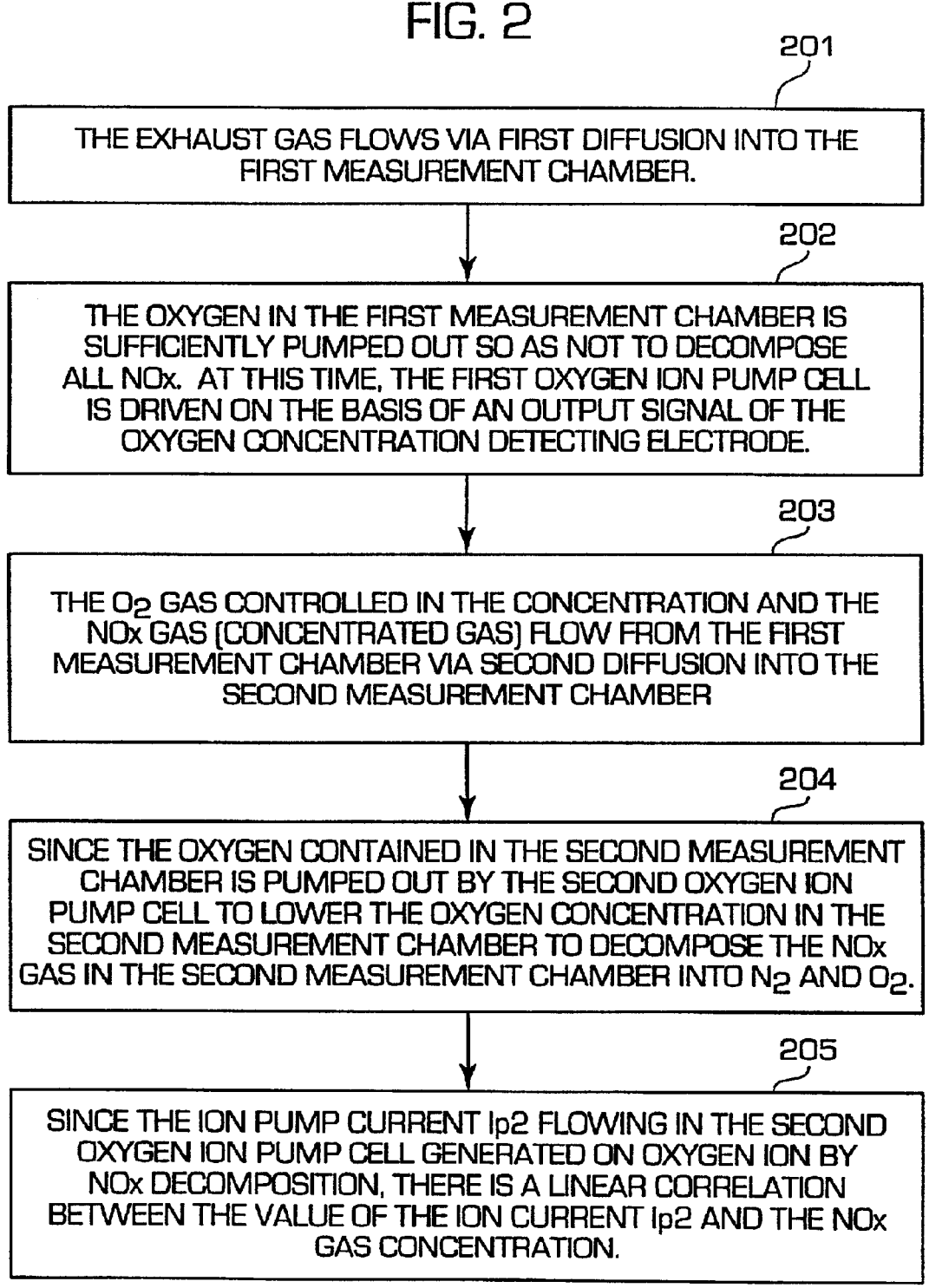

FIG. 3A

IN CASE WHERE OXYGEN CONCENTRATION IN MEASUREMENT GAS IS 0%

GAS CONCENTRATION PROPORTION

| 1ST MEASURING CHAMBER | $N_2$ | $CO_2$ | $H_2O$ | NO |

OXYGEN PUMPING OUT VIA 1ST OXYGEN ION PUMPING CELL →

| 2ND MEASURING CHAMBER | $N_2$ | $CO_2$ | $H_2O$ | NO |

THERE IS NO CHANGE OF GAS CONCENTRATION WHERE PROPORTION IN 2ND MEASURING CHAMBER

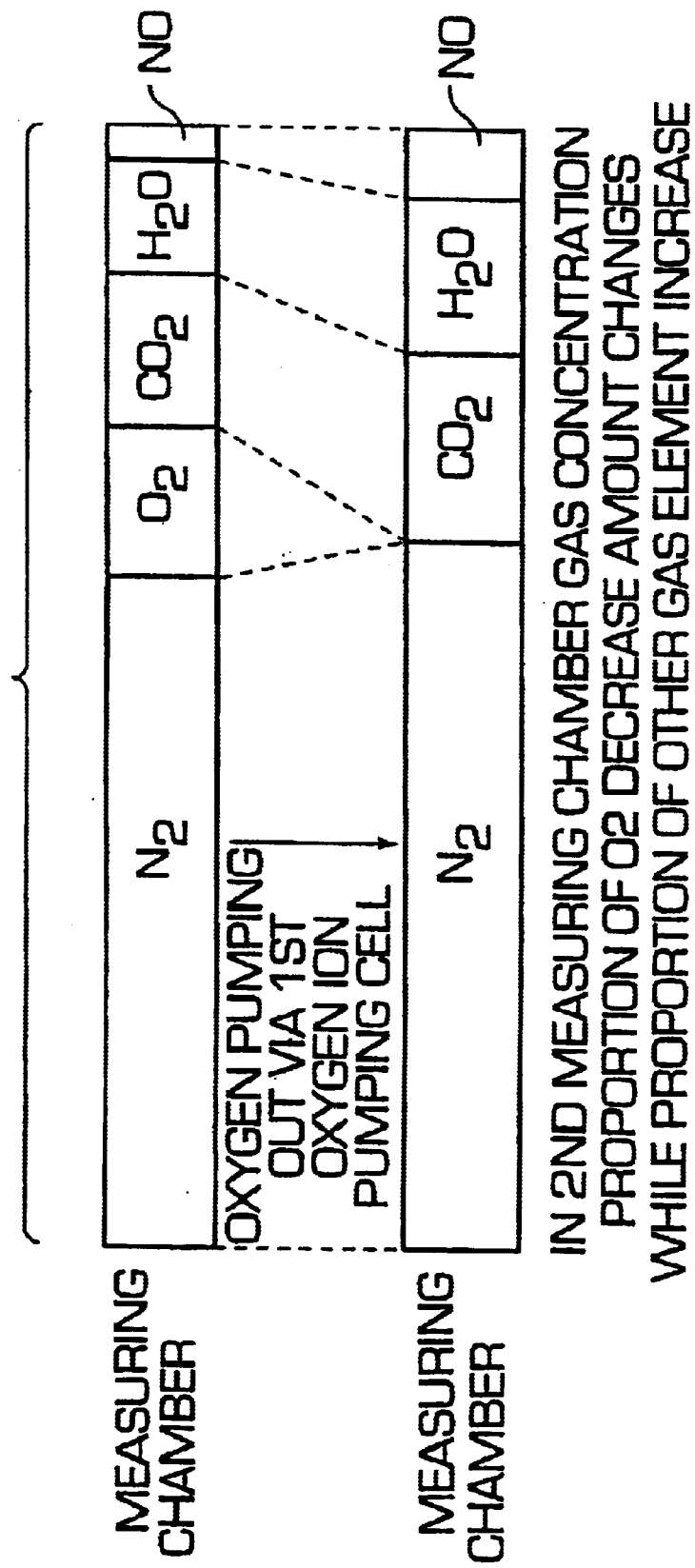

2ND OXYGEN ION PUMPING CURRENT VS. OXYGEN PARTIAL PRESSURE DETECTION CELL POTENTIAL (1500 ppmNO)

RETURNING O2 INTO MEASURING CHAMBER (1) VIA LEAD LINE THROUGH HOLE $O_2$
$NO \rightarrow 1/2\, N_2 + 1/2\, O_2$ $\rightarrow O_2$ PUMPING OUT $O_2$ VIA LEAD LINE

DURABILITY TEST MODE

OFFSET CORRECTION MEANS

OXYGEN AMOUNT AND $H_2O$ CONCENTRATION IN EXHAUST GAS

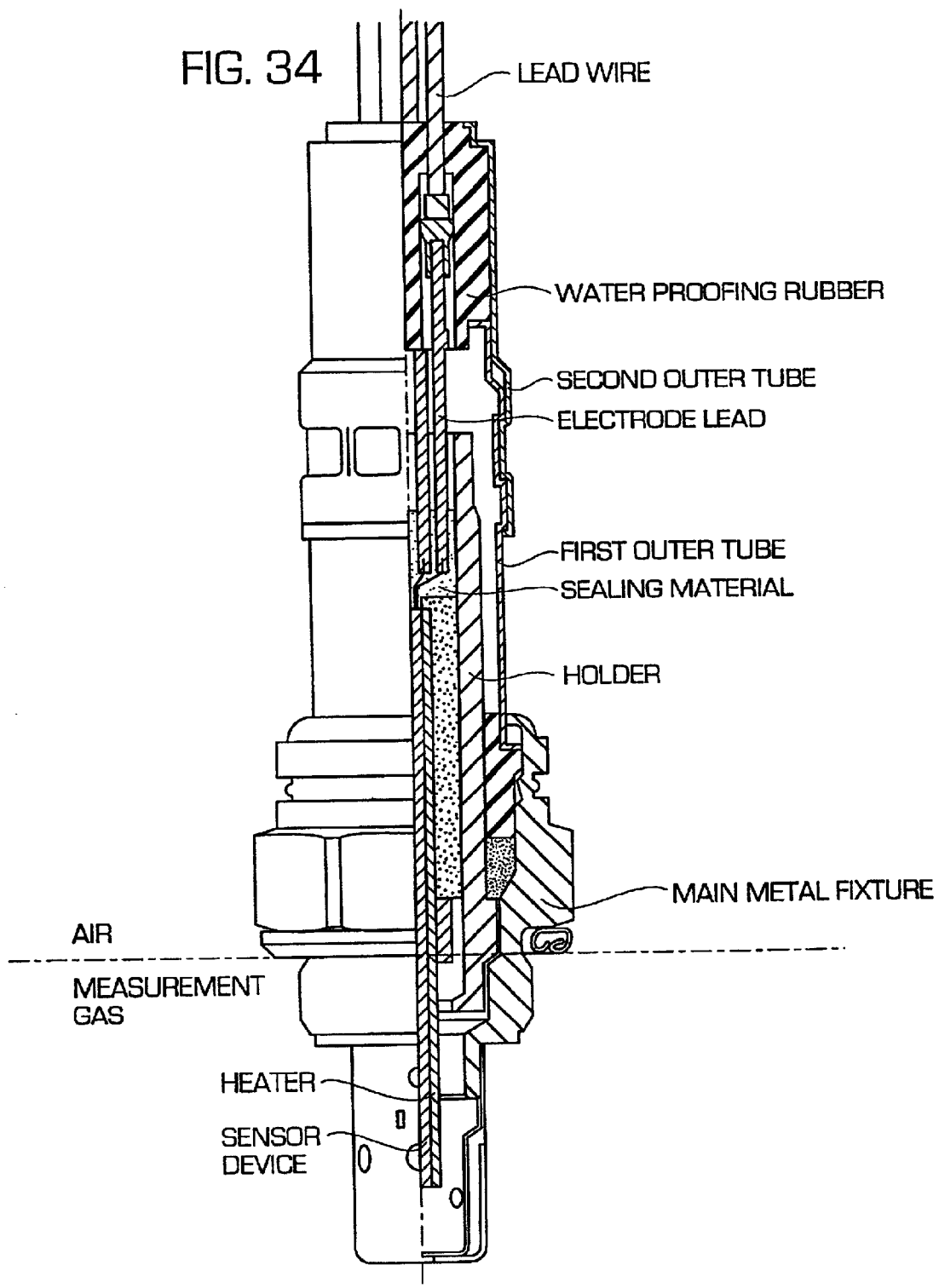

US 6,743,352 B2

METHOD AND APPARATUS FOR CORRECTING A GAS SENSOR RESPONSE FOR MOISTURE IN EXHAUST GAS

This is a divisional of application Ser. No. 09/045,938 filed Mar. 23, 1998, now U.S. Pat. No. 6,375,828; the disclosure of which is incorporated herein by reference.

TECHNICAL FIELD OF THE INVENTION

This invention relates to a gas sensor and, more particularly, to a NOx gas sensor and a method and apparatus therefor, used for detecting the NOx gas concentration in exhaust gases of an internal combustion engine intended for industrial use and for driving an automobile, vessel or aircraft, or in combustion gases of a boiler or the like.

This invention also relates to a method and apparatus for measuring the composition of exhaust gases of a combustion device or an internal combustion engine, in particular the NOx gas concentration This invention also relates to a method and apparatus for controlling a NOx gas sensor used for measuring the NOx gas concentration in an ambient atmosphere in which the oxygen concentration in a measurement gas is changed acutely.

This invention also relates to a method and apparatus for detecting the exhaust gas concentration for measuring the concentration of harmful gas components contained in the exhaust gas from the internal combustion engine and, more particularly, to a method and apparatus for calibrating the zero point of an output of the NOx gas sensor.

RELATED ART

Recently, in dealing with an intensification of exhaust gas regulations, research has been constructed into controlling the operation of an engine or the catalyst based on direct measurement of the NOx in e.g., engine exhaust gases. The resulting NOx gas sensor, which uses an oxygen ion conductor, such as $ZrO_2$, causes the measurement gas (detection gas) to be introduced into a first measurement chamber and a first oxygen ion pumping cell in the first measurement chamber pumps oxygen out, to an extent such as not to decompose NOx at all. Then, the gas lowered in oxygen concentration is introduced into a second measurement chamber where oxygen is further pumped out by a second oxygen ion pumping cell to cause NOx from the NOx-gas contained in the remaining gas to be decomposed. This decomposition is sensed as an electric current. In such NOx gas sensor, the NOx gas concentration is detected based on the current flowing across a pair of electrodes provided in the second oxygen ion pumping cell.

In general, a pair of electrodes are arranged on both sides of the oxygen ion conductor in such sensor. One of the electrodes is exposed to the atmosphere in the first measurement chamber, while the other electrode is exposed to a reference atmosphere containing oxygen. The electrical voltage applied across the first oxygen ion pumping cell is varied, based on an output of an oxygen partial pressure detection cell adapted for measuring the oxygen concentration in the first measurement chamber, in order to control the oxygen concentration in the first measurement chamber to a constant value.

SUMMARY OF THE DISCLOSURE

However, various problems have been encountered in the course of investigations toward the present invention.

First, the output gain of the NOx gas sensor varies depending on the oxygen concentration upon measuring the NOx gas concentration, which results in an error in the NOx gas concentration measurement.

The present inventors have further found that, if the oxygen concentration in the measurement gas is varied significantly, delay is caused in voltage control for the first oxygen ion pumping cell, thereby making it difficult to measure the NOx gas concentration correctly. In particular, in lean burn engines using gasoline or a diesel fuel, which recently are used in increasing numbers, the oxygen concentration in the exhaust gas is varied significantly under the driving condition. Thus, if the PID control is performed based on the potential of an oxygen partial pressure detection cell it is difficult to correctly measure the NOx concentration in the exhaust gas if only the method of varying and controlling the pump capability of the first oxygen ion pumping cell is used.

In the above-described current limiting type sensor, one problem is that the detection current flowing in the oxygen ion pumping cell is as small as several $\mu A$. Moreover, since decomposition of harmful gas components (such as NOx) is controlled or suppressed by the catalytic action on the electrode surface, another problem is that, on prolonged use, catalytic activity is changed causing a shift in the zero point (i.e., a detection output of the gas sensor specifying that the concentration of the pre-set component is substantially zero).

On the other hand, in an oxide semiconductor type gas sensor, which is based on the principle that changes in electrical resistance of an oxide semiconductor is proportional to the amount of a pre-set gas component adsorbed on the oxide semiconductor, suffers from poor reproducibility. Further, if moisture in the measurement gas is electrolyzed, causing it to be decomposed or dissociated, the in the second oxygen ion pumping cell, a current will flow due to oxygen yielded on electrolysis not only of NOx but also of moisture, resulting in an incorrect measurement of the NOx concentration. Moreover, in a lean burn engine using gasoline or a diesel fuel, the moisture in the exhaust gas is varied significantly under driving conditions. Consequently, it is difficult to make a correct measurement of the NOx concentration in the exhaust gases.

Thus, none of these types of gas sensor is reliably used as a sensor for a prolonged time and under significantly varying environmental conditions, as in the case of a sensor mounted on an internal combustion engine, in particular the sensor mounted on an exhaust gas system of a vehicle.

It is therefore an object of the present invention to provide a method and apparatus for accurately measuring NOx gas concentration in engine exhaust.

It is also an object of the present invention to provide a method and apparatus for controlling the NOx gas sensor which enables the NOx gas concentration to be measured accurately even if the oxygen partial pressure in the measurement gas is changed.

It is also an object of the present invention to provide a method and apparatus for measuring an exhaust gas concentration for a prolonged time and, in particular, a method and apparatus which enables calibrating a zero point of the detection output of an NOx gas sensor.

It is a further object of the present invention to provide a method and apparatus for calibrating a gas sensor in which the effect of the amount of moisture in the measurement gas on detection of the gas concentration is reduced or eliminated, in order to enable a correct measurement of gas concentration values.

Still further object of the present invention will become apparent in the entire disclosure.

According to the present invention one or more of the foregoing objects are achieved by several different features of the invention, based on one or more aspects of each feature as disclosed and claimed herein.

According to a first feature of the present invention, there is provided a measurement method and apparatus for measuring the NOx gas concentration in which the NOx gas concentration obtained as a NOx gas sensor output is corrected in response to the oxygen concentration in the detection gas (measurement gas). This is based on a correspondence between the gas sensor output and a current caused to flow by pumping out oxygen dissociated on decomposition of NOx.

An NOx gas sensor according to this first feature includes a first measurement chamber into which a detection gas is introduced via a first diffusion resistance, an oxygen concentration detection electrode for measuring the oxygen concentration in the detection gas in the first measurement chamber, and a first oxygen ion pump cell for pumping oxygen contained in the detection gas out from the first measurement chamber to the outside and/or inside of the first measurement chamber based on the potential of an oxygen concentration detection electrode. The pumping is generally to an extent such that NOx is not entirely decomposed, or in some case to an extent such that nitrogen oxide does not decompose into oxygen in the measurement gas. There also is a second measurement chamber into which the gas is introduced from the first measurement chamber via a second diffusion resistance, and a second oxygen ion pump cell having a pair of electrodes across which a voltage is applied to decompose the oxygen nitride in the second measurement chamber. The dissociated oxygen is pumped out, causing a current corresponding to the nitrogen oxide concentration (second oxygen pump current) to flow in the second oxygen ion pump cell.

According to an aspect of the first feature of the present invention, the NOx gas concentration can be found more correctly by a simple method even if the oxygen concentration in the detection gas does vary. Since the output of the oxygen concentration detection electrode has a specific relation with the oxygen concentration in the detection gas, both the oxygen concentration and the NOx gas concentration can be measured by a single NOx gas sensor, so that the NOx gas concentration, based on the oxygen concentration in the detection gas can be corrected using the sole sensor. Thus, the NOx gas concentration measurement apparatus according to the present invention can be applied to the exhaust system of the internal combustion engine in order to find the air-to-fuel ratio along with the NOx gas concentration, thus allowing a sole instrument to display multiple functions. The coefficient of the second oxygen pump current exhibiting oxygen concentration dependency, used for finding the NOx gas concentration, can easily be calculated preferably using the least square method. Thus, by pre-formulating a table correlating a coefficient with the oxygen concentration, the NOx gas concentration can be obtained correctly in real-time. If this method is applied to the NOx detection system for an internal combustion engine, it becomes possible to construct a highly flexible combustion control systems that can adapt itself to changes in the oxygen concentration and in the NOx gas concentration.

In a second aspect of the first feature of the present invention, the variation (varying amount) of the NOx gas concentration is a function of the variation (varying amount) of the second oxygen pump current. The coefficient of the variation of the second oxygen pump current in this function ('gain') is varied in response to the oxygen concentration in the detection gas in order to find the NOx gas concentration.

In a third aspect, the gain as a coefficient of the variation (varying amount) of the second oxygen pump current is a function of the oxygen concentration in the detection gas. A detection gas having a known oxygen concentration and NOx gas concentration is pre-charged into a sensor to measure the second oxygen pump current. Using values of the NOx gas concentration and the second oxygen pump current, the variation of the second oxygen pump current to the variation of the NOx gas concentration at a predetermined oxygen concentration is found, e.g., by the least square method. Using the gain value at the predetermined oxygen concentration, the coefficient of the oxygen concentration as a function of the oxygen concentration in the detection gas and the gain is found, e.g., by the least square method.

In a fourth aspect the gain is represented as a function of the oxygen concentration in the detection gas. A detection gas having a known oxygen concentration and a known NOx gas concentration is pre-charged to measure the second oxygen pump current. Using the nitrogen oxide concentration and the second oxygen pump current, the variation of the second oxygen pump current to the variation of the NOx gas concentration ("gain at a pre-set oxygen concentration") is found, e.g., by the least square method. The gain at the pre-set oxygen concentration is selected and used depending on the oxygen concentration in the detection gas. *Note variation of NOx gas concentration divided by variation of the second oxygen current is defined as "gain" in this disclosure.

In a fifth aspect the gain is represented in terms of a logarithm function of the oxygen partial pressure in the detection gas. Preferably, a value of the oxygen partial pressure is used as the oxygen concentration in third aspect of the first feature of the invention.

In a sixth aspect, values of the second oxygen pump current for substantially zero NOx gas concentration and for a pre-set NOx concentration, obtained while varying the oxygen concentration in the detection gas, are measured. The gain at the preset oxygen concentration and the second oxygen pump current for the substantially zero NOx gas concentration for the preset oxygen concentration (hereinafter referred to as 'offset at the pre-set oxygen concentration') are measured. From the gain and the offset corresponding to the oxygen concentration in the detection gas and the second oxygen pump current, the NOx gas concentration is found.

In a seventh aspect, the NOx gas concentration obtained based on the second oxygen pump current is corrected based on an output of the oxygen concentration detection electrode that is changed with the oxygen concentration in the detection gas.

In an eighth aspect, the variation (varying amount) of the NOx gas concentration is a function of the variation (varying amount) of the second oxygen pump current. There is provided gain selection means selecting the coefficient of the variation of the second oxygen pump current (hereinafter referred to as 'gain') in this function responsive to the output of the oxygen concentration detection electrode. There is also provided processing means calculating the NOx gas concentration based on the gain selected by the gain selection means based on the second oxygen pump current. The gain selection means can selectively use the coefficient of the gain as determined by, e.g., the least square method and the oxygen concentration in the deletion gas depending on an output of the oxygen concentration detection electrode. Alternatively, a previously found gain at a pre-set oxygen concentration can be selected depending on the output of the oxygen concentration detection electrode. Preferably, the gain selection means and the processing means may be constructed in a micro-computer connected to a nitrogen oxide concentration sensor.

Detection of the oxygen concentration can be based on the output of the oxygen concentration detection electrode means directly or indirectly detecting the oxygen concentration or the current or the voltage representing the oxygen concentration. Preferably, the oxygen concentration is detected based on the potential of the oxygen concentration detection electrode. Alternatively, the oxygen concentration is detected based on a voltage applied across the first oxygen ion pump cell controlled based on the output (potential) of the oxygen concentration detection electrode, and the first oxygen pump current flowing in the first oxygen ion pump cell. Thus, the gain of the nitrogen oxide concentration can be corrected based preferably on the voltage applied across the first oxygen ion pump cell and the first oxygen pump current.

Next, the aspects of the second feature of the present invention is hereinafter briefly explained. The aspects of the second feature is applicable with advantage to the NOx gas sensor to which the aspects of the first feature is applied with advantage. In the aspects of the second feature, the method for measuring the NOx gas concentration is comprised of several elements. That is, in a first aspect if the oxygen partial pressure (concentration) is changed, the detection output of the NOx gas concentration based on the second oxygen ion pump current is corrected in accordance with the change.

In this first aspect of the second feature, the NOx gas concentration can be measured accurately even if the oxygen concentration in the measurement gas would vary acutely. That is, even in an atmosphere in which the oxygen concentration varies significantly, the NOx gas concentration can be found correctly in real-time without control delay. By applying the control method of the aspects of the second feature to the nitrogen oxide detection system for an internal combustion engine, it becomes possible to construct a combustion control system which can adapt itself flexibly to changes in the oxygen concentration and in NOx gas concentration. The control device can be constructed both by software and by hardware.

In a second aspect, there is provided an oxygen partial pressure detection cell having an oxygen partial pressure detection electrode for detecting the oxygen partial pressure in the first measurement chamber. A detection output of the NOx gas concentration is corrected based on an output of the oxygen partial pressure detection cell.

In a third aspect, the voltage applied to the first oxygen ion pumping cell is controlled based on an output of the oxygen partial pressure detection cell. The detection output of the NOx gas concentration is calibrated based on the variation (varying amount) of the current flowing in the first oxygen ion pumping cell (referred to hereinafter as 'first oxygen ion pump current').

In a fourth aspect, the voltage applied across the second oxygen ion pumping cell is controlled responsive to variations in the oxygen partial pressure in the measurement gas.

In a fifth aspect, if the oxygen partial pressure is low, the voltage applied across the second oxygen ion pumping cell is lowered. If the oxygen partial pressure is high, the voltage applied across the second oxygen ion pumping cell is raised.

In a sixth aspect, there is provided an oxygen partial pressure detection cell for detecting the oxygen partial pressure in the first measurement chamber or in the second measurement chamber. If, with the output of the oxygen partial pressure detection cell and the output of the second oxygen ion pumping cell as inputs, the output of the oxygen partial pressure detection cell is changed, a NOx gas concentration detection output based on the second oxygen ion pump current is corrected.

In a seventh aspect, there is provided an oxygen partial pressure controller for controlling the first oxygen ion pump current so that the output of the oxygen partial pressure detection cell will be constant. There is also provided a memory having the pre-stored relation between the variation of the output of the oxygen partial pressure detection cell and the of set of the second oxygen ion pump current. Responsive to the variation in the output of the oxygen partial pressure detection cell, pre-set data is read out from the memory. Based on the read-out data, the value of the offset of the second oxygen ion pump current is varied to correct the NOx gas concentration detection output.

The principles of a third feature of the present invention are identified with respect to the several aspects of this feature of the present invention. Specifically, the method for measuring the NOx gas concentration includes the following points: That is, in a first aspect of the third feature of the present invention, the zero-point of the detection output of the gas sensor, indicating the zero concentration of a specific component, is calibrated based on the detected output of the gas sensor in atmosphere. The concentration of the specific component is detected based on the calibrated detection output.

In this first aspect of the third feature of the present invention, the gas sensor is calibrated under a driving condition, among driving conditions of an internal combustion engine, in which the concentration of the component being detected is known or can be estimated to cancel the shift of the gas sensor detection output after prolonged use for assuring high precision detection of the concentration of the component under detection. The gas sensors capable of measuring the oxygen concentration include a HC sensor and a CO sensor in addition to the NOx sensor. In a sensor capable of measuring the oxygen concentration, it is possible to correct the sensitivity for the oxygen concentration by exploiting the fact that the oxygen concentration is not zero on fuel cutting but an atmospheric gas with an oxygen concentration of 20.9% is introduced. Also, since this calibration can be executed during fuel cutting or during the 'rich' time in the air-to-fuel (A/F) ratio, it is unnecessary to set special operating conditions for executing the calibration. In particular, this calibration method is applied to a NOx gas sensor to enable correct measurement of the NOx gas concentration of the ppm order for prolonged time. Also there is a mode in which, if a NOx sensor for detecting the NOx concentration in the gas discharged from the internal combustion engine is provided downstream of the NOx occlusion type catalyst, the air-to-fuel ratio of a fuel rich region can be set for reducing the occluded NOx. This mode can be exploited to execute the above-mentioned calibration as well as to detect the state of deterioration of the NOx occlusion type catalyst. Further, the state of deterioration of the NOx detection reduction type catalyst arranged in an exhaust duct of the system employing a diesel engine for which the rich air-to-fuel ratio cannot be set, can also be detected.

In a second aspect of the third future of the present invention, the supply of fuel to the internal combustion engine is cut to set the concentration of the specific component in the gas introduced into the gas sensor as to be a level substantially equal to zero or to the atmosphere. Based on the detection output of the gas sensor on cutting the fuel supply, the zero point of the detection output of the gas sensor indicating the zero concentration of the specific component is calibrated.

In a third aspect, the rich air-to-fuel ratio of the internal combustion engine is set in a fuel rich side to reduce the specific component in the exhaust gas and to set the concentration of the specific component to be a level substantially equal to zero or to the atmosphere. The detection output is calibrated base on this level.

In a fourth aspect, the internal combustion engine is driven under a condition in which the concentration of the specific component in the gas discharged from the internal combustion engine can be estimated or is known. The detection output of the gas sensor is calibrated based on the detection output of the gas sensor under this operating condition.

In a fifth aspect, there is provided a gas sensor for detecting the concentration of a component of interest in the gas discharged from the internal combustion engine. There is also provided calibration means for calibrating the detection output of the gas sensor based on the detection output of the gas sensor under the operating conditions as set by driving condition setting means.

In a sixth aspect there is provided a NOx occlusion type catalyst in an exhaust duct of the internal combustion engine. There is also provided driving condition setting means for transiently setting the air-to-fuel ratio to be a fuel-rich side atmosphere for cleaning NOx occluded in the NOx occlusion type catalysts. There is also provided means for detecting the state of deterioration of the NOx occlusion type catalyst based on changes in the detection output of the NOx gas sensor before and after introducing the fuel-rich atmosphere.

In a seventh aspect, there is provided a NOx selective reduction type catalyst arranged in an exhaust duct of an internal combustion engine. There is provided a NOx sensor mounted on a downstream side of the NOx selection reduction type catalyst for detecting the NOx concentration in the exhaust gas. There is also provided means for adding HC to the exhaust gas in the internal combustion engine. There is also provided means for detecting the state of deterioration of the NOx selective reduction type catalyst based on changes in the detection output of the NOx sensor before and after HC addition.

In the exhaust gas concentration detection apparatus in an eighth aspect there is provided a gas sensor for detecting the concentration of a preset component in the gas discharged from the internal combustion engine. There is provided driving condition setting means for setting the driving condition of the internal combustion engine in which the concentration of a component of interest is known or can be estimated. There is also provided calibration means for calibrating the gas sensor detection output based on the gas sensor detection output under pre-set driving conditions.

In a ninth aspect, there is provided a NOx occlusion type catalyst arranged in the exhaust duct of the internal combustion engine. There is also provided a NOx sensor mounted downstream of the NOx occlusion type catalyst in the exhaust duct. There is also provided driving condition setting means for transiently setting the rich air-to-fuel ratio atmosphere for cleaning NOx occluded in the NOx occlusion type catalyst. There is also provided means for detecting the state of deterioration of the NOx occlusion type catalyst based on changes in the NOx sensor detection output before and after setting the rich atmosphere.

In a tenth aspect, there is provided a NOx selective reduction type catalyst in the exhaust duct of the internal combustion engine. There is provided a NOx sensor downstream of the NOx selection reduction type catalyst in the exhaust duct. There is provided means for adding HC into the exhaust gas of the internal combustion engine. There is also provided means for detecting the state of deterioration of the NOx selection reduction type catalyst based on changes in the detection output of the NOx sensor before and after addition of HC According to aspects of a fourth feature of the present invention, there are certain occasions where the moisture provides more than a negligible influence on the sensor output.

In an engine, there is correlation between the excess air ratio or A/F value (=oxygen concentration in the exhaust gases) and the amount of the moisture in the exhaust gases, depending on the fuel used. The present inventors have found that, by pre-measuring the effect a influence of the moisture on the gas concentration detected by the gas sensor, storing the measured effect as a map in a memory as the relation between the excess air ratio or the A/F value, as an example, and correction data of concentration detected by the gas sensor, reading out pre-set correction data from the map during measurement depending on the excess air ratio or A/P value as determined by the driving conditions, and by correcting the detection output signal of the gas sensor based on the readout presumed amount of the moisture, the concentration of specific gas (such as NOx gas concentration) in the exhaust gases can be obtained accurately.

The present inventors have also found that, in the gas sensor of the type employing two sets of oxygen ion pump cells, the oxygen concentration in the exhaust gases can be measured from the electric current value of the first oxygen ion pump cell, and this oxygen concentration has correlation with the amount of moisture in the exhaust gas, so that, by pre-entering a correction coefficient associated with the electric current value flowing in the fast oxygen ion pump cell in a memory, preparing a map correlating the electric current value with the correction coefficient, and by reading out a specific correction coefficient in the map responsive to the electric current value of the first oxygen ion pump cell during gas concentration measurement to correct the electric current value of the second oxygen ion pump cell, correct gas concentration measurement free from the effect of moisture may be realized. The present inventors have also found that the output signal of the first oxygen ion pump cell can be electrically corrected on an analog circuit without having a map on the memory.

According to the several aspects of the fourth feature of the present invention, the gas sensor correcting method and apparatus is based on an estimate of the amount of the moisture in the exhaust gas based on from the engine operating conditions. The gas concentration detection signal outputted by the gas sensor is corrected depending on the estimated amount of the moisture. From the detected value of the gas concentration, the effect of the amount of moisture in the measurement gas is removed or reduced.

In a first aspect of the fourth feature of the present invention, the effect of the amount of the moisture in the detection (measurement) gas on the detection of the gas concentration may be diminished or removed to give an accurate gas concentration value. In measuring the concentration of a specified gas component in the exhaust gas discharged from an internal combustion engine, the amount of the moisture can be estimated from the engine operating conditions. In a gas sensor having two sets of oxygen ion pump cells, the amount of the moisture can be estimated from the electric current values flowing in the first oxygen ion pump current to enable output correction of the gas sensor responsive to the amount of the moisture in the exhaust gas by a relatively simple system. Moreover, by formulating the relation between the amount of the moisture or a value equivalent thereto and the gas sensor output in a map, reference can be made to this map responsive to the signal corresponding to the amount of the moisture or a value equivalent thereto to correct the gas concentration detection signal being output by the gas sensor based on the results of the reference to obtain more accurate gas concentration values.

In a second aspect, the gas sensor is a NOx sensor.

In a third aspect, the gas sensor is a sensor exploiting the oxygen ion pumping operation of the solid electrolyte.

In a fourth aspect, it is assumed that the ratio of the air to the fuel supplied to the engine (air-to-fuel ratio, A/F ratio) corresponds to the amount of the moisture in the exhaust gases. Based on the air-to-fuel ratio, gas concentration detection signal and the true gas concentration value, a map containing correction data of the gas concentration detection signal corresponding to the air-to-fuel ratio is pre-formulated. From this pre-formulated map, pre-set correction data corresponding to the air-to-fuel ratio as determined by the engine operating conditions are read out. The gas concentration detection signal is corrected by the read-out correction data.

In a fifth aspect, a specific or certain voltage is applied across the first oxygen ion pump cell to sufficiently pump oxygen in the measurement gas generally to an extent of not entirely decomposing NOx or in some case to an extent of not decomposing NOx. A current having a parameter corresponding to the oxygen concentration in the measurement gas flows in the first oxygen ion pump current. The second oxygen ion pump cell decomposes NOx in the gas left over in pumping to pump out dissociated oxygen. A current corresponding to the NOx gas concentration flows in the second oxygen ion pump cell. A NOx gas concentration detection signal corresponding to the electric current value obtained from the second oxygen ion pump cell is corrected responsive to a signal corresponding to the electric current value obtained from the first oxygen ion pump cell.

In a sixth aspect, it is assumed that the electric current value of the first oxygen ion pump cell corresponds to the amount of moisture in the measurement gas. Based on the electric current value of the first oxygen ion pump current, electric current value obtained from the second oxygen ion pump cell and the true NOx gas concentration, a map containing correction data of the NOx gas concentration detection signal (corresponding to the electric current value of each first oxygen ion pump cell) is pre-formulated. From this pre-formulated map, specific (preset) correction data corresponding to the electric current value of the first oxygen ion pump current is read out. The NOx gas concentration detection signal is corrected by the read-out correction data.

In a still further aspect, a residual gas is formed under the condition that allows and compensates for substantially decomposition of NO in the first flow channel or generally an upstream region in the flow channel.

This condition is established such that the in-flowing NOx from the ambient gas compensates the decomposed amount of NO to bring an equilibrium state in the residual gas.

The NOx is understood to be substantially the sum of NO and an amount of NO2 in an equilibrium determined generally by the temperature in which the rate of NO2 decreases as the temperature rises. For example, at room temperature it is almost NO2, at 300 to 400° C. 50/50 and at 700° C. or above NO2 is 5% or less.

The sensor is preferably operated at about 700° C. or above and up to about 900° C. more preferably at 750 to 850° C.

Thus the role of NO2 in NOx is relatively small or negligible under the carefully operated conditions, or NO2 may be regarded as NO under certain condition which will be explained later.

BRIEF DESCRIPTION OF THE DRAWINGS

FIG. 1 shows a cross-section along the short side direction of a NOx gas sensor according to an embodiment of the invention.

FIG. 2 is a flowchart for illustrating the principle of detecting the nitrogen oxide concentration by a sensor like shown in FIG. 1.

FIGS. 3A and 3B are conceptual views for illustrating the reason the gain is changed by the oxygen concentration, where FIGS. 3A and 3B illustrate a ratio of the gas components in each chamber with the oxygen concentration in the detection gas of 0% and more than 0%, respectively.

FIGS. 21(a) and 21(b) illustrate an exhaust gas concentration detection apparatus employing a NOx gas sensor according to an embodiment of the present invention wherein FIG. 21(a) illustrates an exhaust gas cleaning system of a gasoline engine (especially a lean-burn engine) and FIG. 21(b) illustrates an exhaust gas concentration detection apparatus applied to an exhaust gas cleaning system of a diesel engine.

FIG. 34 illustrates an example in which a NOx gas sensor according to an embodiment of the various aspects of the present invention is fitted to a metal body.

FIGS. 35A to 35D illustrate a NOx gas concentration sensor having two chamber according to further aspects of the present invention, wherein FIG. 35A is a cross-sectional view for illustrating such NOx gas concentration sensor, FIG. 35B is a longitudinal cross-sectional view thereon FIG. 35C is a schematic enlarged cross-sectional view of the first measurement chamber and FIG. 35D is a plan view of the second measurement chamber.

PREFERRED EMBODIMENTS OF THE INVENTION

Figure 4:
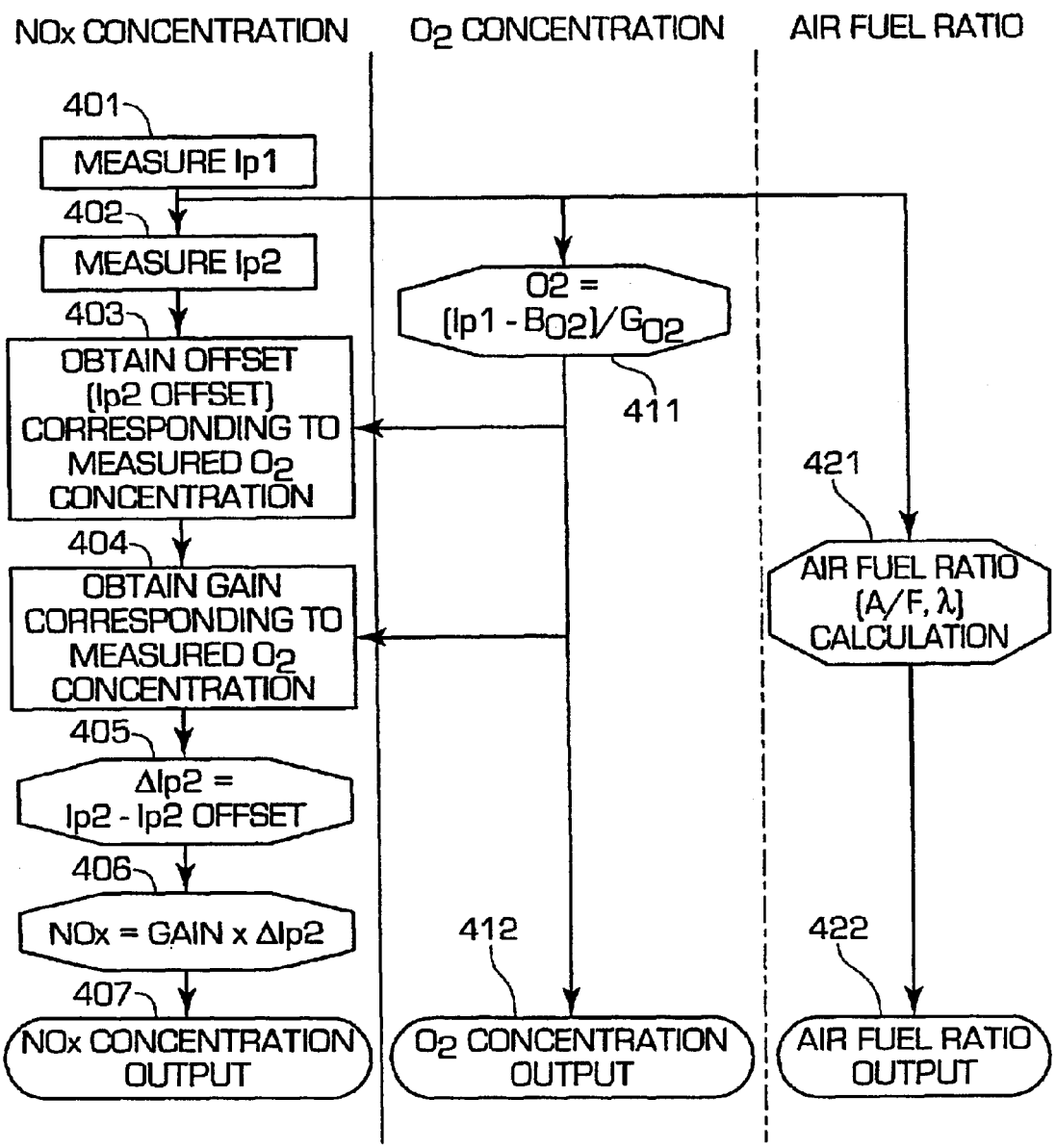
FIG. 4 is a flowchart (or illustrating a method for measuring the NOx gas concentration according to the operation of an embodiment of the present invention and a method for measuring the oxygen concentration and the air-to-fuel ratio.
Figure 5:
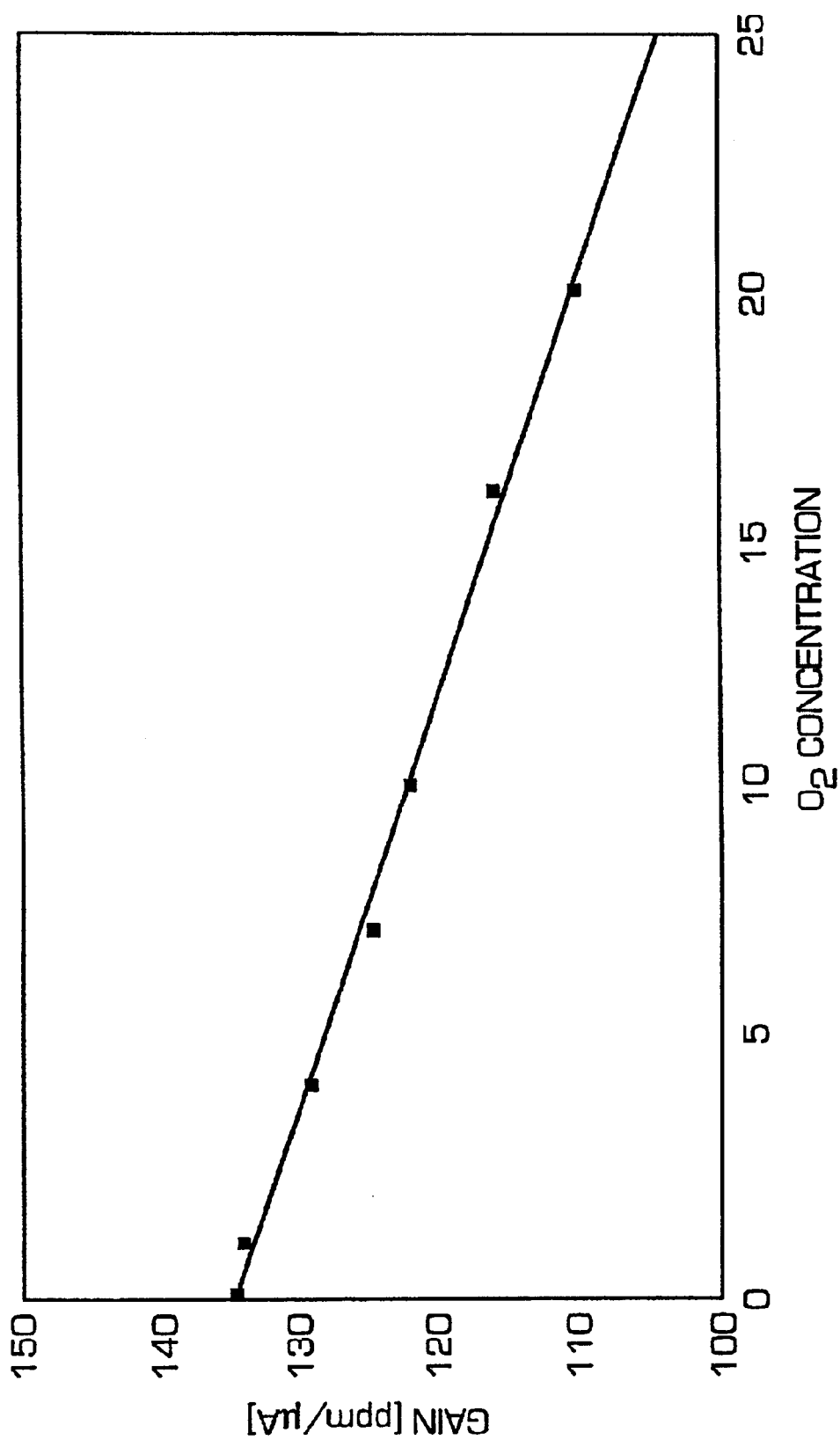
FIG. 5 is a graph that illustrates the dependency of the gain of the NOx gas concentration on the oxygen concentration in the detection gas.

Referring to the drawings, the principle of the first feature of the present invention is explained. The present invention involves a method for calibrating changes in the gain based on the oxygen concentration (or the amount of change of the nitrogen oxide concentration/amount of change of the second oxygen pump current) to measure the NOx gas concentration correctly. The present inventors have already proposed a sensor and a method for detecting the gas concentration, in particular the nitrogen oxide concentration. FIGS. 1 and 2 show the schematic structure of the NOx gas sensor to which the method for measuring the NOx gas concentration according to the present invention is applied, and the process of detecting the NOx gas concentration by this sensor, respectively.

The sensor of FIG. 1 has a first oxygen ion pumping cell 6 including two sets each of diffusion resistance portions, oxygen ion pumping cell and a measurement chamber and a pair of electrodes provided on both sides of a first solid electrolyte layer, an oxygen concentration measurement cell 7 including a pair of oxygen concentration detection electrodes provided on both sides of the second solid electrolyte layer, and a second oxygen ion pumping cell 8 including a pair of electrodes arranged on both sides of the third solid electrolyte layer. An insulating layer is formed between the solid electrolyte layers. Between the first oxygen ion pumping cell 6 and the oxygen concentration measurement cell 7 is formed a first measurement chamber 2 defined by an insulating layer and a solid electrolyte layer. Similarly, by an insulating layer and a solid electrolyte layer, a second measurement chamber 4 is defined above the second oxygen ion pumping cell 8. In a wall surface surrounding the first measurement chamber 2 are formed plural first diffusion holes (portion) 1 having a diffusion resistance. In a midportion of the first measurement chamber 2 is formed a second diffusion hole (portion) 3 in a spaced-apart relation from the first diffusion holes 1. The second diffusion hole 3 is passed through the oxygen concentration measurement cell 7 and the solid electrolyte layer to provide communication between the first and second measurement chambers 2 and 4 with a diffusion resistance.

In the sensor shown in FIG. 1, the process of detecting the NOx gas concentration in the exhaust gas is as shown in FIG. 2, steps 201 to 205. Thus, the NOx gas concentration can be found by exploiting the fact that the second oxygen pump current IP2 is proportionate to the amount of oxygen yielded on decomposition of NOx. Meanwhile, the first diffusion resistance and the second diffusion resistance correspond in FIG. 1 to a gas diffusion resistance possessed by the first diffusion holes 1 and the second diffusion hole 3, respectively.

As a practical matter, in a low oxygen concentration atmosphere lower than a specific value, oxygen cannot be pumped out completely from the first measurement chamber due to constraint such as NOx decomposition. Therefore, the oxygen pumped out from the second measurement chamber is both oxygen yielded on NOx decomposition in the second measurement chamber and oxygen not pumped in the first measurement chamber and diffused into the second measurement chamber. That is, the current flowing in the second oxygen ion pumping cell is affected by both the residual oxygen concentration in the second measurement chamber and the NOx gas concentrations Therefore, the effect of residual oxygen needs to be precluded for enabling correct measurement of the NOx gas concentration. Thus, it may be contemplated to use different values of 'offset' depending on the oxygen concentration.

Specifically, (i) for various values of oxygen concentration, the nitrogen oxide concentration is set to zero, and the amount of the current flowing at this time through the second oxygen ion pumping cell (this amount of current being hereinafter referred to as 'offset') is measured, and (ii) the current flowing at this time through the second oxygen ion pumping cell is measured using a detection gas having a known standard NOx gas concentration. The 'gain' of the variation of the second oxygen ion pumping cell current is thus determined throughout the various values of oxygen concentration. This gain is given by the following equation:

'Gain'=(standard NOx gas concentration)/(generated current amount–offset)

The values of the offset, thus found, varied with the oxygen concentration, and a perpetually constant gain value, are pre-stored in storage means, such as memory. During measurement, the offset values and the gain as well as the current flowing in the second oxygen ion pumping cell are entered to a micro-computer to calculate the NOx gas concentration. Since the offset is varied with the oxygen concentration, as described above, pre-set values that correlate with the oxygen concentration values are pre-stored as a map. Depending on the output of the oxygen concentration measurement cell, preset data (offset values) are read out from this map to correct or calculate the NOx gas concentration However, the present inventors have found, as a result of this investigations, that gain calibration according to oxygen concentration is required for correct measurement of the NOx gas concentrations occurring on the order of several ppm. The reason the gain is varied by the oxygen concentration is possibly as follows. FIGS. 3(A) and 3(B), conceptually show one reason why the gain is changed by the oxygen concentration, and also show the change in the proportions of the gas concentration between the first and second measurement chambers. In the sensor shown in FIG. A1, oxygen is pumped by the first oxygen ion pumping cell from the first measurement chamber so that the concentration of oxygen flowing from the first measurement chamber into the second measurement chamber will be equal to the concentration prescribed in the oxygen concentration measurement cell (constant electromotive force). The following proportions prevail as the proportions of the oxygen concentration of respective components (NO, CO and the like) flowing into the second measurement chamber.

Figure 6:
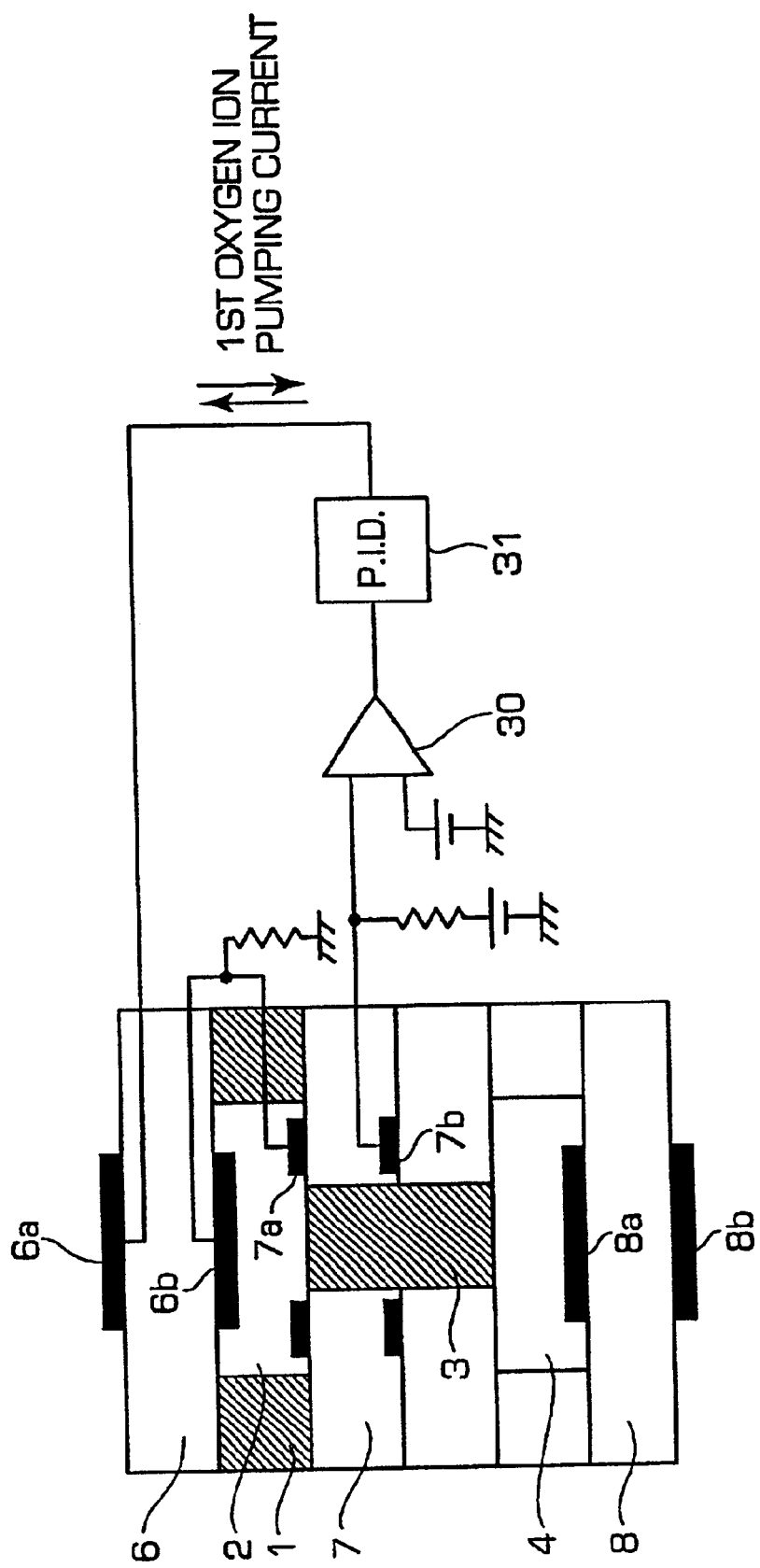
FIG. 6 illustrates a NOx gas sensor control device according to a comparative example.
Figure 26:
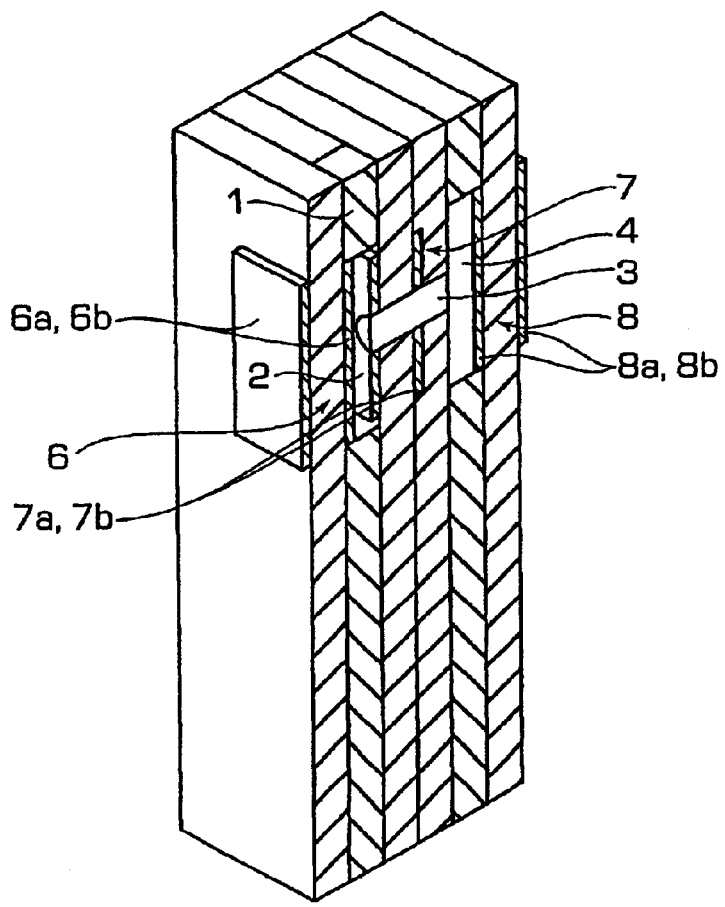
FIG. 26 is a perspective view showing a cross-section in a longitudinal direction of the NOx gas sensor shown in FIG. 1.

Referring to FIG. 3A, if the oxygen concentration in the measurement gas is zero, there is no oxygen pumped out by the first oxygen ion pumping cell, so that the proportions of the gas concentration of various components flowing into the second measurement chamber are not changed. However, referring to FIG. 3B, the amount of oxygen pumped out by the first oxygen ion pumping cell is increased with increased oxygen concentration in the gas being detected. As a result, the proportions of the various gas components flowing into the second measurement chamber are increased corresponding to the decreased amount of oxygen as compared to that of the detection gas. That is, the higher the oxygen concentration in the detection gas, the higher becomes the NOx gas concentration in the second measurement chamber. Thus, the amount of the current in the second oxygen ion pumping cell proportionate to the amount of oxygen yielded on NOx decomposition is increased to increase the sensor sensitivity to the NOx gas concentration (the gain is lowered). For more correct calculation of the NOx gas concentration, the gain lowering caused by the increased sensor sensitivity cannot be disregarded to render it necessary to make corrections. The present inventors provide means for correcting the gain in response to the oxygen concentration in the detection gas based on the foregoing information. Referring to FIGS. 2, 6 and 26, the principle pertaining to the second feature of the present invention and the invention underlying this principle are explained. FIG. 6 is a transverse cross-sectional view for illustrating the schematic structure of a NOx gas sensor to which the control method according to the second feature of the present invention is advantageously applies. The transverse cross-section of FIG. 6 corresponds to a cross-section of the sensor shown as a longitudinal cross-section in FIG. 26. The sensor of FIG. 6 has a first oxygen ion pumping cell 6, including two sets each of diffusion resistance portions, an oxygen ion pumping cell and a measurement chamber and a pair of electrodes 6a, 6b provided on both sides of a first solid electrolyte layer. An oxygen concentration (partial pressure) measurement cell 7 including a pair of oxygen concentration detection electrodes 7a, 7b provided on both sides of the second solid electrolyte layer, and a second oxygen ion pumping cell 8 including a pair of electrodes 8a, 8b arranged on both sides of the third solid electrolyte layer, also are used. These layers are laminated in order and an insulating layer is formed between the solid electrolyte layers. Between the first oxygen ion pumping cell 6 and the oxygen concentration measurement cell 7 is formed a first measurement chamber 2 by an insulating layer and the solid electrolyte layers. Similarly, by an insulating layer and the solid electrolyte layers, a second measurement chamber 4 is defined above the second oxygen ion pumping cell 8. In a wall surface surrounding the first measurement chamber 2 are formed plural first diffusion holes 1 having a diffusion resistance. In a mid portion of the first measurement chamber 2 is formed a second diffusion hole 3 in a spaced-apart relation from the first diffusion holes 1. The second diffusion hole 3 is passed through the oxygen concentration measurement cell 7 and the solid electrolyte layers to provide communication between the first and second measurement chambers 2 and 4 with a diffusion resistance.

Actually, in a low oxygen concentration atmosphere lower than certain specific value, oxygen cannot be pumped out completely in the first measurement chamber due to a constraint of NOx decomposition. Therefore, the oxygen pumped out from the second measurement chamber is made up of both an oxygen portion yielded on NOx decomposition in the second measurement chamber and an oxygen portion that was not pumped out of the first measurement chamber and was diffused into the second measurement chamber. That is, the current flowing in the second oxygen ion pumping cell is affected by both the residual oxygen concentration in the second measurement chamber and the NOx gas concentration. Therefore, the effect of residual oxygen needs to be precluded for enabling correct measurement of the NOx gas concentration.

Thus according to the invention which forms the basis with respect to the second feature of the present invention, the effect of oxygen is precluded in the following manner. That is, (i) measurement gases in which the nitrogen oxide concentration is previously set to 0 and the oxygen concentration has various different values (gases with various value of the oxygen concentration) are charged into a measurement unit and measurement is made on the current flowing in the second oxygen ion pumping cell (this current is hereinafter referred to as 'offset'); (ii) the measurement gas with the standard NOx gas concentration is charged into a measurement device and measurement is made on the current flowing in the second oxygen ion pumping cell; and (iii) from these measured values, the 'gain' of the variation of the second oxygen ion pump current is set. This gain is given by the following equation:

'Gain'=(standard NOx gas concentration)/(generated current amount−offset)

The value of the offset, thus found, varied with the oxygen concentration, and the gain values, are pre-stored in storage means, such as memory. During measurement, the offset and the gain as well as the current flowing in the second oxygen ion pumping cell are entered to a micro-computer to calculate the NOx gas concentration.

However, it has turned out there is a problem as follows. Namely, if the oxygen concentration in the measurement gas varies, the oxygen concentration in the first measurement chamber is not constant due to, for example, control delay, even if it is attempted to pump out oxygen by the first oxygen ion pumping cell to provide a constant oxygen concentration in the first measurement chamber using a control method such as PID. Thus, there may be an occurrence that the oxygen concentration in the first measurement chamber is lowered excessively, such that NOx is decomposed in the first measurement chamber and an output is decreased when measuring NOx in the second measurement chamber, or that the oxygen concentration is raised. In such case, excess oxygen which should inherently be pumped out in the first measurement chamber is also measured, with a result that an output is increased to render it possible to measure the NOx quantity accurately.

The control method and apparatus according to the second feature of the present invention is explained by contrasting it to the control method and apparatus according to the comparative example. First, the control method and apparatus according to a comparative example is explained with reference to FIGS. 6 and 7. The structure of component parts shown in FIG. 6 is similar to that shown in FIG. 1. In FIG. 6, a reference electrode 7b of the oxygen concentration measurement cell 7 is electrically connected to an input terminal of a differential amplifier 30 to enter the output voltage of the oxygen concentration measurement cell 7. To an output terminal of the differential amplifier 30 is connected an input terminal of a controller 31. The controller 31 performs PID control based on the offset of the voltage of the reference power source from the electromotive force of the oxygen concentration measurement cell 7 to control the voltage applied across a pair of electrodes 6a, 6b of the first oxygen ion pumping cell 6 so that the electromotive force of the oxygen concentration measurement cell 7 will be equal to the voltage of the reference power source.

Figure 7:
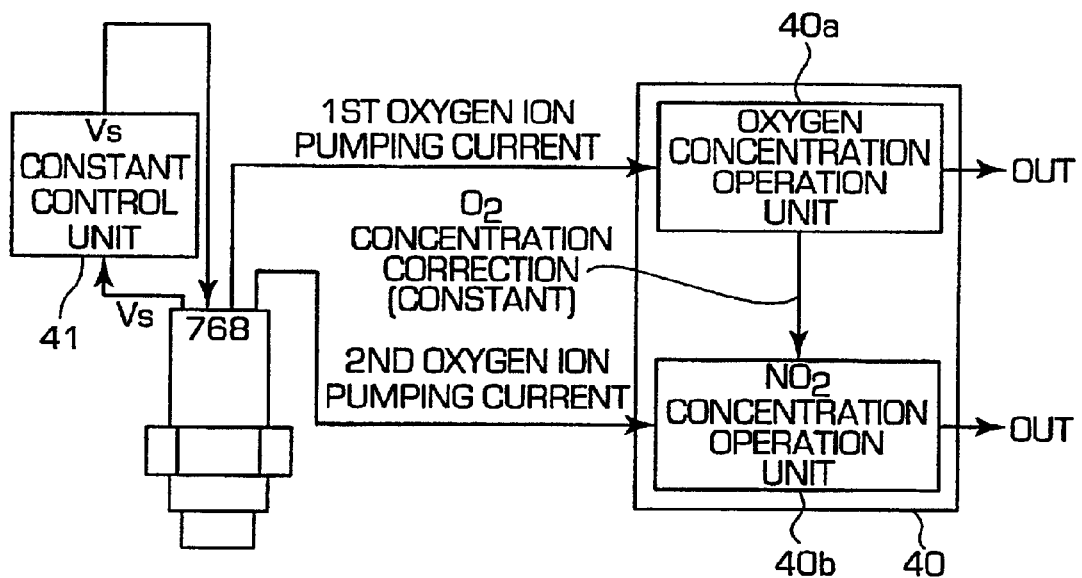
FIG. 7 is a block diagram for illustrating a NOx gas concentration measurement device according to a comparative example.

The control apparatus according to the comparative example shown in FIG. 7 has a constant-Vs-controller 41 equivalent to the differential amplifier 30 and the controller 31 shown in FIG. 6, and a controller 40 having first and second oxygen ion pump currents as inputs and the oxygen concentration and NOx concentration values as outputs. The constant-Vs-controller 41 has the output of the oxygen concentration measurement cell 7 as input and controls the voltage applied across the first oxygen ion pumping cell 6 to render the electromotive force of the oxygen concentration measurement cell 7 constant. The controller 40 has, as inputs, the first oxygen ion pump current flowing in the first oxygen ion pumping cell 6 and the second oxygen ion pump current flowing in the second oxygen ion pumping cell 8. An oxygen concentration calculation unit 40a of the controller 40 finds the oxygen concentration based on the first oxygen ion pump current and outputs the resulting oxygen concentration while outputting an oxygen concentration correction signal. A NOx concentration calculation unit 40b of the controller 40 has, as input the oxygen concentration calibration signal and the second oxygen ion pump current, and outputs a nitrogen oxide concentration value corrected for oxygen concentration based on the input signals. That is, the system shown in FIG. 7 presupposes the constant oxygen partial pressure (concentration) steady state and executes the oxygen concentration correction for detecting the NOx gas concentration based on the first oxygen ion pump current.

Figure 8:
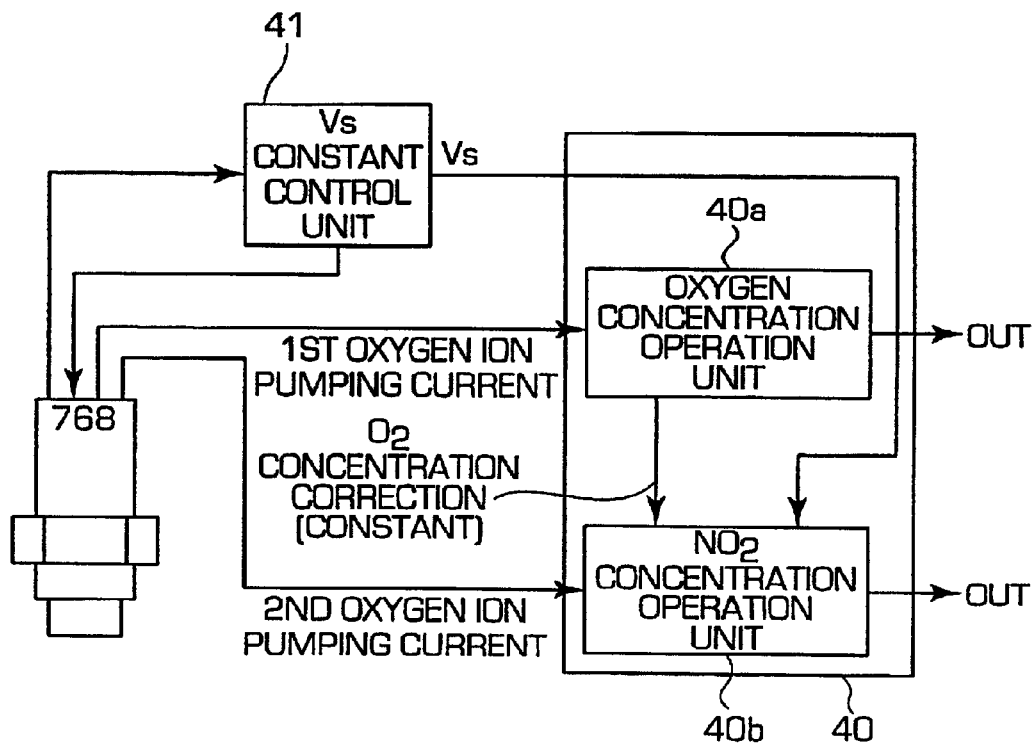
FIG. 8 is a block diagram for illustrating a NOx gas concentration measurement apparatus according to an embodiment of the present invention.

On the other hand, in the control device for the NOx gas sensor according to the second feature of the present invention, shown in FIG. 8, an oxygen concentration detection output (oxygen concentration detection voltage) of the constant-Vs-controller 41 is directly entered to the NOx concentration calculation unit 40b, which then corrects the nitrogen oxide concentration for oxygen concentration based further on the rate of change (variation) of the detection output of the oxygen concentration (detected voltage of the oxygen concentration) in addition to the above-mentioned oxygen concentration correction signal and the second oxygen ion pump current. It is possible with this control device to correct the detection output of the NOx gas concentration responsive to the rate of change (variation) of the oxygen concentration even if the oxygen concentration in the measurement gas is fluctuated significantly (in a non-steady state of the oxygen partial pressure), to preclude to effect of fluctuations of the oxygen concentration for accurately detecting the NOx gas concentration.

The method for calibrating the detection output of the gas sensor based on the aspects of the third feature of the present invention is characterized in that the gas sensor is calibrated based on a detection output of the gas sensor under one of the driving conditions for the internal combustion engine which permits estimation of the concentration of the harmful exhaust gas components. In general, in an internal combustion engine of a vehicle having an electronically controlled fuel supply device, the fuel supply is cut when an output is not needed, as during deceleration. Thus, the concentration of the harmful gas components, such as NOx, HC or CO, is approximately of the same level as that in atmosphere. Conversely, the concentration of the harmful gas components discharged from the internal combustion engine under the normal operating conditions is significantly higher than that in atmosphere. Thus, by calibrating the gas sensor during fuel cutting, the concentration of the harmful exhaust gas can be detected correctly even after prolonged use. Moreover, since it is the zero point of the detection output (offset) that is changed by prolonged use of the gas sensor, it is important to correct this zero point. For this purpose, the following would be pertinent. That is, the detection output upon fuel cutting is set to, for example, a level indicating the zero NOx gas concentration level.

If the offset value of the detection output of the gas sensor (detection output in case of the zero concentration of the detected component, or the zero-point detection output) exhibits oxygen concentration dependency, that is if the offset value is changed with the oxygen concentration, the following is pertinent. Namely, assume all offsets (for each value of the oxygen concentration) are corrected based on the value of the detection output at the time of fuel cutting for the known oxygen concentration and the concentration of the component to be detected. For example, assumed the difference between the initial value of an offset corresponding to a pre-set oxygen concentration stored in the memory (OF1) and a detected output corresponding to the pre-set oxygen concentration at the time of fuel cutting (OF2), i.e., "OF1−OF2", is subtracted from an offset value OF[O2] for various values of the oxygen concentration stored in the memory, and the resulting value is stored in the memory as a now offset value OF[O2]. In the case of a sensor capable of measuring the oxygen concentration, the gas of the oxygen concentration substantially equal to that in atmosphere, that is the gas with the oxygen concentration of 20.9%, is supplied to the gas sensor to permit calibration of the sensitivity (1/gain). For example, by applying the method according to the present aspect to a NOx sensor as later explained, the sensitivity of the first oxygen pump current can be calibrated to permit correct measurement of the oxygen concentration after prolonged use.

If the gas sensor is a NOx gas sensor, which is arranged downstream of the NOx occlusion catalyst, a spike of a rich atmosphere is introduced for reducing the occluded NOx. Since there is substantially no NOx emission at this timing, the zero point can be calibrated in the same way as described above. Moreover, comparison of detection outputs of the NOx sensor before and after insertion of the rich-atmosphere spike permits detection of the catalyst deterioration (lowering of the NOx occlusion amount) without necessity of taking offset changes into account.

Figure 23:
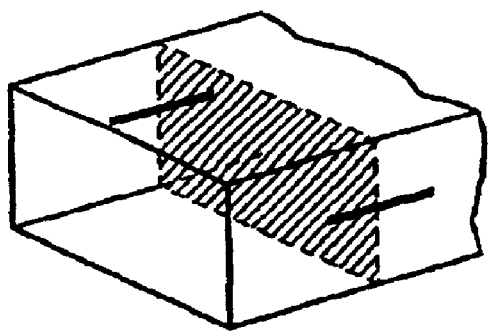
FIG. 23 is a perspective view of the sensor for illustrating the position of the cross-section shown in FIG. 1.
Figure 24:
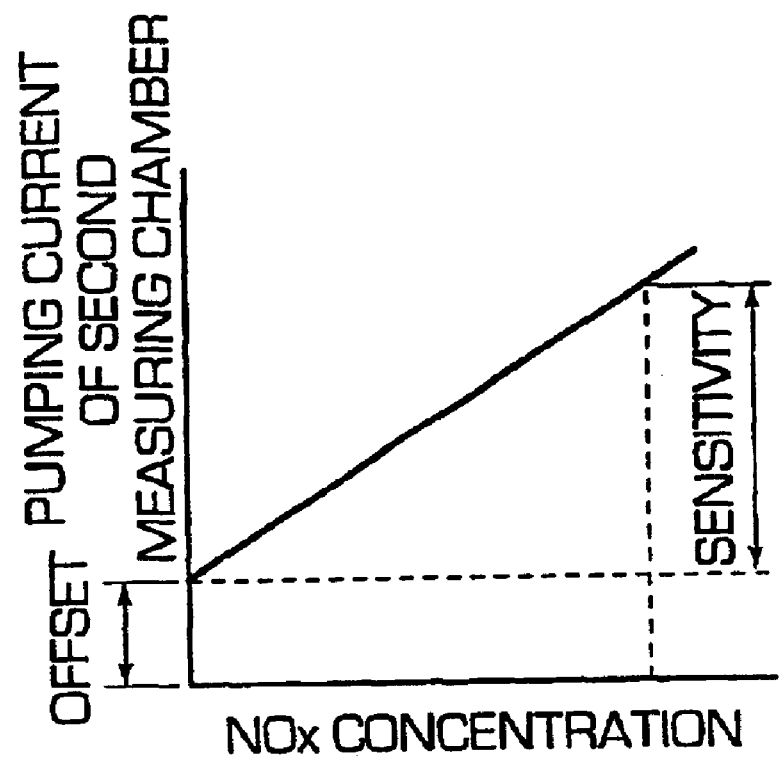
FIG. 24 is a diagram for illustrating the principle of measuring the NOx gas concentration.

FIG. 26 is a perspective view of a longitudinal section of a NOx gas sensor constructed in accordance with the present invention, while the NOx gas sensor constructed in accordance with the present invention comprises, two sets of diffusion resistance portions, oxygen ion pumping cells and measurement chambers, as seen in FIG. 1. The structure of the invention and the basic principle of its operation may be seen with respect to FIGS. 1, 23 and 24. FIG. 1 is a cross-sectional view shown shaded in FIG. 23, and FIG. 24 is a graph shown the relation between the pump current of the second measurement chamber (second oxygen ion pump current) and the NOx gas concentration.

The principle of measurement using the illustrated structure is as follows:

(1) The exhaust gas flows into a first measurement chamber 2 via first diffusion holes 1 having diffusion resistance.

(2) By a first oxygen ion pumping cell 6, oxygen in the first measurement chamber 2 is pumped out, generally to an extent that will prevent the decomposition of NOx to entirely or to a desired degree. To achieve such control, the oxygen partial pressure in the first measurement chamber 2 is controlled by a signal outputted by an oxygen partial pressure detection electrode, namely the oxygen concentration measurement cell 7.

(3) The gas in the first measurement chamber 2 (concentration-controlled O2 gas+NOx gas) flows into the second measurement chamber 4 via the second diffusion hole 3 having a diffusion resistance.

(4) The NOx gas in the second measurement chamber 4 is decomposed into N2+O2 by further pumping out oxygen by the second oxygen ion pumping cell 8.

(5) Since there is a linear relation between the second oxygen ion pump current Ip2 flowing in the second oxygen ion pumping cell 8 and the NOx gas concentration, as seen in FIG. 24, the NOx gas concentration can be detected by detecting Ip2.

In the NOx gas concentration measurement method, having the above-described measurement principle, if moisture exists in the measurement gas, an offset may be changed in response to the amount of the moisture, although the sensitivity (1/gain) is not thereby affected. Since the value of the second oxygen ion pump current (second measurement chamber pump electric current value) will be affected by the amount of moisture in the measurement gas, the NOx gas concentration cannot be measured correctly, as illustrated in FIG. 24. Thus, in accordance with a first aspect of the present invention, the second oxygen ion pump electric current value (detection signal) is corrected based on the amount of the moisture in the measurement gas. Specifically, a correction value, corresponding to the amount of moisture, is applied for enabling accurate measurement of the NOx gas concentration.

Figure 25:
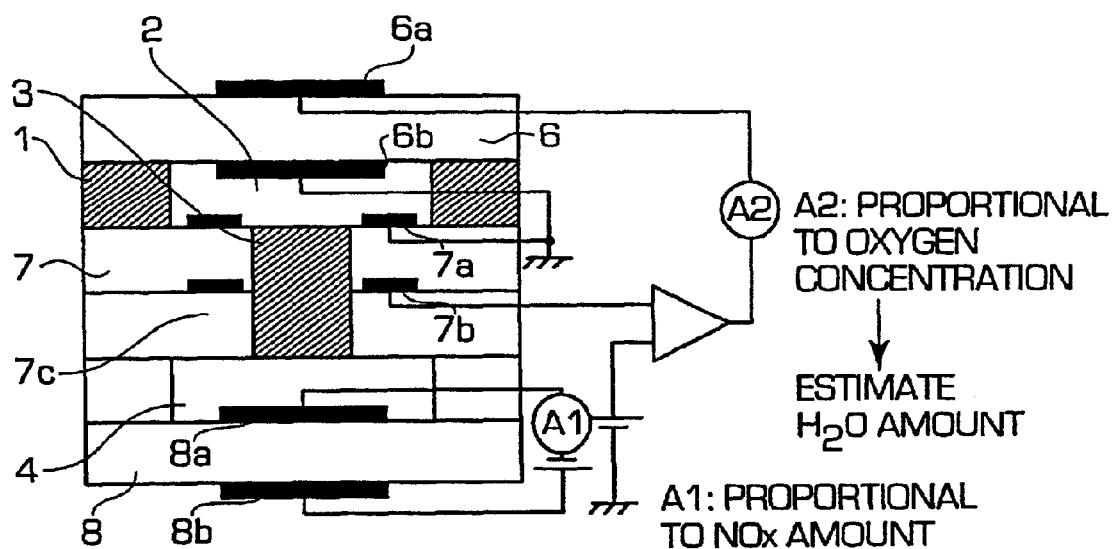
FIG. 25 illustrates a cross-section in a short side direction of a NOx gas sensor used in an embodiment of the present invention and schematics of a control system.

In one configuration of a NOx gas sensor, to which the above-described output correction method, is applied, uses a basic sensor structure. Specifically, this gas sensor preferably includes a solid electrolyte layer provided with a pair of electrodes of the second oxygen ion pumping cell, another solid electrolyte layer provided with an oxygen partial pressure detection electrode (oxygen concentration measurement cell) and the above-mentioned second measurement chamber provided between the two solid electrolyte layers. As seen in FIGS. 1, 25 and 26, the preferred NOx gas sensor is characterized in that the first oxygen ion pumping cell 6, oxygen concentration measurement cell 7 and the second oxygen ion pumping cell 8 are provided in respective different solid electrolyte layers. This structure deceases the leak current flowing between respective cell electrodes to permit the oxygen concentration in the first measurement chamber to be controlled accurately. More preferably, insulating films or layers of alumina are provided between respective cells.

Also preferably, heating layers for heating a detector are provided between stacked solid electrolyte layers. The first and second oxygen ion pumping cells can be stabilized in capability by provision of the heating layers.

As the solid electrolyte layers of the respective cells, a solid solution of zirconia and yttria or a solid solution of zirconia and calcia is used. The porous electrodes formed on both sides of the thin-plate-shaped solid electrolyte layers by printing and sintering etc. are preferably formed of catalytic materials such as platinum, rhodium, palladium, rhenium, iridium or alloys thereof. As first and second diffusion holes, porous alumina ceramic, such as porous alumina ceramics, may also be used. It is preferred that the heating portions of the heaters are formed of a composite material of ceramics and platinum or platinum alloys, while lead portions are formed of platinum or platinum alloys.

Meanwhile, the fourth feature of the present invention may be applied for detecting the concentration of other gases e.g., CO, CO2 or HC gases. The concentration of the measurement gas can be measured accurately in a manner exempt from the effects of oxygen concentration as in the case of detection of the NOx gas concentration.

Other desirable features are as stated in the JP Patent Application No.9-159195 by the present Applicant. The contents of these applications are incorporated into the present application by reference.

Referring to FIG. 4, the method for measuring the NOx gas concentration, oxygen concentration and air-to-fuel ratio according to an embodiment of the first feature of the present invention is explained. First, using a detection gas having known oxygen concentration and NOx concentration values, the gain and the offset of the NOx gas concentration corresponding to the oxygen concentration, gain of the oxygen concentration (electric current value per a standard oxygen concentration), and offset (first oxygen pump current for 0% oxygen concentration) are found. Next, a detection gas having unknown NOx gas concentration etc. are measured. Referring to FIG. 4, the first oxygen pump current IP1 is measured (step 401). Then, based on IP1, the oxygen concentration is calculated and found (411 to 412). An air-to-fuel ratio is then calculated and outputted (421 to 422). Also, responsive to the oxygen concentration, calculated from IP1, the offset and the gain of the NOx gas concentration, previously found, are read out and, using these read-out values and the measured value of the second oxygen pump current IP2, a NOx gas concentration is calculated and outputted (steps 402 to 407). The sequence of calculations shown in FIG. 4 can be executed by a micro computer connected to a sensor. Alternatively, a measurement device, such as ammeter, may be connected to the sensor and calculations may be executed based on the displayed results too. Alternatively, gain correction of the NOx gas concentration, exhibiting certain specific oxygen concentration dependency, may be executed by utilizing the output of the first oxygen ion pumping cell and by varying the amplification factor of a NOx gas concentration output circuit using an analog circuit.

Next a preferred embodiment for the second feature of the present invention is explained. That is, PID control is performed by the circuit configuration shown in FIG. 6, so that the electromotive force generated in the oxygen partial pressure detection electrodes in the first measurement chamber will be constant. If at this time a control target voltage of the oxygen partial pressure detection cell (setting of the electromotive force generated in the oxygen partial pressure detection cell) is changed, the second oxygen ion pump current is changed. Therefore, offsets of the second oxygen ion pump current relative to the voltage setting of the oxygen partial pressure detection cell are previously measured and entered as a map in a memory of a controller or the like. It during rapid changes in the oxygen concentration in the measurement gas, an electromotive force generated across the oxygen partial pressure detection cell is changed, an offset value corresponding to this electromotive force is read out to increase or decrease this amount of offset with respect to the second oxygen ion pump current for enabling more accurate detection of the NOx gas concentration.

Although it is desirable to detect the oxygen partial pressure in the second measurement chamber to correct the second oxygen ion pump current, it is necessary to provide electrodes newly. Thus the oxygen partial pressure detection cell for controlling the oxygen concentration in the first measurement chamber may be used for performing the correction. Also preferably, a reference electrode for the oxygen partial pressure detection cell may be provided in a reference oxygen chamber to cause a minor current to flow to assure a constant oxygen concentration in the atmosphere around the reference electrode to enable correct detection of the oxygen concentration in the measurement chamber.

Next a preferred embodiment for the third feature of the present invention is explained. A desirable gas sensor for the third feature of the present invention is a gas sensor capable of detecting the concentration of harmful components in the exhaust gases, such as combustible CO, HC and/or NOx components. As a CO sensor, a gas sensor employing an oxide semiconductor device, such as $In_2O_3$, may be used As the HC sensor, such as gas sensor may be used which is provided with an oxygen pump element and an oxygen concentration cell element, both exposed to the detection gas, and which finds the concentration of the combustible gas components from the electric current values flowing in the oxygen pumping cell element when the electromotive force generated in the oxygen concentration cell element reaches a value not higher than a pre-set value. A gas sensor may be used which is provided with an oxygen pumping cell an oxygen sensor cell and a combustible gas component detection unit formed of an oxide semiconductor. Also, a NOx sensor may be used which is provided with two sets of diffusion resistance portions, oxygen ion pumping cells and gaps. The measurement principle of this NOx sensor is as follows:

(1) Exhaust gases flow into the first gap via a first diffusion resistance portion having a diffusion resistance. (2) By the fist oxygen ion pumping cell, oxygen in the first gap is sufficiently pumped out such as not to cause generally all NOx (or occasionally NOx) in the first gap to be decomposed (the oxygen partial pressure in the first gap is controlled by an output signal from a second diffusion resistance portion). (3) The gas in the first gap (concentration-controlled O2 gas or NOx gas) flows via second diffusion resistance portion into the second gap. (4) by the second oxygen ion pumping cell further pumping out oxygen, NOx in the second gap is decomposed into N2 and O2 gases. (5) Since there is a specific (roughly linear) relationship between the second oxygen pump current IP2 flowing in the second oxygen ion pumping cell and the NOx gas concentration, the NOx gas concentration in the exhaust gases can be detected by detecting Ip2. (6) The oxygen concentration in the exhaust gases can be measured from the first oxygen pump current IP1 flowing in the first oxygen ion pumping cell when the first oxygen ion pump current pumps out oxygen from the first gap.

Figure 21A:
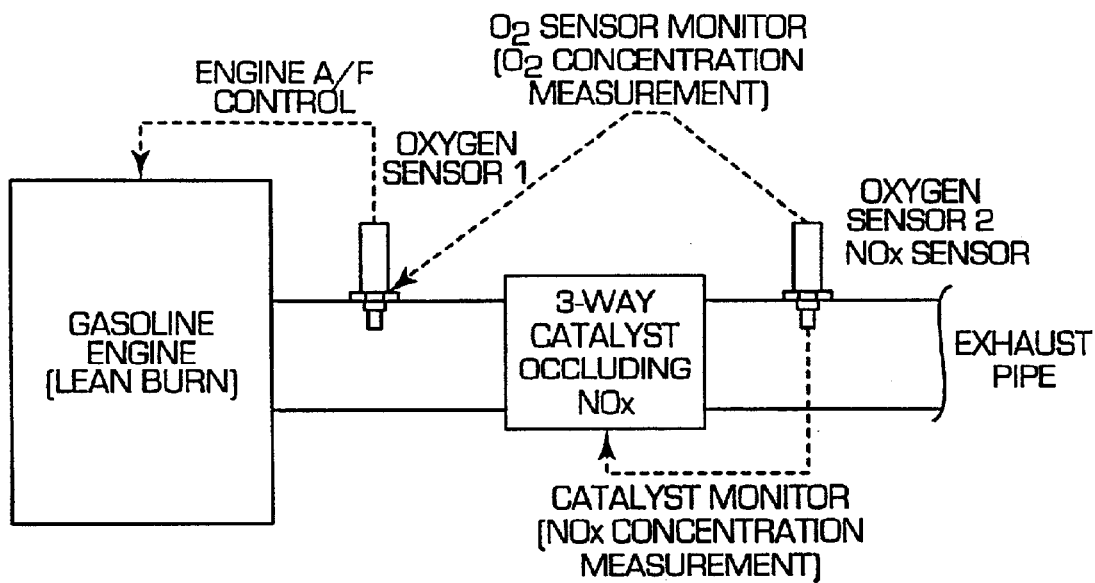

A desirable method for using the above-mentioned NOx sensor in the exhaust gas cleaning system of a gasoline engine or a diesel engine is hereafter explained. Referring to FIG. 21A, in an exhaust gas cleaning system of a gasoline engine (in particular a lean burn engine), an oxygen sensor (1), a NOx occlusion type three-way catalyst, an oxygen sensor (2) (the above elucidated NOx sensor used simultaneously as an oxygen sensor) are mounted in this order from the gasoline engine towards the downstream side. The oxygen sensor (1) is a sensor used for controlling the air-to-fuel ratio. The fuel, air or the like supplied to an engine is controlled based on a detection output of this oxygen sensor (1). On the other hand, the NOx sensor used simultaneously as the oxygen sensor, arranged downstream of the NOx occlusion type three-way catalyst, is a sensor for detecting the NOx gas concentration for checking the operating state of the three-way catalyst and the state of deterioration thereof. The engine or the like is controlled based on the detection output of the NOx sensor. This NOx occlusion type three-way catalyst affords the NOx occlusion effect to the three-way catalyst and operates as a usual three-way catalyst with excessive air ratio γ=1 (stoichiometric point) while transiently storing NOx in the lean state and periodically introducing rich spikes for cleaning transiently stored NOx. In general, the material of the NOx occlusion type three-way catalyst is Pt added to with Ba etc. having the NOx occlusive effect.

The above-mentioned NOx sensor, arranged downstream of the NOx occlusion type three-way catalyst, can be used for detecting the degree of deterioration of the NOx occlusion type three-way catalyst. That is, in introducing rich atmosphere spikes (preferably for about 3 seconds, air-to-fuel ratio of 14 to 14.5) for reducing NOx occluded in the NOx occlusion type three-way catalyst, the detection output of the NOx sensor is varied before and after the spike. If no deterioration has occurred, an output of the NOx sensor on reversion to the lean state after the spike becomes lower than that before the spike. Conversely, should there occur deterioration, NOx is not cleaned on returning from the spike to the lean state, with the NOx sensor output remaining at a high value. Thus, the degree of catalyst deterioration can be checked from changes in the NOx sensor output before and after rich spike. Since NOx is scarcely generated on spike insertion, the zero point of the NOx sensor can be calibrated.

Figure 21B:
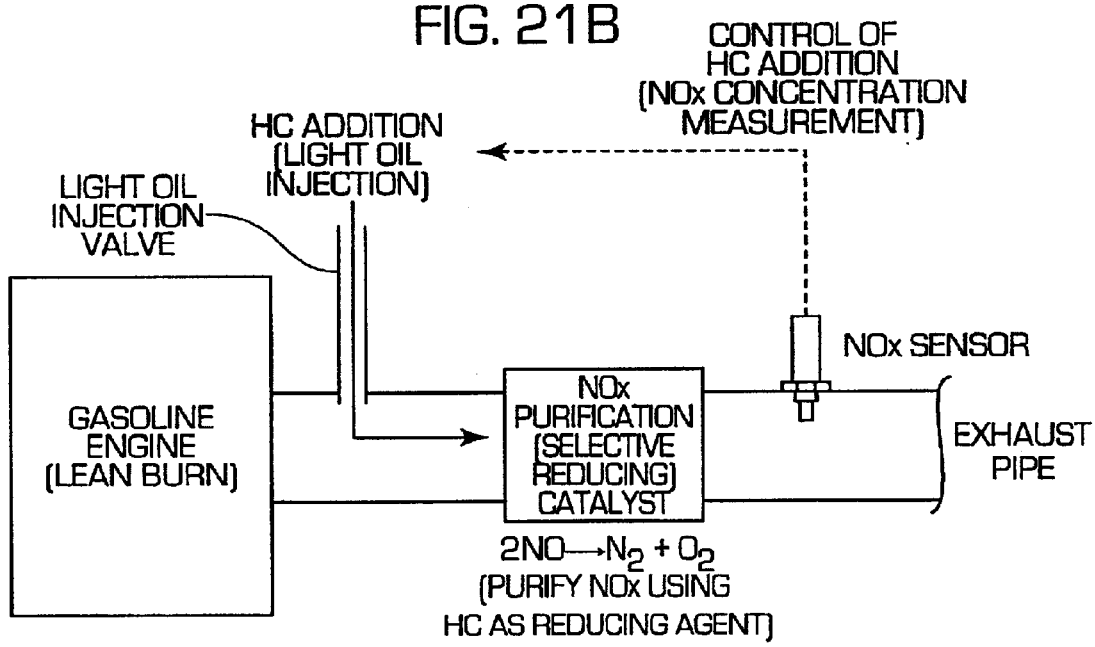

Referring to FIG. 21B, there are provided in a diesel engine exhaust gas cleaning system a light oil injection valve, a HC sensor, a NOx selective reduction catalyst and the above elucidated NOx sensor in this order. The light oil injection valve is used for injecting light oil as a HC source into the exhaust gases in the exhaust duct. The NOx selective reduction catalyst decomposes NOx into CO2 and H2O, using HC added by injection of light oil as a reducing agent, for cleaning NOx. The HC sensor is mounted upstream of the NOx selective reduction catalyst and performs the function of monitoring the HC concentration in the exhaust gases after light oil injection for performing feedback control of the amount of light oil injected into the exhaust gases. Moreover, the degree of deterioration of the NOx selective reduction catalyst can be detected based on output changes in the NOx sensor before and after HC additions. That is, with the catalyst having the capability of cleaning NOx, the NOx gas concentration downstream of the catalyst is lowered by HC addition to decrease the NOx sensor output whereas, with the catalyst lowered in its cleaning capability, the NOx gas concentration is not lowered on HC addition, so that the output of the NOx sensor is not lowered.

Figure 22:
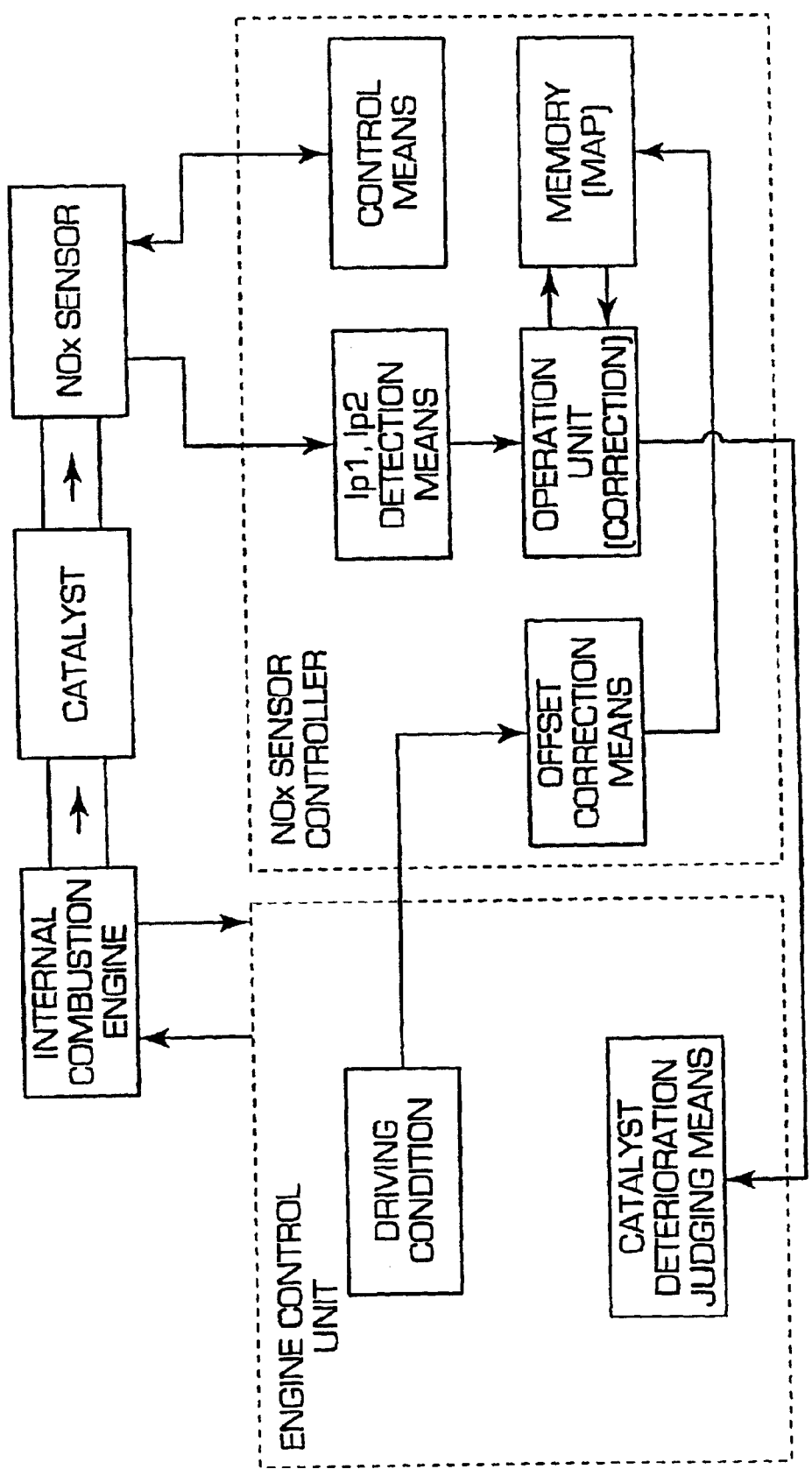
FIG. 22 illustrates an exhaust gas concentration detection system employing a NOx gas sensor according to an embodiment of the present invention.

FIG. 22 shows the control configuration of an exhaust gas concentration detection system employing a NOx sensor according to an embodiment in the third feature of the present invention. Referring to FIG. 22, this detection system has an internal combustion engine, a NOx sensor arranged downstream of the catalyst, an engine control unit (ECU) and a NOx sensor controller. The engine control unit sets the driving conditions for the internal combustion engine, such as the air-to-fuel ratio, and judges the catalyst deterioration. The NOx sensor controller includes means for controlling the NOx sensor, means for detecting and outputting the first oxygen pump current IP1 and the second oxygen pump current IP2 flowing in the NOx sensor, a memory for storing a map specifying the relation between the oxygen concentration and the IP2 offset value, an operation unit for reading out the IP2 offset from the memory and performing the operation based on an output of the detection means for outputting the results of the operation to the memory, and offset correction means supplied with a signal specifying the driving condition from the engine control unit and output signals from the IP1 and IP2 detection means for outputting an offset correction signal to the memory for storing a new offset value in the memory based on an output signal sent from the operating unit to the memory.

The operation of this system is explained. The detection means of the NOx sensor controller detects the second oxygen pump current IP2 of the NOx sensor which the operation unit outputs to the memory. The engine control unit sets a driving condition of setting the NOx gas concentration in the exhaust gases to substantially zero or to substantially the same level as atmosphere. As an example, the driving condition is set to the fuel cut time condition, that is the NOx gas concentration equal to zero, with an oxygen concentration being 20.9%. If the signal specifying the above condition, outputted by the engine control unit, and the IP1, IP2 signals corresponding to the above condition outputted by the IP1 and IP2 detection means, the offset correction means outputs a preset offset correction signal to the memory for storing IP2 detected for the above condition in association with the oxygen concentration of 20.9%. This stored value serves as a calibrated new offset value of the NOx sensor detection output corresponding to the oxygen concentration of 20.9%. The operation unit reads out offset values corresponding to the oxygen concentrations stored in the memory to perform pre-set operations based on the read-out values, IP2 under the above condition and the offset value corresponding to the oxygen concentration of 20.9%, stored in the memory. Based on the results of the operation, the offset values corresponding to the oxygen concentration are calibrated and stored in the memory. Such calibration of the detection output of the gas sensor is preferably performed periodically during the driving operation of the internal combustion engine. It may also be performed during idling.

DETAILED DESCRIPTION OF EMBODIMENTS

FIRST EMBODIMENT

A first embodiment according to the first feature of the present invention is explained in detail. In the present embodiment, the NOx gas concentration was found by the following correcting method, using the NOx gas sensor shown in FIGS. 25 to 28. The common measurement conditions were as follows:

temperature of the measurement gas: 300° C.

gas composition: NO (0 to 1500 ppm), O2 (0 to 16%); CO2 10%; balance being N2 heater power: 18 to 25 W (20 W corresponds to 800° C. in terms of the sensor temperature)

Figure 10:
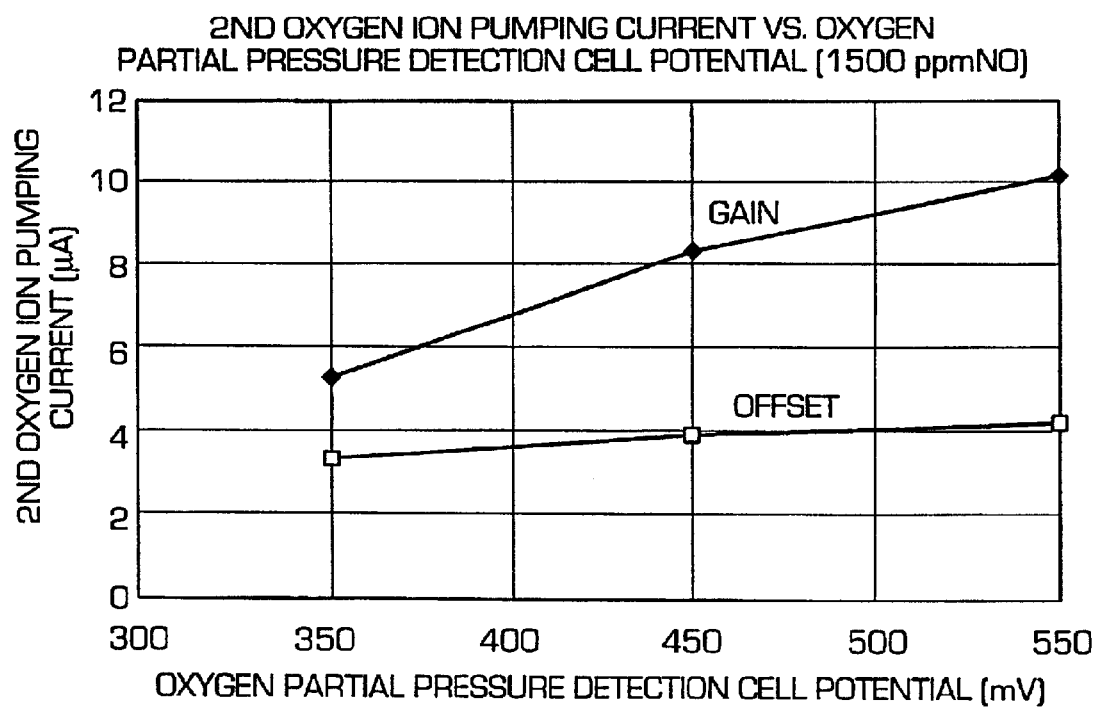
FIG. 10 illustrates the results of measurement by the NOx gas concentration measurement apparatus according to an embodiment of the present invention.

Preliminarily, the values of the second oxygen ion pump current or the NOx gas concentration at substantially zero and for a pre-sat concentration (1500 ppm) were measured at various oxygen concentration values. Using measured values of the second oxygen ion pump current as obtained for various values of the concentration of the injected NO at the pre-set oxygen concentration gain values for various oxygen concentration values (=variation of the NOx gas concentration/variation of the second oxygen ion pump current) was found by the least square method Table 1 and FIG. 10 show these results. Referring to FIG. 10, it is seen that the larger the oxygen concentration, the lower becomes the gain, so that, for finding the correct NOx gas concentration, it is necessary to correct the gain by oxygen concentration. The method for finding the coefficients of the equation for calculation in order to calculate an adequate gain by substitution of an arbitrary oxygen concentration using the gain values at each oxygen concentration shown in Table 1 is hereinafter explained.

TABLE 1

RELATION OF OXGEN CONCENTRATION AND GAIN

| $O_2$ [%] | Gain [ppm/μA] |
|---|---|
| 0 | 134.520 |
| 1 | 134.040 |
| 4 | 129.300 |
| 7 | 124.872 |
| 10 | 122.150 |
| 16 | 116.144 |
| 20 | 110.400 |

$$\text{Gain} = \text{Gain0} + \text{Gainc} \times \text{O2concent} \quad (1)$$

Gain0: VALUE OF GAIN FOR OXYGEN CONCENTRATION=0%

Gainc: GRADIENT

The gain at the preset oxygen concentration shown in Table 1 was substituted in the equation (1) and the above coeffcients (GAINo, GAINc) were determined using the least square method. The value of the gain as found by substituting an optional oxygen concentration in the equation (1) and the value of $\Delta Ip2$ shown in the following Table B2 were substituted into the equation (2), respectively, in order to find the NOx gas concentration.

$$NOx = \text{Gain} \times \Delta Ip2 \quad (2)$$

$$\text{where } \Delta Ip2 = Ip2\text{measured} - Ip2\text{offset} \quad (3)$$

Ip2 measured: VALUE OF 2ND OXYGEN PUMP CURRENT (MEASUREMENT)
Ip2offset: VALUE OF 2ND OXYGEN PUMP CURRENT FOR NOx=0% and O2=0%

For comparison, the gain values for the oxygen concentration values of 0, 1, 7 and 16% were averaged and, using the resulting averaged value as a coefficient of the equation (2), the NOx gas concentration was found. Table 2 shows the above measured value, calculated value, difference between the measured and calculated values, difference between the true value of the NOx gas concentration (injected NO concentration (A)) and the calculated value (B), and the results of the Comparative Example.

TABLE 2

CALUCULATION VALUE OF NOx CONCENTRATION AND ERROR BETWEEN CALUCUATION VALUE AND TRUE VALUE IN EXAMPLE A1 AND COMPARATIVE EXAMPLE

| $O_2$ [%] | SET NO [ppm] (A) | $\Delta Ip2$ [μA] | EXAMPLE A1 NOx[ppm] (B) | (A)–(B) | COMP. EX. NOx[ppm] (C) | (A)–(C) |
|---|---|---|---|---|---|---|
| 1 | 0 | 0.00 | 0 | 0 | 0 | 0 |
| 1 | 494 | 3.72 | 494 | 0 | 462 | 32 |
| 1 | 979 | 7.25 | 963 | 16 | 900 | 79 |
| 1 | 1469 | 10.95 | 1455 | 14 | 1359 | 110 |
| 7 | 0 | 0.00 | 0 | 0 | 0 | 0 |
| 7 | 485 | 4.15 | 513 | −28 | 515 | −30 |
| 7 | 967 | 7.95 | 982 | −15 | 987 | −20 |
| 7 | 1444 | 11.92 | 1472 | −28 | 1480 | −36 |
| 16 | 0 | 0.00 | 0 | 0 | 0 | 0 |
| 16 | 482 | 4.27 | 468 | 14 | 530 | −48 |
| 16 | 958 | 8.50 | 930 | 28 | 1055 | −97 |
| 16 | 1425 | 12.80 | 1399 | 26 | 1589 | −164 |

EXAMPLE A1: Gaino = 134.444
Gaino = −1.633

COMP. EX.: Gain = 124.124

The methods for correcting the NOx gas concentration 1 to 6 Examples 1 to 6) obtained on the basis of the second oxygen ion pump current are hereinafter explained.

Example B1: Correcting method 1

The oxygen concentration in the detection gas was set to 0, 1, 7 and 16%, the injected NO concentration was set to 0, approximately 500, approximately 1000 and approximately 1500 ppm and, for each combination of these conditions, the second oxygen ion pump current was measured. Then, assuming that the relation between the gain and the oxygen concentration is represented by the first-order equation of the least square method (case of n=1 in equation (4) as later explained)

It is seen from Table 2 that the concentration can be measured more accurately with the present correction method 1 (in particular, a lean oxygen area).

Example A2: Correction Method 2

It is assumed that the relation between the gain and the oxygen concentration is represented by the following polynominal of the least square method of the following equation (4).

$$\text{Gain} = \sum_{j=0}^{n} (Gaini \cdot O2concenti) \qquad (4)$$

where i SHOWS DEGREE IN PARTICULARLY Gaini FOR i=0 SHOWS VALUE OF GAIN FOR $O_2$=0%

In the above equation (4), the gain value for the pre-set oxygen concentration shown in Table 1 for i=2 was substituted and, using the least square method, the above coefficients (GAINi: i=0 to 2) were determined. Subsequently, the NOx gas concentration was found in the same way as in the correction method 1. Table 3 shows the above measured values, calculated values, difference between the true values of the NOx gas concentration (injected NO concentration (A)) and the calculated values (1) and the results of the Comparative Example (same as that shown in Table 2). It is seen from Table 3 that the NOx gas concentration can be found more accurately by the present correction method 2.

oxygen ion pump current was measured, respectively. Meanwhile, the oxygen partial pressure corresponds to the concentration of the above correction methods 1 and 2, expressed in terms of the partial pressure, while measured values of the injected NO concentration and the second oxygen ion pump current and the comparative example are the same as those shown in the above correction methods 1 and 2. It was assumed that the relation between the gain and the logarithm of the oxygen partial pressure was represented by a polynominal as shown by the following equation (5):

$$\text{Gain} = \text{Gain0} + \text{Gainc} \times \log(p02) \qquad (5)$$

Gain0:VALUE OF GAIN FOR OXYGEN PARTICIAL PRESSURE=1
Gainc:GRADIENT

NOx gas concentration was found by the equation (2) by a method similar to the correction method 1 except that representation by partial pressure is used in place of that by percentage (%). Table 4 shows the above measured values,

TABLE 3

CALUCULATION VALUE OF NOx CONCENTRATION AND ERROR BETWEEN CALUCUATION VALUE AND TRUE VALUE IN EXAMPLE A2 AND COMPARATIVE EXAMPLE

| $O_2$ [%] | SET NO [ppm] (A) | $\Delta Ip2[\mu A]$ | EXAMPLE A2 NOx[ppm] (B) | (A)–(B) | COMP. EX. NOx[ppm] (c) | (A)–(C) |
|---|---|---|---|---|---|---|
| 1 | 0 | 0.00 | 0 | 0 | 0 | 0 |
| 1 | 494 | 3.72 | 487 | 7 | 462 | 32 |
| 1 | 979 | 7.25 | 949 | 30 | 900 | 79 |
| 1 | 1469 | 10.95 | 1434 | 35 | 1359 | 110 |
| 7 | 0 | 0.00 | 0 | 0 | 0 | 0 |
| 7 | 485 | 4.15 | 511 | −26 | 515 | −30 |
| 7 | 967 | 7.95 | 978 | −11 | 987 | −20 |
| 7 | 1444 | 11.92 | 1467 | −23 | 1480 | −36 |
| 16 | 0 | 0.00 | 0 | 0 | 0 | 0 |
| 16 | 482 | 4.27 | 475 | 7 | 530 | −48 |
| 16 | 958 | 8.50 | 945 | 13 | 1055 | −97 |
| 16 | 1425 | 12.80 | 1423 | 2 | 1589 | −164 |
| | EXAMPLE A2: Gain (i = 0) = 132.252 | | | | COMP. EX.: Gain = 124.124 | |
| | Gain (i = 1) = −1.523 | | | | | |
| | Gain (i = 2) = 0.152 | | | | | |

Example A3: Correction Method 3

The oxygen partial pressure was set to $10^{-3}$, 0.01. 0.07 and to 0.16 and the injected NO concentration was set to 0, approximately 500, approximately 1000 and approximately 1500. For each combination of these conditions, the second calculated values, difference between true values of the NOx gas concentration injected NO concentration (A)) and the calculated value (B) and the results of comparative example. It is seen that the concentration can be measured more accurately by the present correction method 3.

TABLE 4

CALUCULATION VALUE OF NOx CONCENTRATION AND ERROR BETWEEN CALUCUATION VALUE AND TRUE VALUE IN EXAMPLE A3 AND COMPARATIVE EXAMPLE

| $O_2$ [%] | SET NO [ppm] (A) | $\Delta Ip2[\mu A]$ | EXAMPLE A3 NOx[ppm] (B) | (A)–(B) | COMP. EX. NOx[ppm] (c) | (A)–(C) |
|---|---|---|---|---|---|---|
| 1 | 0 | 0.00 | 0 | 0 | 0 | 0 |
| 1 | 494 | 3.72 | 422 | 72 | 462 | 32 |
| 1 | 979 | 7.25 | 822 | 157 | 900 | 79 |
| 1 | 1469 | 10.95 | 1448 | 21 | 1359 | 110 |
| 7 | 0 | 0.00 | 0 | 0 | 0 | 0 |
| 7 | 485 | 4.15 | 441 | 44 | 515 | −30 |
| 7 | 967 | 7.95 | 844 | 123 | 987 | −20 |
| 7 | 1444 | 11.92 | 1575 | −131 | 1480 | −36 |

TABLE 4-continued

CALUCULATION VALUE OF NOx CONCENTRATION AND ERROR BETWEEN CALUCUATION VALUE AND TRUE VALUE IN EXAMPLE A3 AND COMPARATIVE EXAMPLE

| $O_2$ [%] | SET NO [ppm] (A) | $\Delta Ip2[\mu A]$ | EXAMPLE A3 NOx[ppm] (B) | (A)–(B) | COMP. EX. NOx[ppm] (c) | (A)–(C) |
|---|---|---|---|---|---|---|
| 16 | 0 | 0.00 | 0 | 0 | 0 | 0 |
| 16 | 482 | 4.27 | 440 | 42 | 530 | −48 |
| 16 | 958 | 8.50 | 876 | 82 | 1055 | −97 |
| 16 | 1425 | 12.80 | 1690 | −265 | 1589 | −164 |
| | EXAMPLE A3: Gaino = 96.1 Gaino = −8.56 | | | | Comp. Ex. : Gain = 124.124 | |

Example A4: Correction method 4

Next gain values for a number of oxygen concentration values were found by a method similar to that for finding the gain for each value of oxygen concentration shown in Table 1. The results are shown in Table 5:

TABLE 5

RELATION OF OXGEN CONCENTRATION AND Gain

| $O_2$ [%] | Gain [ppm/$\mu A$] |
|---|---|
| 0 | 134.520 |
| 1 | 134.040 |
| 2 | 131.987 |
| 3 | 130.794 |
| 4 | 129.300 |
| 5 | 128.408 |
| 6 | 127.216 |
| 7 | 124.872 |
| 8 | 124.830 |
| 9 | 123.637 |
| 10 | 122.150 |
| 12 | 120.059 |
| 13 | 118.866 |
| 14 | 117.674 |
| 15 | 116.481 |
| 16 | 116.144 |
| 17 | 114.095 |
| 18 | 112.903 |
| 19 | 111.710 |
| 20 | 110.400 |

TABLE 5-continued

RELATION OF OXGEN CONCENTRATION AND Gain

| $O_2$ [%] | Gain [ppm/$\mu A$] |
|---|---|
| 21 | 109.324 |

In distinction from the correction method 1, the values of the gain for respective oxygen concentration values shown in Table 5 were substituted into the above equation (2) to find the NOx gas concentration. That is, the values of the gain (Table 5) for optional oxygen concentration values were stored and the stored gain values were read out depending on the oxygen concentration in the detection gas. The NOx gas concentration was calculated from the product of the read-out gain value and $\Delta Ip2$. The comparative Example is the same as that shown in a Table 2. Table 6 shows the above measured values, calculated values, difference between the true values of the NOx gas concentration (injected NO concentration (A)) and the calculated values (B) and the results of the Comparative Example. It is seen from Table 6 that the NOx gas concentration can be measured more accurately by the present correction method 4.

TABLE 6

CALUCULATION VALUE OF NOx CONCENTRATION AND ERROR BETWEEN CALUCUATION VALUE AND TRUE VALUE IN EXAMPLE A4 AND COMPARATIVE EXAMPLE

| $O_2$ [%] | SET NO [ppm] (A) | $\Delta Ip2[\mu A]$ | EXAMPLE A4 NOx[ppm] (B) | (A)–(B) | COMP. EX. NOx[ppm] (c) | (A)–(C) |
|---|---|---|---|---|---|---|
| 1 | 0 | 0.00 | 0 | 0 | 0 | 0 |
| 1 | 494 | 3.72 | 499 | −5 | 462 | 32 |
| 1 | 979 | 7.25 | 972 | 7 | 900 | 79 |
| 1 | 1469 | 10.95 | 1468 | 1 | 1359 | 110 |
| 7 | 0 | 0.00 | 0 | 0 | 0 | 0 |
| 7 | 485 | 4.15 | 523 | −38 | 515 | −30 |
| 7 | 967 | 7.95 | 1002 | −35 | 987 | −20 |
| 7 | 1444 | 11.92 | 1502 | −58 | 1480 | −36 |
| 16 | 0 | 0.00 | 0 | 0 | 0 | 0 |
| 16 | 482 | 4.27 | 496 | −14 | 530 | −48 |
| 16 | 958 | 8.50 | 987 | −29 | 1055 | −97 |
| 16 | 1425 | 12.80 | 1487 | −62 | 1589 | −164 |
| | EXAMPLE A4: Gain = the value of Gain in TABLE A5 | | | | COMP. EX.: Gain = 124.124 | |

Example 5

The oxygen concentration in the detection gas can be found by measuring the current flowing in the first oxygen ion pumping cell. Thus, oxygen and NO of the pre-set concentrations were injected and measurement was made of the first oxygen ion pump current Ip1 flowing at a zero oxygen concentration. The relation of proportionality according to the equation (6) exist between the oxygen concentration in the detection gas and the first oxygen ion pump current:

$$O2[\%]=(Ip1-BO2)/GO2 \quad (6)$$

BO2:VALUE OF 1ST OXYGEN PUMP CURRENT FOR O2=0%

GO2:AMOUNT OF CURRENT/UNIT OF OXYGEN CONCENTRATION

Table 7 shows the results of the oxygen concentration as found by the above equation (6). From Table 7, the oxygen concentration can be found correctly to an error value of the order of 0.2% by the present method. That is, even if the oxygen concentration in the detection gas is unknown, the oxygen concentration can be found correctly from the first oxygen pump current so that the gain and the offset for measuring the NOx gas concentration in meeting with the oxygen concentration in the detection gas can be determined correctly to find the NOx gas concentration correctly. This also indicates that the present sensor can measure the NOx gas concentration and the oxygen concentration simultaneously. Moreover, these measured values can be used to find the air-to-fuel ratio.

TABLE 7

CALUCULATION VALUE OF OXYGEN CONCENTRATION USING 1ST OXYGEN PUMPING CURRENT

| SET O$_2$ [%] | SET NO [ppm] (A) | I$_{pl}$ [mA] | O$_2$ (CAL.) [%] |
|---|---|---|---|
| 0.96 | 0 | 0.350 | 1.09 |
| 6.75 | 0 | 2.413 | 6.55 |
| 6.68 | 485 | 2.392 | 6.49 |
| 15.34 | 958 | 5.666 | 15.15 |

SECOND EMBODIMENT

A second embodiment incorporating the second feature of the present invention is explained. The NOx gas sensor of the present embodiment represents an application of the NOx gas sensor explained with reference to FIGS. 15 and 19 to 21A and 21B to the control configuration shown in FIG. 8.

(Measurement Example B1)

First, measurements were carried out of the gain and the offset of the second oxygen ion pump current when a measurement gas containing 1500 ppm of NO and 7% of oxygen was injected into the control system, with the second oxygen ion pumping cell potential remaining constant, and the setting voltage of an oxygen partial pressure detection cell was varied. The results are sown in FIG. 9. Also, measurements were made of the gain and the offset of the second oxygen ion pump current when the measurement gas containing 1500 ppm of NO and 7% of oxygen was injected, with the setting voltage of the oxygen partial pressure detection cell remaining constant, and the second oxygen ion pumping cell potential was varied. The results are shown in FIG. 10.

Figure 9:
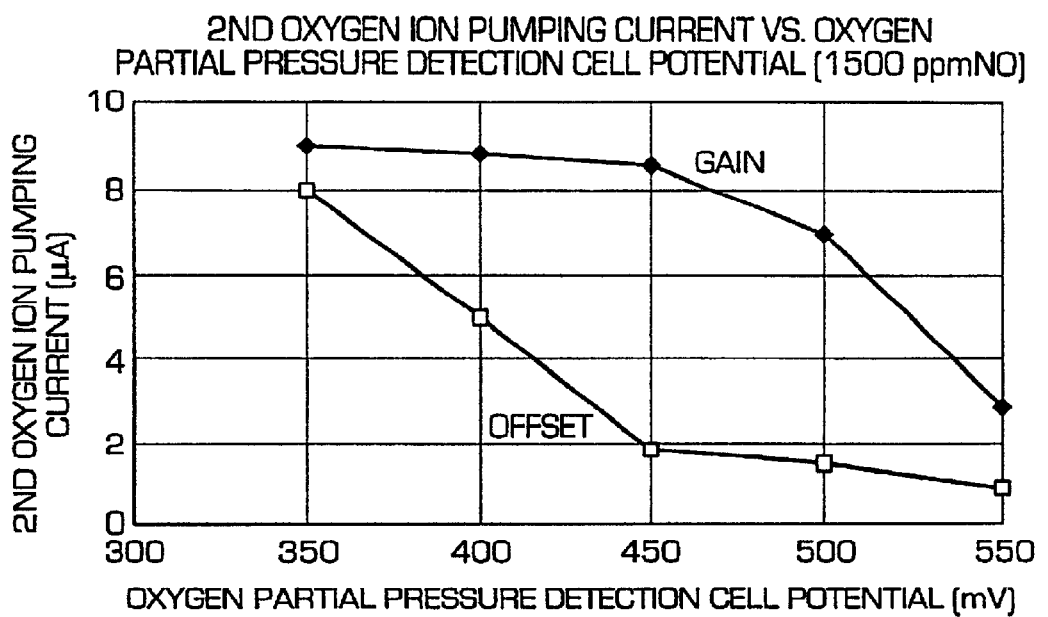
FIG. 9 illustrates the results of measurement by the NOx gas concentration measurement apparatus according to an embodiment of the present invention.

It is seen from FIG. 9 that, if the sewing voltage of the oxygen partial pressure detection cell is lowered, the oxygen left in the measurement gas diffused into a second measurement chamber is increased to increase the second oxygen ion pump current, whereas, if the setting voltage is increased, the second oxygen ion pump current is decreased. On the other hand, it is seen from FIG. 10 that if the setting voltage of the oxygen partial pressure detection cell is constant, with the oxygen concentration in the first measurement chamber being kept constant, the second oxygen ion pump current is decreased or increased as the second oxygen ion pump current is lowered or raised, respectively.

Therefore, if characteristics shown in FIGS. 9 and 10 are exploited and the second oxygen ion pumping cell voltage is (a)lowered or (b)raised when the electromotive force generated in the oxygen partial pressure detection cell is (a)high or (b)low, respectively, the effects of oxygen in the measurement gas and changes in the oxygen concentration cancel each other to pout accurate measurement of the concentration of the NOx gas in the measurement gas.

Figure 11:
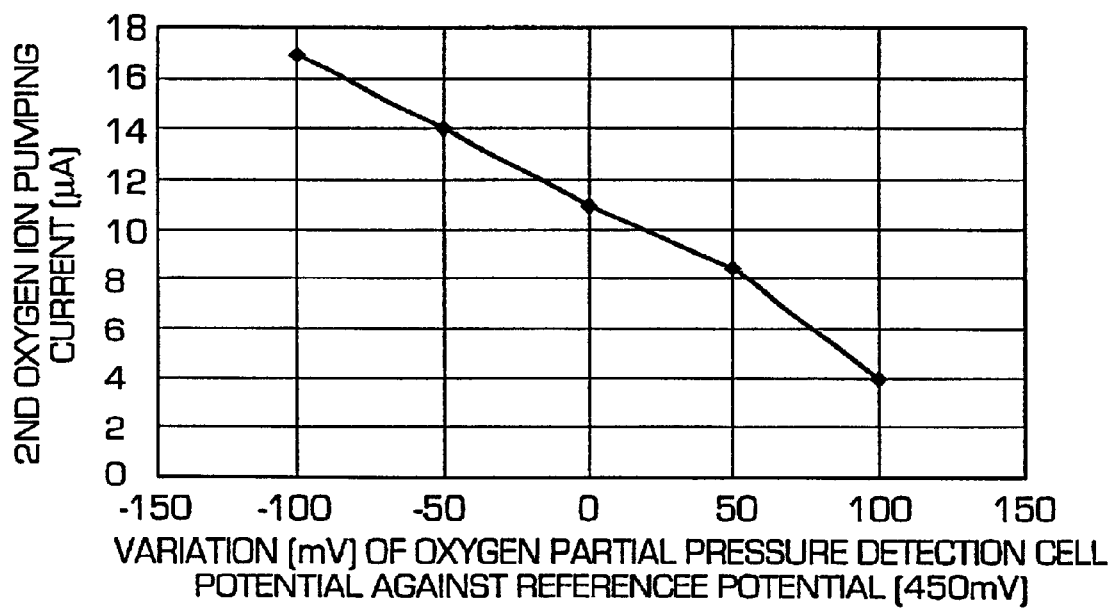
FIG. 11 illustrates the results of measurement by the NOx gas concentration measurement apparatus according to an embodiment of the present invention.

FIG. 11 shows the relation of the second oxygen ion pump current versus the difference (variation) of the potential between the reference potential (450 mV) and a measured potential of the electrode 7b of the oxygen partial pressure detection cell (FIG. 6) and the second oxygen ion pump current. It is seen from FIG. 11 that a substantially linear relation exists between the two. Thus, by holding the relation in a memory of a controller 40 (map formulation) and by reading out a pre-set offset corresponding to changes in the electromotive force in the oxygen partial pressure detection cell caused by rapid changes in the oxygen concentration in the measurement gas, and further by increasing or decreasing the measured second oxygen ion pump electric current value depending on the read-out offset value, the correct value of the NOx gas concentration can be found based on the corrected second oxygen ion pumping cell output.

(Measurement Example B2)

Figure 12:
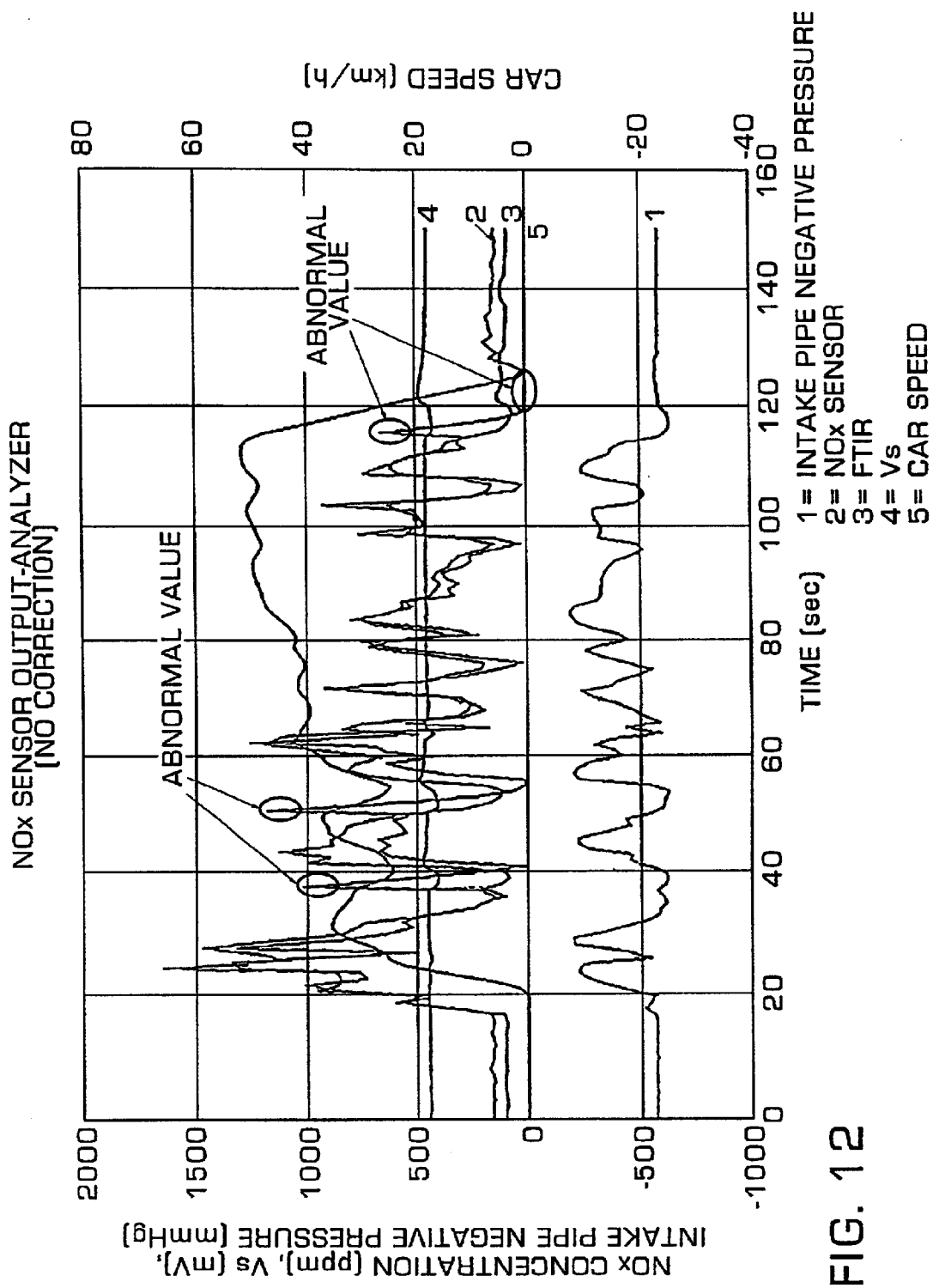
FIG. 12 shows the results of measurement of the concentration of exhaust gases of a 1.5L lean burn gasoline engine using the NOx gas measurement device according to a comparative example.
Figure 13:
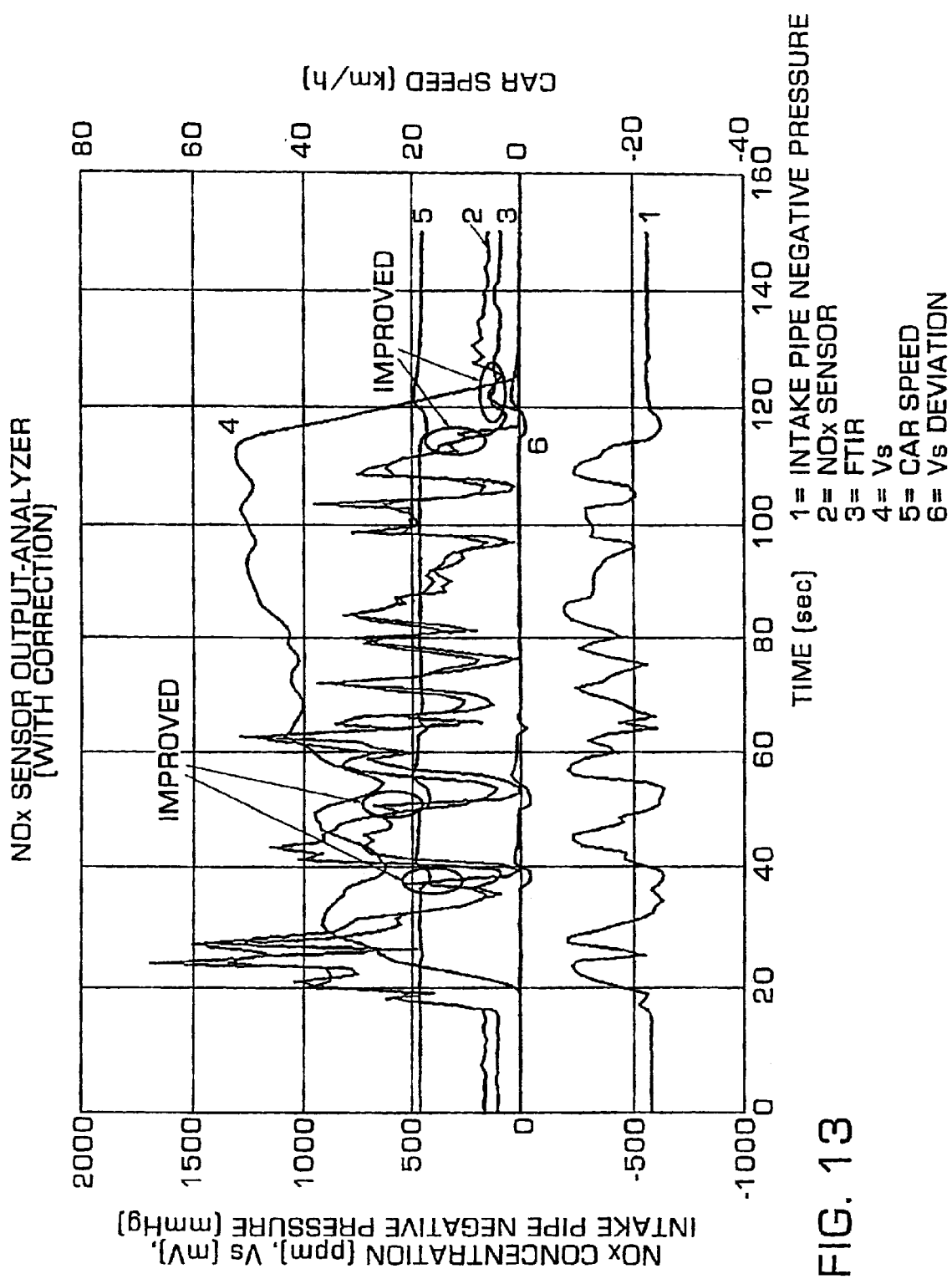
FIG. 13 shows the results of measurement of exhaust gases of a 1.5 L lean burn gasoline engine using a NOx gas measurement apparatus according to an embodiment of the present invention.

The previously-described control device (sec FIG. 8) was applied to a lean burn gasoline engine vehicle of 1.5 L to measure the NOx gas concentration in the exhaust gases. As a comparative example, similar measurements were conducted using a controller without correction by an output of the oxygen partial pressure detection cell (see FIG. 7). The setting voltage of the oxygen partial pressure detection cell was set to 450 mV. Simultaneously, true values were measured using an analyzer based on the FTIR method (the analyzer output is indicated at (3) FTIR). FIGS. 12 and 13 show the measured results of the Comparative Example and the Example, respectively. It is seen from FIGS. 12 and 13 that, in actual vehicle running, the oxygen concentration is varied with time such that control delay occurs in the control operation of controlling the oxygen partial pressure detection cell aiming at a constant potential. FIG. 12 shows that, if the oxygen partial pressure detection cell current is varied suddenly, the NOx sensor outputs an abnormal value (based on the second oxygen ion pump current) thus indicating that the NOx sensor output (2) differs significantly from the analyzer output (3) such that measured values of the NOx gas concentration were not correct.

On the other hand, FIG. 13 shows that, by reading out a pre-set offset corresponding to the difference in potential (changes in the electromotive force) between the measured potential of the electrode 7b of the oxygen partial pressure detection cell (see FIG. 6) and the reference potential (450 mV) and by performing the correction of increasing or decreasing the measured second oxygen ion pump electric current value based on the read-out offset value, the NOx sensor output peaks on occurrence of abrupt changes in the oxygen partial pressure detection cell potential assume heights less than one-half as compared to FIG. 12, with the NOx sensor output (2) being substantially equivalent to the analyzer output (3), which demonstrates that measured values of the NOx gas concentration were correct.

Figure 14:
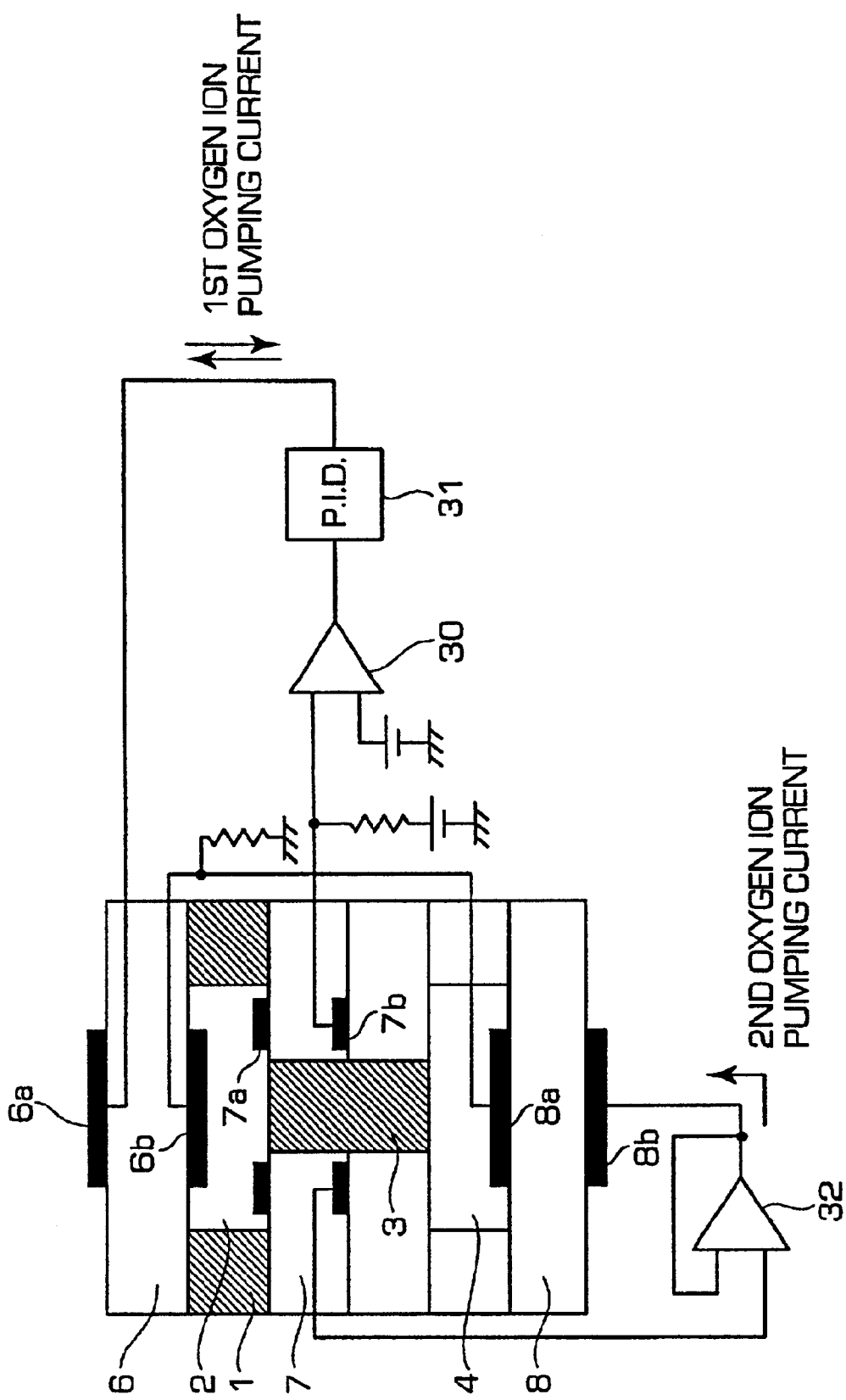
FIG. 14 illustrates a NOx gas sensor control apparatus according to another embodiment of the present invention.

In the above-described embodiment, the correction is carried out in the inside of the controller 40 shown in FIG. 8. Alternatively, a pre-set circuit may be added to the system shown in FIG. 6 (a pre-set circuit may be added to the sensor used in the above embodiment). FIG. 14 illustrates a control system according to a farther embodiment of the third feature of the present invention. The system shown in FIG. 14 differs from the system shown in FIG. 6 in that an amplifier 32 is arranged between the reference electrode 7b of the oxygen detection cell 7 and the outer electrode 8b of the second oxygen ion pumping cell. The system of FIG. 14 varies the voltage applied across the second oxygen ion pumping cell responsive to the difference (changes in potential) between the potential produced across the electrode 7b (see FIG. 6) of the oxygen partial pressure detection cell and the reference potential to effect the above control by the hardware in place of the software type correction. That is, the pump voltage applied across the second oxygen ion pumping cell is controlled so that the pump voltage will be varied as the potential of the oxygen partial pressure detection cell varies. It was found by a measurement test similar to that of the above embodiment that, with the system shown in FIG. 14, correct NOx gas concentration measurement is similarly possible as in the above embodiment as compared to the case in which the voltage applied across the second oxygen ion pumping cell is controlled to a constant value.

THIRD EMBODIMENT

Figure 15:
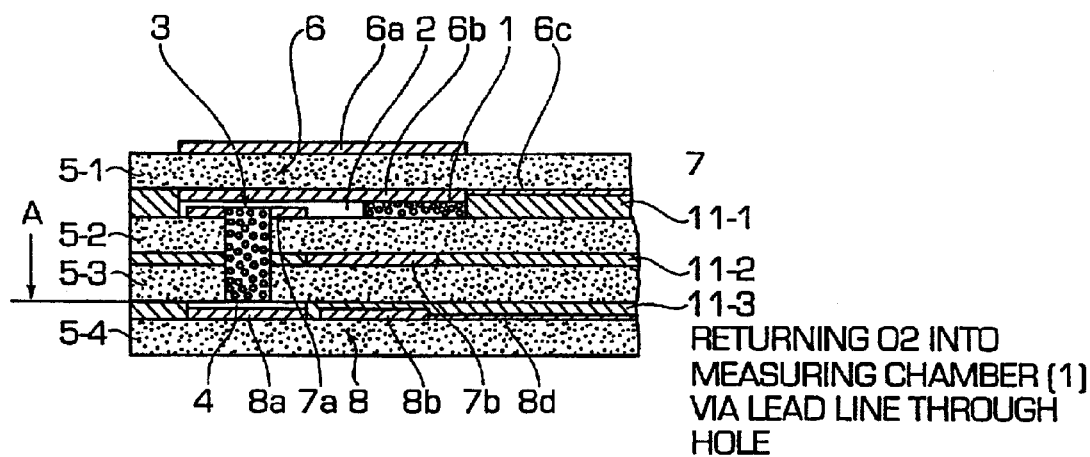
FIG. 15 is a schematic view for illustrating the structure of a NOx gas sensor employed in an embodiment of the present invention.

An embodiment according to the third feature of the present invention is explained. In the present embodiment, the NOx sensor having a structure shown in FIG. 15 is used. The NOx sensor of FIG. 15 includes a first oxygen ion pumping cell 6, having a pair of electrodes 6a, 6b provided on both sides of a solid electrolyte layer 5-1, an oxygen concentration measurement cell 7 having a pair of oxygen partial pressure detection electrodes 7a, 7b, provided on both sides of a solid electrolyte layer 5-2, and a second oxygen ion pumping cell 8 having a pair of electrodes 8a, 8b provided on the surfaces of a solid electrolyte layer 5-3 and a solid electrolyte layer 5-4, stacked in this order. Between the solid electrolyte layers 5-1, 5-2, 5-3 and 5-4 are formed insulating layers 11-1, 11-2 and 11-3, respectively. Between layers of the first oxygen ion pumping cell 6 and the oxygen concentration measurement cell 7 is defined the first measurement chamber (gap portion) 2 by the left and right side insulating layer 11-1 and the upper and lower side solid electrolyte layers 5-1 and 5-2. Similarly, the second measurement chamber 4 (gap portion) is defined above the second oxygen ion pumping cell 8 by the insulating layer 11-3 and the solid electrolyte layers 5-3 and 54. Moreover, first diffusion hole 1 having a diffusion resistance (diffusion resistance portion) is provided on each side in the short side direction of the sensor (front and back sides in FIG. 15) on one side in the first measurement chamber 2. On the other side in the first measurement chamber 2 is formed with an opening of the second diffusion hole 3 (diffusion resistance portion) separated from the first diffusion holes 1. The second diffusion hole 3 is passed through the oxygen concentration measurement cell 7 and the solid electrolyte layer 5-3 to establish communication between the first and second measurement chambers 2 and 4 with a diffusion resistance.

Figure 16:
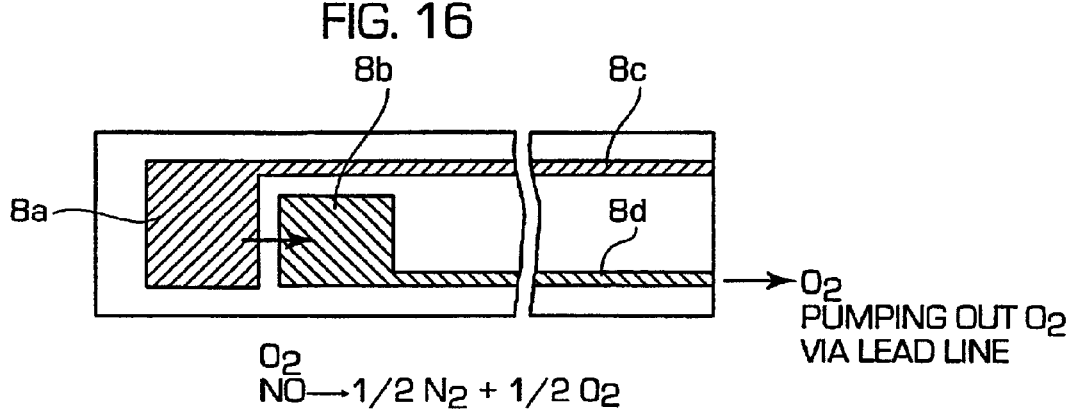
FIG. 16 illustrates the cross-section indicated by arrow A in FIG. 15.

In the present sensor, electrodes 8a, 8b of porous metal (such as Pt or Rh alloys) are formed on the same surface of the solid electrolyte layer 5-4 making up the second oxygen ion pumping cell 8. Although the electrodes 8a, 8b are isolated from each other via the insulating layer 11-3, oxygen ions are conducted via the solid electrolyte layer 54 to cause the second oxygen pump current Ip2 to flow by this oxygen ion conduction. The electrode 8b is prohibited by the solid electrolyte layer 5-4, insulating layer 11-3 and a lead (line) 8d from direct contact with the sensor atmosphere. Moreover, oxygen pumped out by the second oxygen ion pumping cell 8 can be led to outside via porous lead 8d having a diffusion resistance. Moreover, leads 8c (see FIG. 16) and 8d (see FIG. 16) are electrically connected to the electrodes 8a, 8b, while the lead 8d electrically connected to the outer electrode 8b of the second measurement chamber 4 is porous to permit oxygen ion diffusion. Thus, oxygen decomposed by the NOx gas and pumped from the electrode 8a to the electrode 8b is discharged via lead 8d FIG. 16 shows the planar cross-section taken along arrow line A in FIG. 16. It is seen by referring to FIG. 16 that the lead 8d is contacted with outside air (atmospheric air or ambient atmosphere of the measurement gas) for communication between outside air and the electrode 8b via a diffusion resistance.

The principle of measurement of the NOx sensor shown in FIG. 15 is as explained in the column of the preferred embodiment. Specifically, controller terminals are electrically connected via leads to respective electrodes of the NOx sensor such that the electromotive force corresponding to the oxygen concentration in the measurement gas, introduced by diffusion into the first measurement chamber 2 via the first diffusion holes 1, is generated across the electrodes 7a, 7b of the oxygen concentration measurement cell 7. The voltage applied across the first oxygen ion pumping cell 6 by the differential amplifier is controlled so that the voltage produced by this electromotive force will be constant (control by the controller may be digital control using a microcomputer or analog control). As excess oxygen is pumped out, the measurement gas having a pre-set oxygen concentration is diffused via the second diffusion hole 3 into the second measurement chamber 4 and the voltage is applied across the electrodes 8a, 8b of the second oxygen ion pumping cell 8 for further pumping out residual oxygen NOx is decomposed into N and O2 by the catalytic action of the electrodes of Pt alloys or rhodium alloys. This O is converted into ions and transmitted in the solid electrolyte layer 5-4 of the second oxygen ion pumping cell 8 so that the current corresponding to the amount of the decomposed NOx gas flows across the electrodes 8a, 8b of the second oxygen ion pumping cell 8. The NOx gas concentration can be measured by measuring this IP2.

With this NOx sensor, in which the electrode 8b serving as an opposite side electrode with respect to the electrode 8a of the second oxygen ion pumping cell 8 in the second measurement chamber 4 is installed in the inside of the device (between layered solid electrolytes), the solid electrolyte layer 5-4 and the insulating layer 11-3 serve as protection means for the electrode 8b, with the lead portion 8d serving as diffusion resistance means to interrupt the electrode 8b from the atmosphere of the measurement gas (exhaust gases) to prevent it from direct contact with outside air. Moreover, pumped-out oxygen is pooled in the vicinity of the electrode 8b to stabilize the oxygen concentration around (in the vicinity of) the electrode 8b to stabilize the electromotive force generated across the paired electrodes 8a, 8b of the second oxygen ion pumping cell 8. Moreover, since the generated electromotive force is stabilized, the effective pump voltage (Vp2−electromotive force) of the pump voltage Vp2 applied across the second oxygen ion pump cell 8 is stabilized to decrease oxygen concentration dependency in the measurement of the NOx concentration.

Manufacturing Example C

Figure 17:
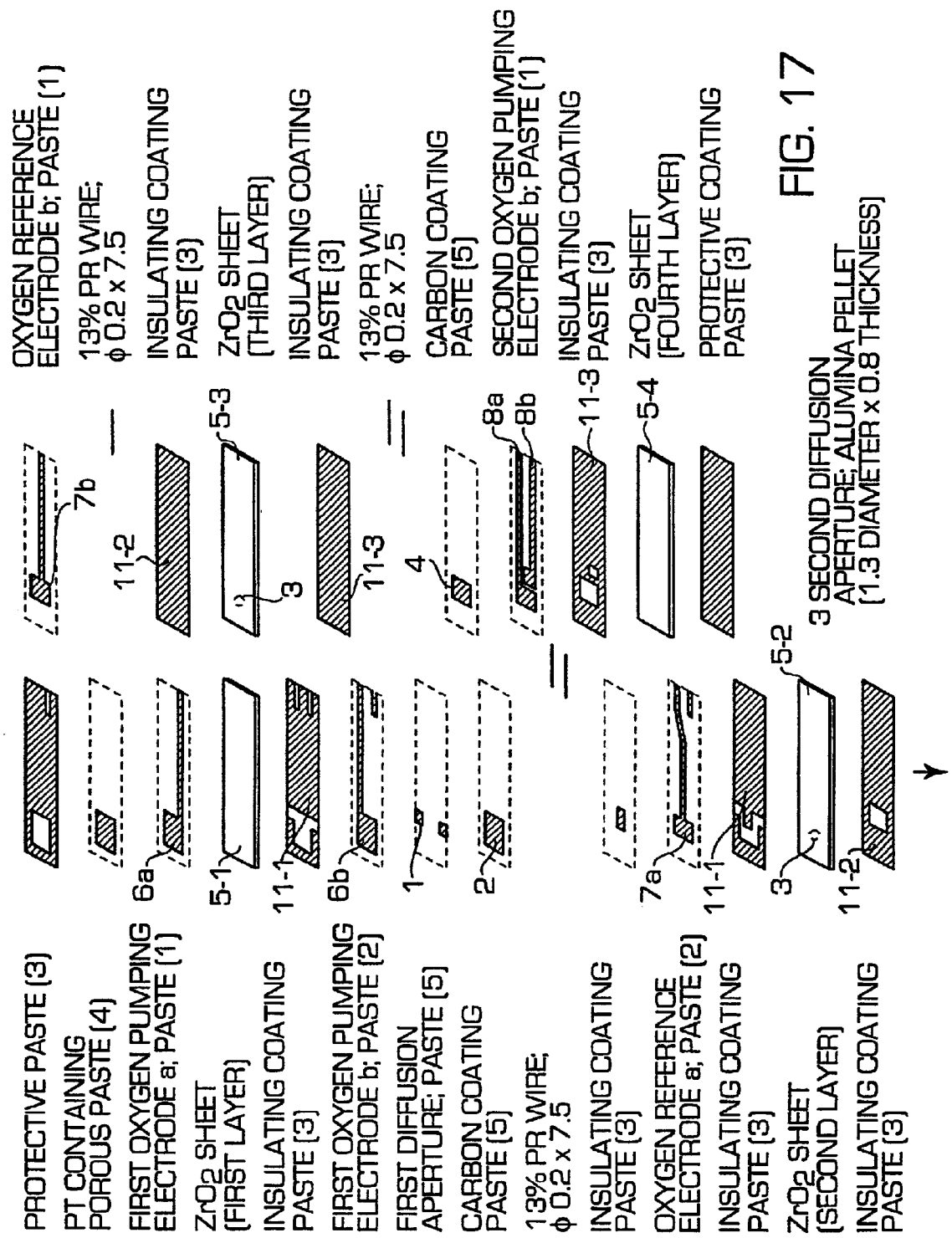
FIG. 17 illustrates the layout of a NOx gas sensor shown in FIG. 15.

Next, a manufacturing method or a NOx sensor shown in FIG. 15 is explained. FIG. 17 is a layout view of the NOx sensor shown in FIG. 15. Although the sheet and the paste shown in FIG. 17 are in the green state, the same reference numerals as those used for the NOx sensor shown in FIG. 15 are used. The ZrO green sheet and the paste for the electrode are layered from upper left to lower left and then from upper right to lower right in FIG. 17, dried and fired to form an integral sensor. The paste materials, such as insulating coat or electrodes, are layered by screen printing on a pre-set ZrO2 green sheet. The manufacturing example of the component parts such as ZrO2 green sheet is as described before.

Use Example C

The NOx sensor, thus produced, having a structure as shown in FIG. 15, was mounted on an actual apparatus and put to a durability test continuing for 500 hours. The structure of the NOx gas concentration sensor is like that shown in FIG. 22, while the mounting position of the NOx gas sensor is like that shown in FIG. 21. The controller controlling the NOx gas sensor has a memory in which to store the gain value ((standard NOx gas concentration−0)/(generated current volume−offset)) of a detection output of the NOx gas sensor as set using a model gas (valuation device as later explained (second oxygen pump current). In particular, the offset values corresponding to various oxygen concentration values from the oxygen concentration of 0% to 20.9% (21%) are stored in the memory for cancelling its oxygen concentration dependency. In this manner, optimum offset values are read out based on the oxygen concentration as found from the first oxygen pump current for setting optimum offset values used for calculating the NOx gas concentration.

Figure 18:
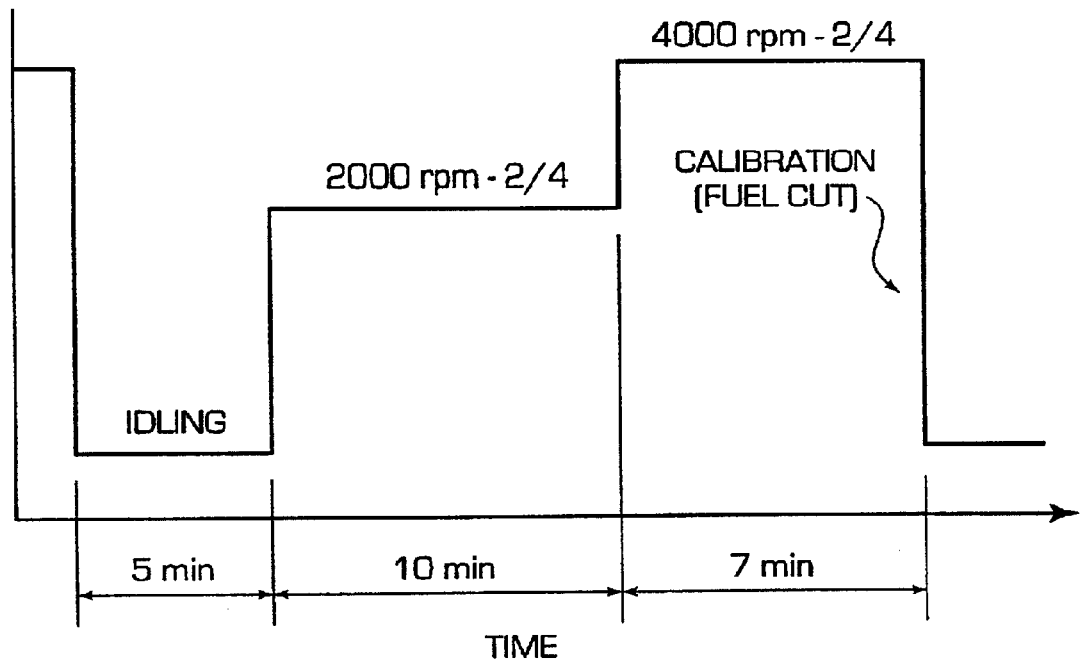
FIG. 18 illustrates the results of a durability test conducted using a NOx gas sensor shown in FIG. 15.
Figure 19:
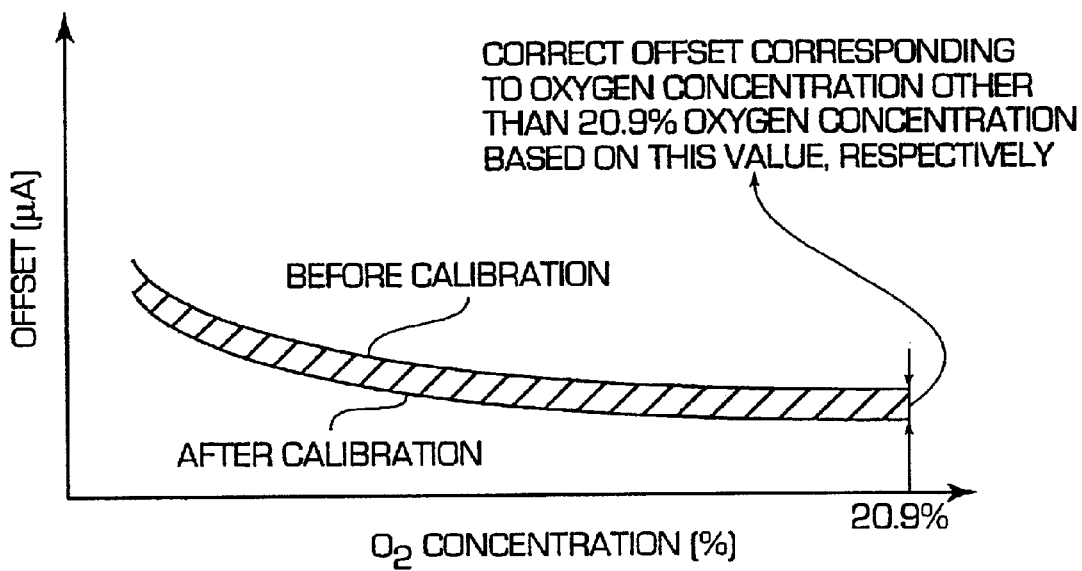
FIG. 19 illustrates the result of a calibration of the detection output of the NOx gas sensor according to an embodiment of the present invention.

Two sets of the controllers and the NOx sensors were prepared and initial characteristics of NOx gas sensors thereof were measured on a model gas evaluation device. The controllers were adjusted so that, when the analyzer output indicated zero NOx gas concentration, the controller detection output corresponding to the second oxygen pump current will be equal to zero. These NOx gas sensors were then mounted on an exhaust pipe of a gasoline engine with a displacement of 3000 cc, and a 500 hour durability test was conducted in a mode shown in FIG. 18, during which the NOx gas sensors were controlled by the respective controllers (numerals affixed to the indication of the number of revolutions depict relative opening degree of the accelerators). In one of the controllers, the correction method of the embodiment was executed to calibrate the offset (zero point) during fuel cut for the durability mode. In the other controller, the zero point was not calibrated. The calibration method by the former controller is as follows:

That is, referring to FIG. 19, when the fuel cut signal output from the engine control unit (ECU) of the gasoline engine is entered, the value of the controller detection output proportionate to the second oxygen pump current, is stored as an offset value (OF2) corresponding to O2=20.9%. The offset value (OF1) in the memory, corresponding to O2=20.9%, is read out to find the difference between OF1 and OF2. The resulting "OF1−OF2" is subtracted from the offset value (OF[O2]) corresponding to each oxygen concentration stored in the memory to give a value (OF[O2]−(OF1−OF2)) which is stored in the memory as a calibrated new offset value OF[O2].

Figure 20:
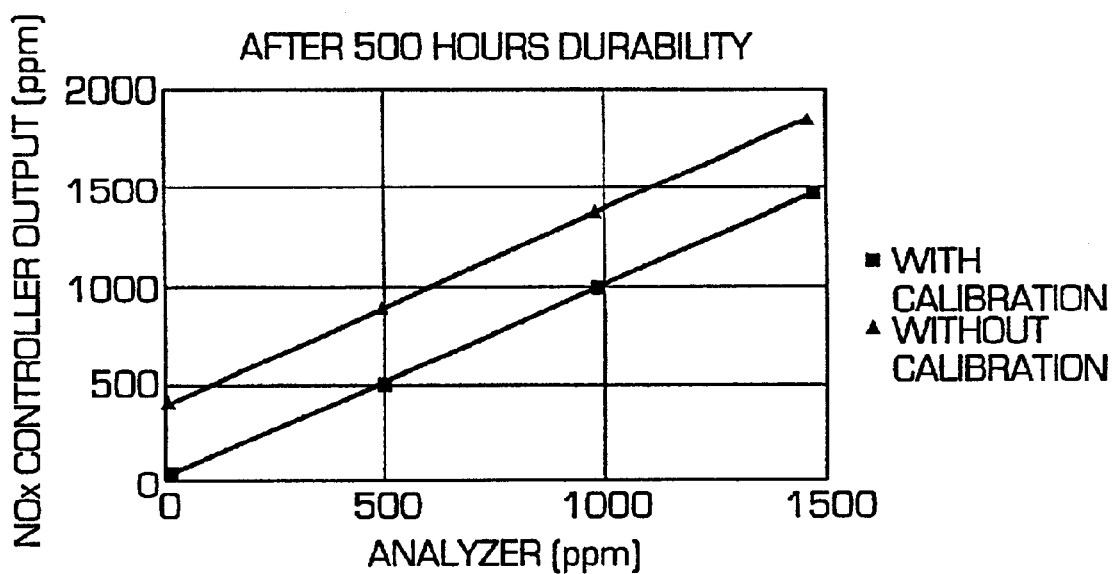
FIG. 20 illustrates the results of the durability test comparing an embodiment of the invention and a comparative example.

Referring to the results of the durability test, shown in FIG. 20, the detection output of the NOx gas concentration of the controller of the system according to the calibrated embodiment indicated substantially zero change after the durability test continued for 500 hours. Conversely, the output was increased by approximately 400 ppm for the system of the comparative example for which no calibration was carried out.

FOURTH EMBODIMENT

An embodiment in the fourth feature of the present invention is explained. The sensor shown in FIGS. 25 and 26 includes a first oxygen ion pumping cell 6, having a pair of electrodes 6a, 6b provided on both sides of a solid electrolyte layer, an oxygen concentration measurement cell 7 having a pair of oxygen partial pressure detection electrodes 7a, 7b, provided on both sides of a solid electrolyte layer, and a second oxygen ion pumping cell 8 having a pair of electrodes 8a, 8b on both sides of a solid electrolyte layer, stacked in this order, with an insulating layer interposed between neighboring solid electrolyte layers, respectively. A first measurement chamber 2 is defined by an insulating layer and the solid electrolyte layers between the first oxygen ion pumping cell 6 and the oxygen concentration measurement cell 7. Similarly, a second measurement chamber 4 is defined above the second oxygen ion pumping cell 8 (see FIG. 25) by the insulating layer and the solid electrolyte layers. In the wall surface surrounding the first measurement chamber 2 are formed plural first diffusion holes 1 having diffusion resistance (see FIG. 27), and a second diffusion hole 3 is formed at a mid portion of the first measurement chamber 2 in a spaced-apart relation from the first diffusion holes 1. The second diffusion hole 3 is passed through the oxygen concentration measurement cell 7 and the solid electrolyte layers for communication between the first and second measurement chambers 2 and 4 with diffusion resistance.

The measurement principle of the sensor is as described in the column of the embodiment. Specifically, the electromotive force corresponding to the oxygen concentration in the measurement gas, introduced by diffusion into the first measurement chamber 2 via the first diffusion holes 1, is generated across the electrodes 7a, 7b of the oxygen concentration measurement cell 7. The voltage applied across the first oxygen ion pumping cell 6 by the differential amplifier is controlled so that the voltage produced by this electromotive force will be constant (a micro-computer may be used for control). As excess oxygen is pumped out, the measurement gas having a pre-set oxygen concentration is diffused via the second diffusion hole 3 into the second measurement chamber 4, and a voltage is applied across the electrodes 8a, 8b of the second oxygen ion pumping cell 8 for further pumping out residual oxygen NOx is decomposed into N2 and O2 by the catalytic action of the electrode of rhodium alloy. This O2 is converted into ions and transmitted in the solid electrolyte layer of the second oxygen ion pumping cell 8 so that the current corresponding to the amount of the decomposed NOx gas flows between the electrodes 8a, 8b of the second oxygen ion pumping cell 8. The NOx gas concentration can be measured by measuring this IP2.

Figure 27:
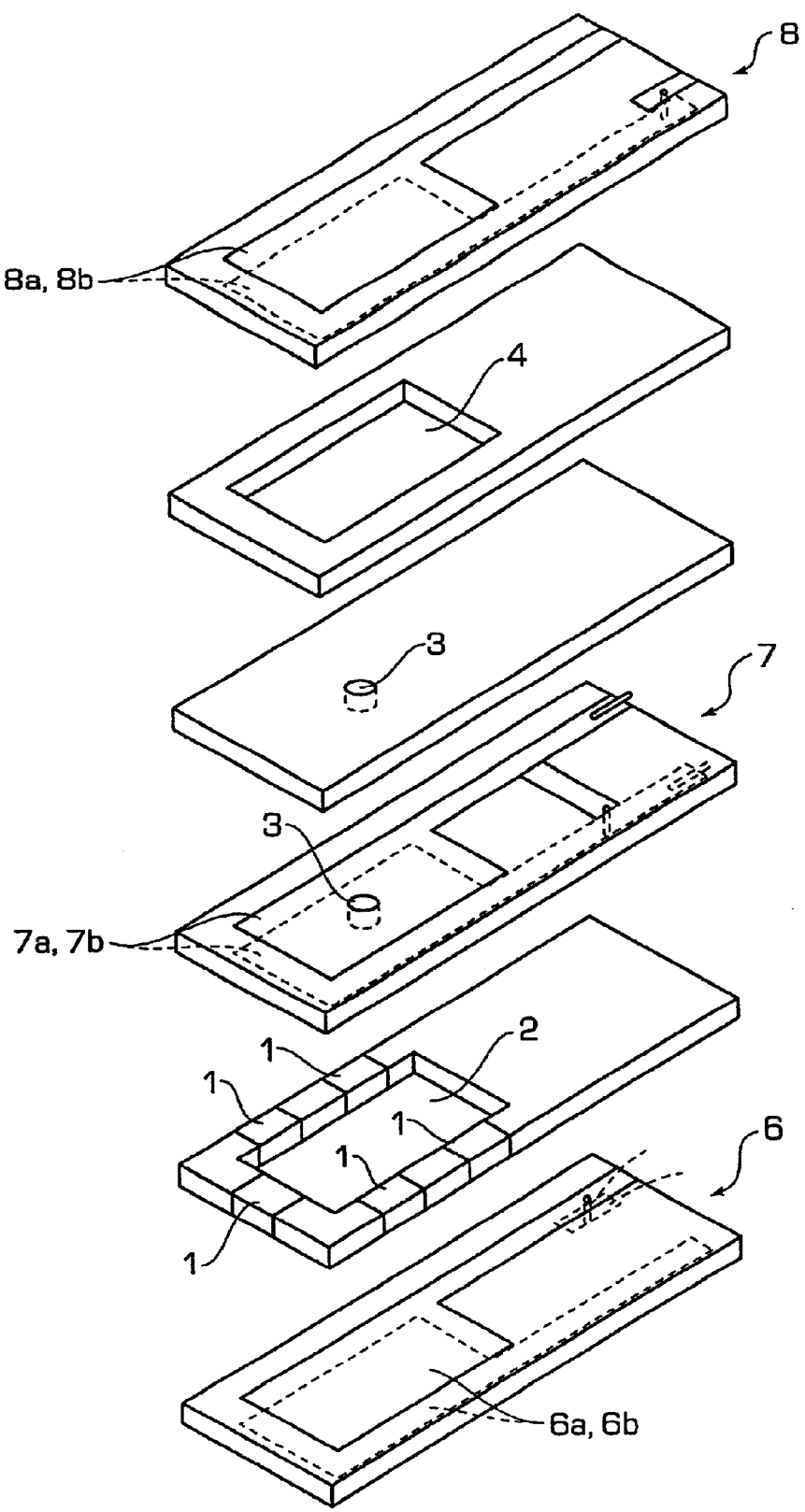
FIG. 27 shows a layout of a NOx gas sensor shown in FIG. 25.

As shown in the layout drawing of FIG. 27, this NOx gas sensor is fabricated by stacking and firing green sheets formed of an oxygen ion conducting solid electrolyte material. On the other hand, porous electrodes are formed by screen printing in the green sheet.

Using this NOx gas sensor, a test for measuring the NOx gas concentration in the measurement gas was carried out.

Figure 28:
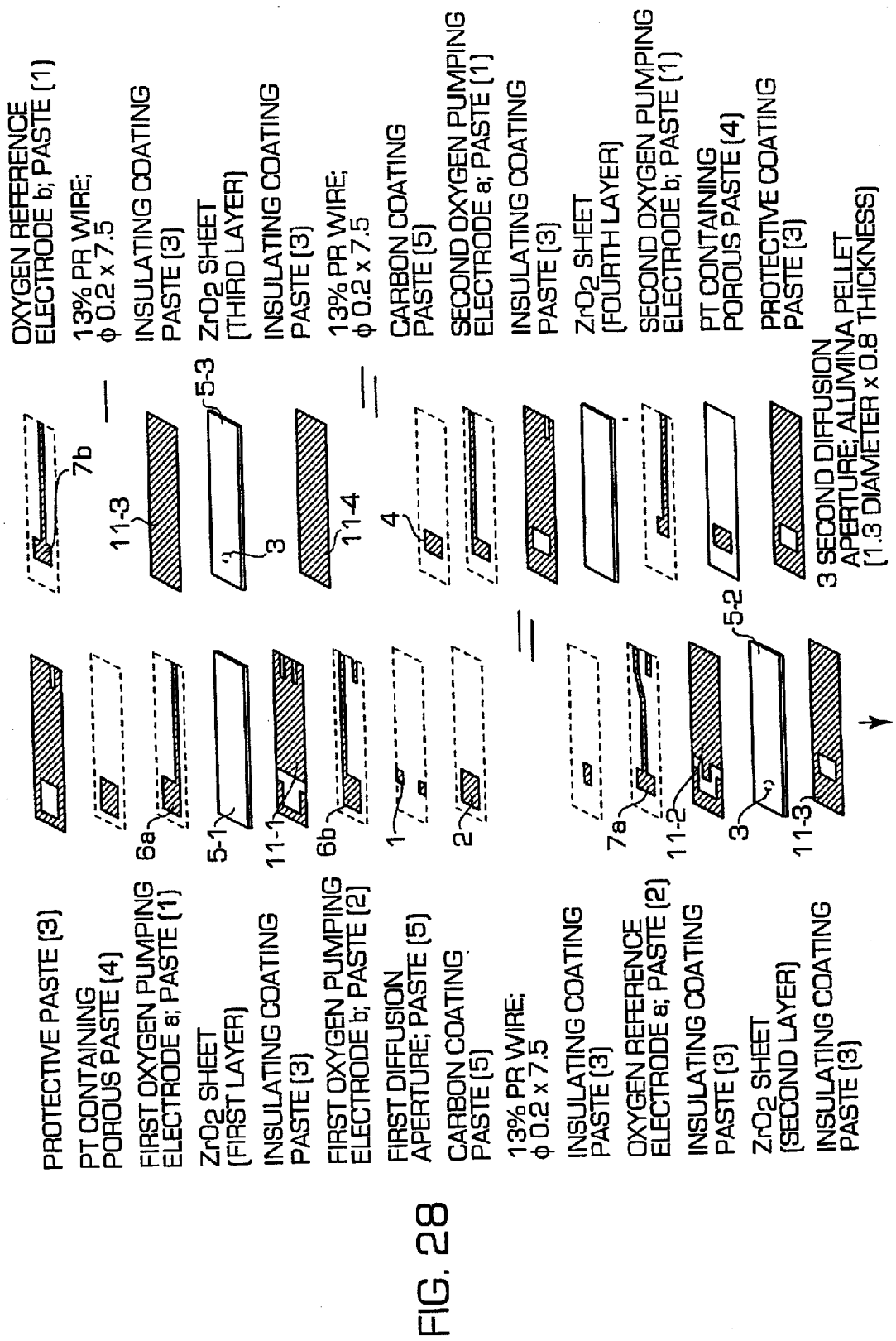
FIG. 28 illustrates a manufacturing example and the detailed layout of a NOx gas sensor used for measurement.

Referring to FIG. 28, a manufacturing example and the layout of the NOx gas sensor used for measurement are explained in detail.

Manufacturing Example

Referring to FIG. 28, ZrO2 green sheets and pastes for electrodes and so forth are laminated from upper left to lower left, then to upper right and finally to lower right to fabricate a unitary detector. Insulating coatings, electrodes or the like paste materials are laminated by screen printing on a pre-set ZrO2 green sheet. A manufacturing example for manufacturing various components such as ZrO2 green sheet is now explained.

Molding ZrO2 Sheet

ZrO2 powders were calcined in an atmospheric oven at 600° C. for two hours 30 kg of the calcined ZrO2 powders, 150 g of a dispersant and 10 kg of an organic binder were charged into a trommel along with 60 kg of balls. The resulting mass was mixed for about 50 hours for dispersion and added to with 4 kg of an organic binder dissolved in 10 kg of an organic solvent. The resulting mass was mixed for 20 hours to produce a slurry having a viscosity of 10 Pa·s. From this slurry, a ZrO2 green sheet about 0.4 mm thick was fabricated and dried at 100° C. for one hour.

Paste for Printing (1) For first oxygen ion pump electrode 6a, an oxygen partial pressure detection electrode (oxygen reference electrode b) 7b and second oxygen ion pump electrodes 8a, 8b: 20 g of platinum powders, 2.8 g of ZrO2 powders and a suitable quantity of the organic solvent were charged into a crusher (or a pot mill), mixed for four hour for dispersion and added to with 2 g of an organic binder dissolved in 20 g of the organic solvent. The resulting mass was added to with 5 g of a viscosity adjustment agent and mixed for four hours to produce a paste with a viscosity of the order of 150 Pa·s.

(2) For first oxygen ion pump electrode 6b, oxygen partial pressure detection electrodes (oxygen reference electrode a) 7a: 19.8 g of platinum powders, 2.8 g of ZrO2 powders, 0.2 g of gold powders and a suitable quantity of the organic solvent were charged into a pulverizer (or a pot mill), mixed for four hours for dispersion and added to with 2 g of an organic binder dissolved in 20 g of the organic solvent. The resulting mass was added to with 5 g of a viscosity adjustment agent and mixed for four hours to produce a paste with a viscosity of the order of 150 Pa·s.

(3) For insulating coats and protective coats: 50 g of alumina powders and a suitable amount of the organic solvent were charged into a pulverizer (or a pot mill) and mixed for 12 hours for dissolution. The resulting mass was added to with 20 g of a viscosity adjustment agent and mixed for three hours to fabricate a paste with a viscosity of the order of 100 Pa·s.

(4) For Pt-containing Porous Materials (Lead Wires): 10 g of alumina, 1.5 g of platinum powders, 2.5 g of an organic binder and 20 g of an organic solvent were charged into a pulverizer, 9 or a pot mill) and mixed for four hours. The resulting mass was added to with 10 g of a viscosity adjustment agent and mixed for four hours to fabricate a paste with a viscosity of the order of 100 Pa·s.

(5) For first diffusion hole 1:10 g of alumina powders having an average grain size of about 2 $\mu$m, 2 g of an organic binder and 20 g of an organic solvent were charged into a pulverizer (or a pot mill) and mixed for four hours. The resulting mass was added to with 10 g of a viscosity adjustment agent and mixed for four hours to fabricate a paste with a viscosity of the order of 400 Pa·s.

(6) For carbon Coat: 4 g of carbon powders, 2 g of an organic bidder and 40 g of an organic solvent were charged into a pulverizer (or a pot mill) and mixed for dispersion. The resulting mass was added to with 5 g of a viscosity adjustment agent and mixed for four hours to fabricate a paste. By forming the carbon coat by printing, electrical contact between electrodes, for example, can be eliminated. The carbon coat is used for forming first and second measurement chambers. Since carbon is burned off during firing, there is no carbon coat layer in the sintered body.

For Second Diffusion Hole 3:20 g of alumina powders, with a mean particle size of about 2 $\mu$m, 8 g of an organic binder and 20 g of an organic solvent were charged into a pulverizer (or a pot mill) and mixed for one hour. The resulting mass was granulated and pressed by a metal mold press under a pressure of approximately 2 t/cm² to fabricate a press-molded product (in the green state) in the from of a column 0.8 mm thick with a diameter of 1.3 mm. This press-molded product in the green state was inserted into a pre-set point of green sheets of the second and third ZrO2 green sheets and press-bonded together. The resulting product was then fired to form the second diffusion hole 3 in the gas sensor.

Laminating ZrO2

After pressure bonding the second and third layers, a portion to be passed through by the second diffusion hole 3 is punched. After this punching, a green columnar-shaped molded product, which serves as the second diffusion hole 3, is embedded, and the third to fourth layers of ZrO2 green sheets are pressure-bonded together under a force of pressure of 5 kg/cm² for a pressing time duration of one minute.

Binder Removal and Firing

The pressure-bonded molded product was fired at 1500° C. or one hour after removal of the binder at 400° C. for two hours.

Example of Measurement

A NOx gas sensor having the following size was fabricated in accordance with the above-described manufacturing example. A NOx gas concentration measurement test was conducted by controlling the gas sensor as shown in FIG. 25. The NOx gas sensor used for measurement is of a longitudinal length of 50 mm, a width (short-side direction) of 4 mm and a thickness (laminating direction) of 1.3 mm. The first oxygen ion pump cell is of a thickness of 0.3 mm, while the electrodes 6a, 6b is of a longitudinal length and a short-side length of 7 mm and 2 mm, respectively. The first measurement chamber is of a longitudinal length and a short-side length of 7 mm and 2 mm, respectively, with a height being 50 $\mu$m. The second measurement chamber is of the longitudinal length and a short-side length of 7 mm and 2 mm. respectively, with a height being 50 $\mu$m. The first diffusion hole is of a longitudinal length and a short-side length of 2 mm and 1 mm, respectively, with a thickness being 50 $\mu$m. The second diffusion hole is of a diameter of 1 mm.

From the value of the first oxygen ion pump current of the NOx gas sensor, that is from the amount of oxygen in the exhaust gas, the amount of moisture in the exhaust gases was estimated, and correction was made of the value of the gas concentration obtained from the gas concentration detection signal of the gas sensor, that is the value of the current flowing in the second oxygen ion pumping cell.

In the NOx gas concentration measurement test, the NO gas was sent via an exhaust gas duct of a vehicle carrying a 2000 cc diesel engine, under varying load conditions on the chassis, and outputs of a NOx gas concentration sensor and an analyzer mounted about 1 m downstream wore compared. The analyzer used was "FT-IR" (manufactured by HORIBA) capable of measuring the amount of the moisture.

Figure 30:
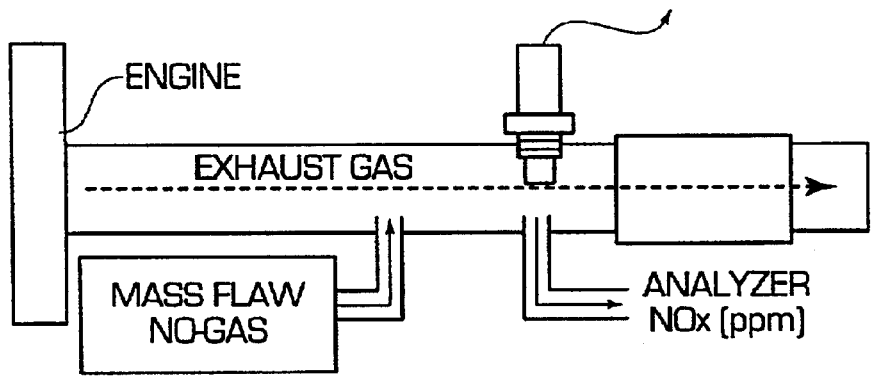
FIG. 30 shows a schematic structure of a NOx gas concentration measurement system used in an embodiment of the present invention.

A controller was connected to the NOx gas sensor so that correction of the NOx gas sensor (electric current value of the second oxygen ion pumping cell, the NOx gas concentration detection signal) by a pre-set correction amount and the NOx gas concentration (ppm) could be obtained responsive to the first oxygen ion pump electric current value of the NOx gas sensor. The schematics of the measurement system is shown in FIG. 30.

Figure 29:
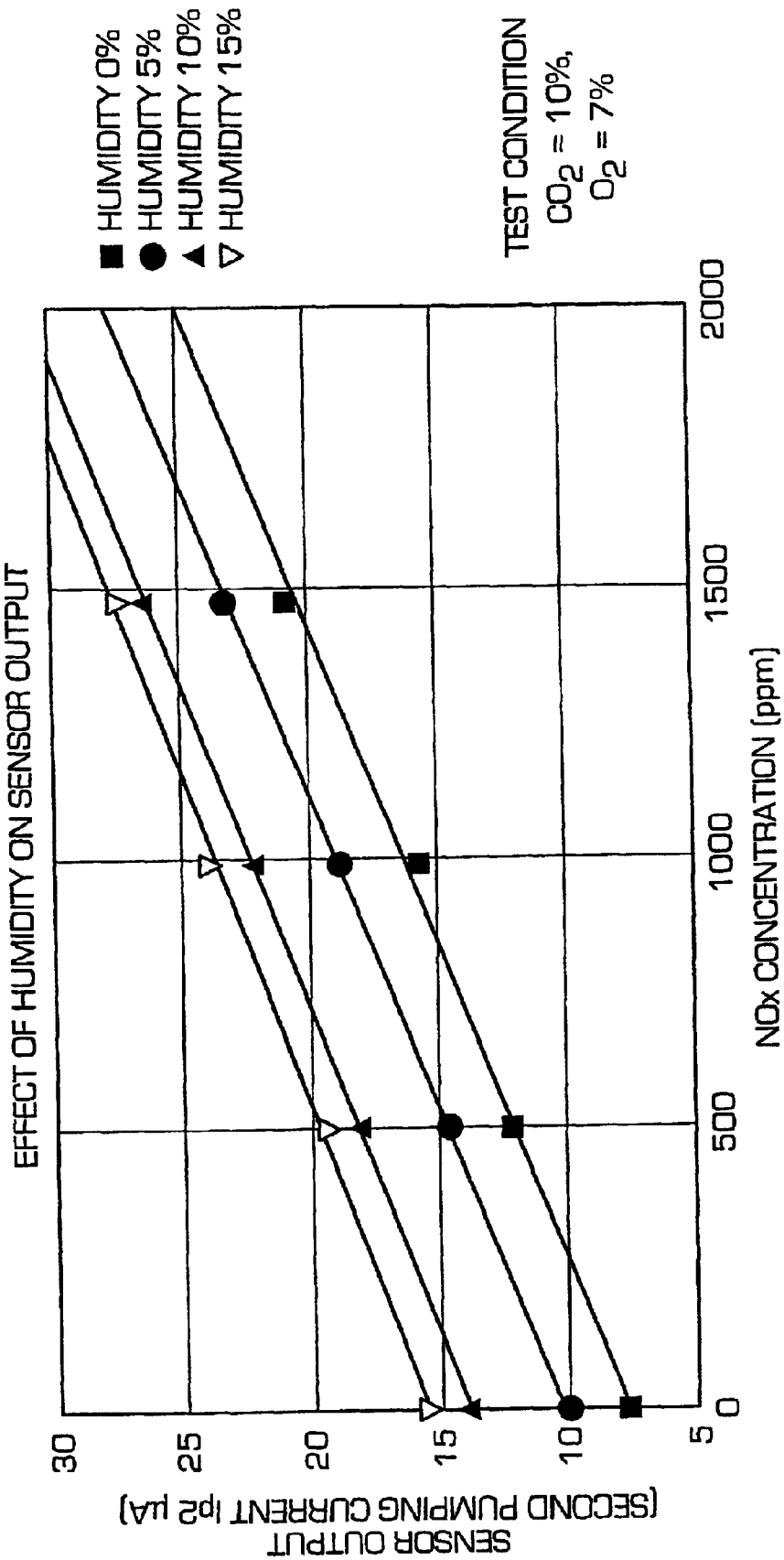
FIG. 29 is a graph showing the effect of the moisture on detection output of the NOx gas concentration of a NOx gas sensor in an embodiment of the present invention.

For setting the correction amount of the current flowing in the second oxygen ion pumping cell of the NOx gas sensor (second oxygen ion pump current), a test was conducted in advance using a model gas test device. With the gas sensor, used for measurement, current outputs of the first oxygen ion pump current of 0.5 mA per 1% of the oxygen concentration and the second oxygen ion pump current of 1 µA per 100 ppm of the NOx gas concentration were obtained, with an output increase being 0.6 µA (second oxygen ion pump current) per 1% of moisture. FIG. 29, which is a graph illustrating the effect of the moisture on the NOx gas concentration detection output of the NOx gas sensor according to an embodiment of the present invention, shows the relation between the amount of the moisture and the output increase of the gas sensor. The parameters derived from these results, that is the first oxygen ion pump electric current value and correction data of the second oxygen ion pump current corresponding to the first oxygen ion pump current value (correction coefficients and correction parameters) were entered as a map to a memory loaded on a controller so that the NOx gas concentration outputted by the detector could be connected depending on the moisture content.

Figure 31:
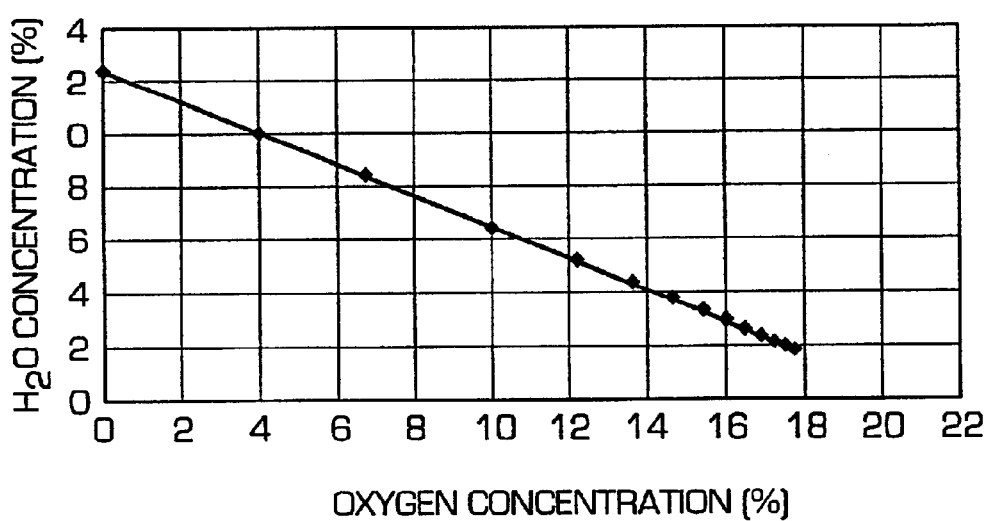
FIG. 31 is a graph showing the relation between the oxygen concentration and moisture at the time of complete combustion.

As the amount of the moisture, calculated values as found from the oxygen concentration in the exhaust gases for the assumed complete combustion were used. Table 8 and FIG. 31 show the calculated values and the relation between the amount of moisture (calculated values) and the oxygen concentration. The excess air ratio $\lambda$ means the ratio to the theoretical air quantity necessary for fuel combustion (A) of the actually supplied air quantity (B) (B/A). For example, $\lambda=1.2$ means that air is in excess by 20% as compared to the theoretical air quantity required for complete combustion. Since the oxygen concentration and the amount of the moisture are proportionate to each other as shown in FIG. 31, the amount of the moisture can be estimated from the electric current value A2 of the first oxygen ion pumping cell proportionate to the oxygen concentration (see FIG. 25).

TABLE 8

EXCESS AIR RATIO AND EXHAUST GAS COMPONENTS

| $\lambda$ | $O_2$ | $CO_2$ | $H_2O$ |
|---|---|---|---|
| 1 | 0 | 13.40303 | 12.3978 |
| 1.25 | 3.9696 | 10.85703 | 10.04275 |
| 1.5 | 6.671837 | 9.123879 | 8.439589 |
| 2 | 10.11446 | 6.915868 | 6.397178 |
| 2.5 | 12.21549 | 5.568316 | 5.150693 |
| 3 | 13.63128 | 4.660267 | 4.310747 |
| 3.5 | 14.65005 | 4.006852 | 3.706338 |
| 4 | 15.41827 | 3.514136 | 3.250575 |
| 4.5 | 16.01824 | 3.129327 | 2.894628 |
| 5 | 16.49979 | 2.820477 | 2.608941 |
| 5.5 | 16.89482 | 2.567114 | 2.37458 |
| 6 | 17.22473 | 2.355518 | 2.178855 |
| 6.5 | 17.50439 | 2.176148 | 2.012937 |
| 7 | 17.74448 | 2.022163 | 1.870501 |

Figure 32:
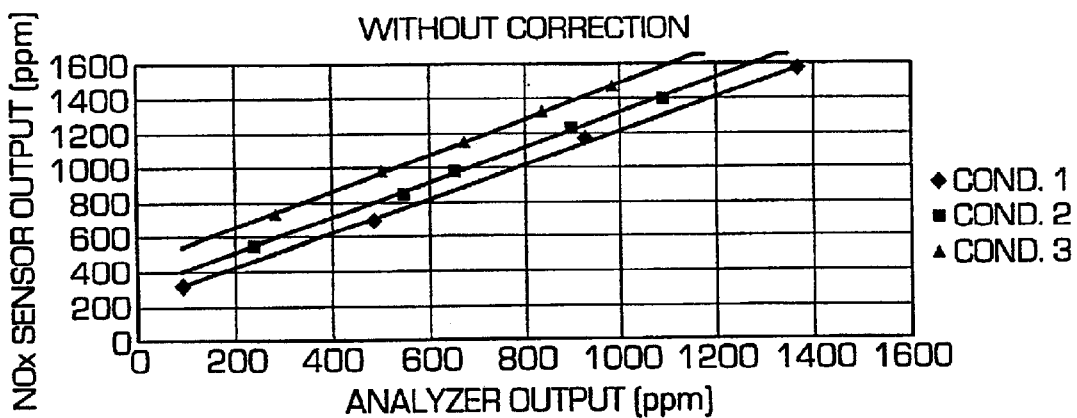
FIG. 32 illustrates results of measurement obtained by a system shown in FIG. 30.
Figure 33:
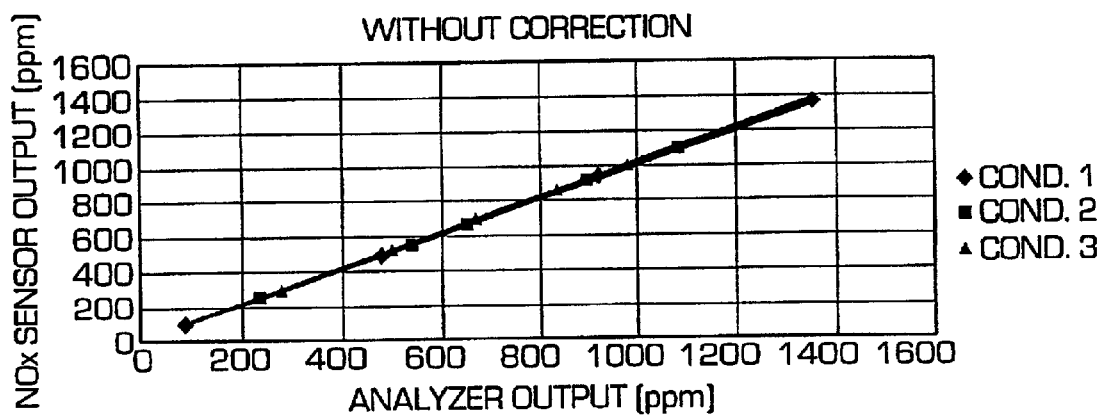
FIG. 33 illustrates the results of measurement obtained by the system shown in FIG. 30.

In three engine loading conditions (see Table 9), the NOx gas concentration obtained based on detection signals output by the NOx gas sensor (corrected value and non-corrected value) and the concentration of the NOx as output by the analyzer (true concentration) were compared to each other as the concentration of the injected NOx gas was vaned. The results are shown in Table 10, FIGS. 32 and 33. FIG. 32 and FIG. 33 plot the non-corrected NOx gas sensor output and the analyzer output and the corrected NOx gas sensor output and the analyzer output, respectively.

TABLE 9

| | ENGINE rpm | OUTPUT | EXHAUST GAS TEMPERATURE | MOISTURE |
|---|---|---|---|---|
| CONDITION 1 | 700 rpm | 0 kw | 135° C. | 3.5% |
| CONDITION 2 | 1850 rpm | 12 kw | 389° C. | 5.1% |
| CONDITION 3 | 1950 rpm | 20 kw | 524° C. | 7.5% |

TABLE 10

| | ANALYZER | NOx SENSOR WITHOUT CORRECTION | | | NOx SENSOR WITH CORRECTION | | |
|---|---|---|---|---|---|---|---|
| | | CONDITION 1 | CONDITION 2 | CONDITION 3 | CONDITION 1 | CONDITION 2 | CONDITION 3 |
| CONDITION 1 | 93 | 311 | | | 109 | | |
| | 490 | 684 | | | 475 | | |
| | 924 | 1155 | | | 944 | | |
| | 1365 | 1563 | | | 1353 | | |
| CONDITION 2 | 240 | | 550 | | | 250 | |
| | 552 | | 840 | | | 540 | |
| | 657 | | 970 | | | 670 | |
| | 897 | | 1210 | | | 910 | |
| | 1091 | | 1390 | | | 1090 | |
| CONDITION 3 | 283 | | | 725 | | | 275 |
| | 507 | | | 970 | | | 520 |
| | 676 | | | 1140 | | | 690 |
| | 834 | | | 1300 | | | 850 |
| | 983 | | | 1450 | | | 1000 |

Referring to FIG. 32, in the absence of the correction by the amount of the moisture, the offset is varied, although the sensitivity is not affected, with the gas sensor output differing with a difference in the load conditions. Therefore, the NOx gas concentration output by the gas sensor cannot indicate true values depending on the load conditions. Thus, the NOx gas concentration output by the gas sensor fails to indicate true values depending on the load conditions. Conversely, should correction be made by the moisture quantity, the corrected gas sensor output and the analyzer output (corresponding to the true NOx gas concentration) coincide with each other without regard to the load conditions (three lines in FIG. 33 overlap thus indicating substantially coincidence between the NOx sensor output value and the analyzer output value). Thus it is seen that by correction, the NOx gas concentration in the exhaust gas been obtained accurately. Although the amount of vapor in air is small as compared to the amount of exhaust gases and hence has no significant effects, the concentration of the moisture before entering the engine can be measured for achieving a higher accuracy.

FIFTH EMBODIMENT

FIG. 34 shows an embodiment of a sensor assembly in which a NOx gas sensor device according to the present invention is assembled in a metal shell (main metal fixture). This sensor assembly is so secured that a lower portion of the sensor device formed with an inlet for the measurement gas is located in a protector having holes. A heater is annexed to the sensor device, extending along its length. An outer portion of the heater annexed to the sensor device is coated with a sealing material. The sealing material (for a sensing portion of the sensor device) is of a porous material to permit passage of a gas. The sealing material for being secured in the metal fixture is of an air-proofing material. A holder is provided on an outer peripheral side of the sealing material, and a stainless steel material and a talc material are enclosed between the holder and the main metal shell for a film securing. A caulking force is applied in the axial direction for stably holding the sensor device in the assembly. Extending from the metal shell a first outer tube and a second outer tube are assembled coaxially and retained relative to each other. The first outer tube is extended into and retained by the metal shell. Within the second outer tube, water-proofing rubber is sealed. An electrode formed on the sensor is electrically connected, via an electrode lead, to an end of a sheathed lead wire with the opposite end connected to a electronic control circuit.

SIXTH EMBODIMENT

Figure 35A:
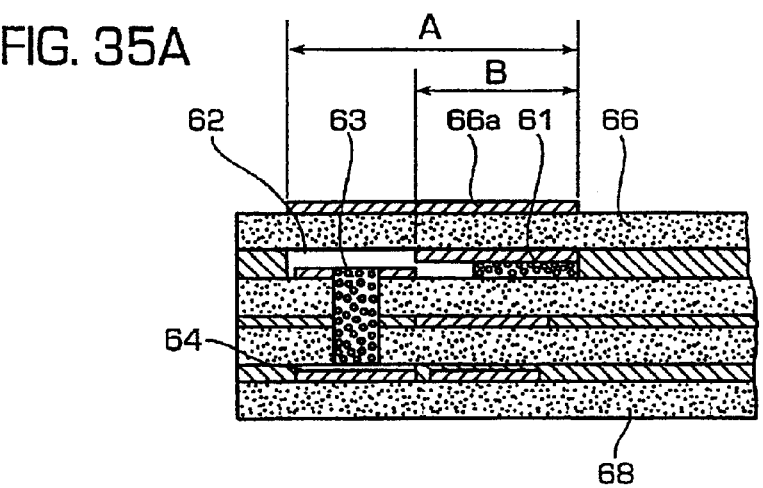
Figure 35B:
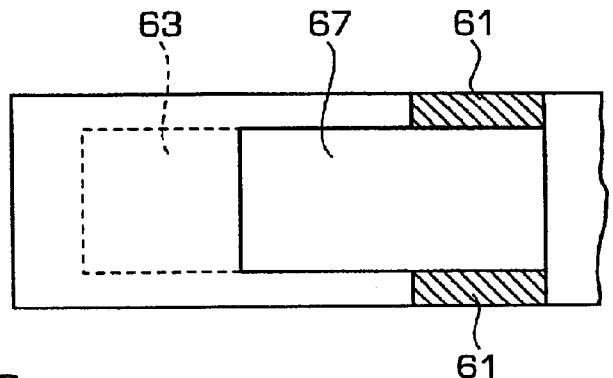
Figure 35C:
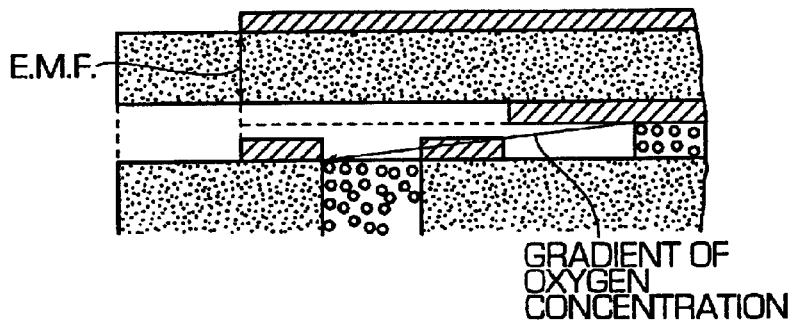
Figure 35D:
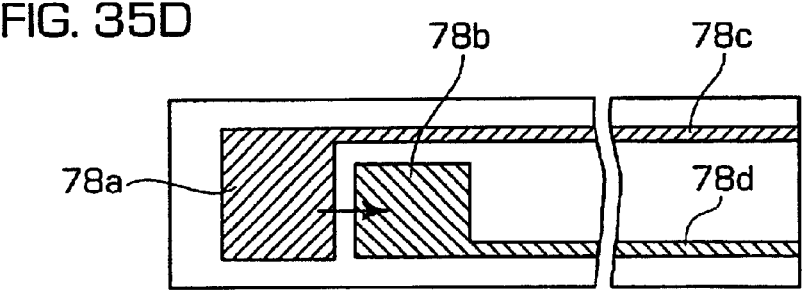

FIGS. 35A to 35D illustrate a NOx gas concentration sensor according to an embodiment of the present invention. FIG. 35A is a cross-sectional view taken along the longitudinal direction, FIG. 35B is a plan view of the first measurement chamber, FIG. 35C is a schematic enlarged cross-sectional view of the first measurement chamber and FIG. 35D is a plan view of the second measurement chamber. The sensor shown in FIGS. 35A to 35D includes a layer of a first oxygen ion pumping cell 66 having a solid electrolyte layer and electrodes 66a (positive electrode), 66b (negative electrode) provided on both sides of the solid electrolyte layer, a layer of an oxygen concentration measurement cell 67 having a solid electrolyte layer and oxygen partial pressure detecting electrodes provided on both sides of the solid electrolyte layer, a solid electrolyte layer, and a layer of the second oxygen ion pumping cell 68 having a solid electrolyte layer and oxygen ion pump electrodes 68a, 68b provided within and outside the second measurement chamber 64 formed on one sides of the solid electrolyte layer, layered in this order. The first measurement chamber 62 is defined by left and right insulating layers and upper and lower solid electrolyte layers, while the second measurement chamber 64 is defined above the layer of the second oxygen ion pumping cell 68. Two first diffusion holes 61, 61 are opened, apart from each other, to the first measurement chamber 62 for introducing the measurement gas via a diffusion resistance. The second diffusion hole 63 is passed through the layers of the oxygen concentration measurement cell 67 and the solid electrolyte layer for establishing communication between the first and second measurement chambers 62, 64 to supply a gas containing at least NOx and O2 from the first measurement chamber 62 via a diffusion resistance of a sensor diffusion hole 63 into the second measurement chamber 64.

Between the layers of the solid electrolyte are formed alumina insulating layers. Although not shown, heating layers for heating the entire sensor are bonded with a cement layer for sandwiching the entire sensor in the stacking direction. The electrodes are connected via leads formed between the layers to outside of the sensor, such as to a power source.

Referring to FIG. 35D, the electrodes 78a, 78b of the second oxygen ion pumping cell 68 are electrically connected to leads 78c, 78d.

One of the features of the present invention is that the first measurement chamber 62 and the second measurement chamber 64 are arranged in substantially superposed state and that the first diffusion holes 61, 61 are formed on both sides of the sensor, instead of on its distal end, with a porous material being charged into the second diffusion hole 63, an insulating film being arranged between the solid electrolyte layers and with the electrodes of the cells being insulated from one another. The second measurement chamber 64, defining a void, may be charged with a porous material.

Figure 36:
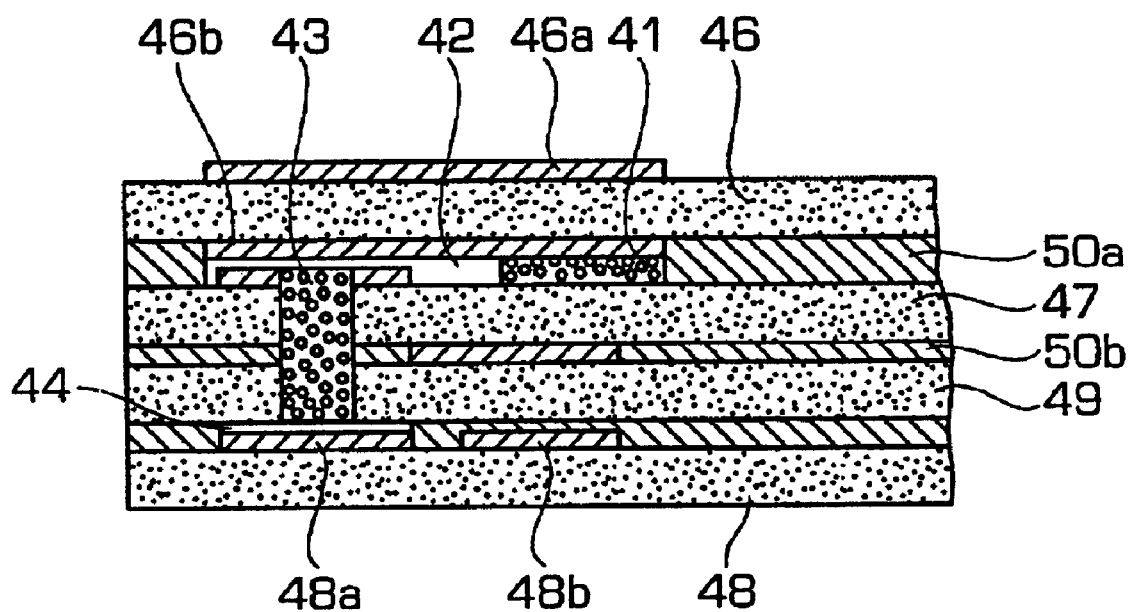
FIG. 36 illustrates a sensor of a reference example for the sensor shown in FIGS. 35A–35D.

As compared to the senor of FIG. 36, which is a comparative example with respect to the sensor of FIGS. 35A to 35D, the sensor of FIGS. 35A to 35D is characterized by that the lengths of the electrodes 66b in the first oxygen ion pump current 66 as measured in a direction along the flowing direction of the measurement gas flowing from the first diffusion hole 61 towards the second diffusion hole 63 is shorter than the longitudinal length of the first measurement chamber 62 (A>B). The inner electrode 66b is not formed to the position directly above the second diffusion hole 63.

By the electrode 66b of the first oxygen pumping cell 66, being shorter in length, the oxygen concentration gradient in the first measurement chamber 62 in particular in the measurement gas flow direction proceeding from a first diffusion aperture (portion) 61 towards a second diffusion aperture (portion) 63 is lowered. That is the oxygen concentration difference from one to the opposite end of the electrode 66b is reduced, while the electromotive force generated at the distal end portions of the electrode 66a, 66b is suppressed, as shown in FIG. 35C. Moreover, with suppression of the electro-motive force generated in the electrodes 66a, 66b, the first oxygen pumping cell voltage Vp1 is reduced for reducing the temperature dependency and oxygen concentration dependency in the NOx gas concentration measurement. This discloses an important design rule for making a most preferred sensor.

This effect is brought about by the fact that the first oxygen pumping cell voltage Vp1 required for pumping out excess oxygen is lowered so that there occurs no dissociation or decomposition of the NO gas other than that by oxygen pumping-out in the first measurement chamber. Specifically, the NO gas flowing into the second measurement chamber is not too decreased to prevent the Ip2 from being too lowered.

The NOx gas concentration was measured using the embodiment shown in FIGS. 35A to 35D and a sensor of the comparative example as shown in FIG. 36. The sensor of the embodiment was of a longitudinal length of 50 mm, a width (short side length of 4 mm and a thickness (in the stacking direction) was 1.3 mm. The first oxygen ion pump cell 66 was 0.3 mm in thickness while the electrodes 66a, 66b were of a longitudinal length A of 8 mm and a longitudinal length B of 4 mm and a short-side length of 2 mm. The first measurement chamber 62 was of a longitudinal length A of 7 mm, a short-side length of 2 mm and a height of 50 mm. The first diffusion hole 61 was of a longitudinal length of 50 m, while the second diffusion hole 63 was of a size of 1 mm and a distance from the end (right-hand end) of the first diffusion hole 61 equal to 5.5 mm. The sensor of the comparative example (FIG. 36) is of the same size as the sensor of the embodiment except that the longitudinal size of the electrodes 46a, 46b is 7 mm (A=B).

Generally, the NOx concentration in the gas is determined based on the following phenomenon: Namely, almost NO2 will be deemed to be dissociated into NO and 1/2O2 in a gas atmosphere of high temperature, e.g., at 800° C. under normal pressure in which a very small amount of NO2 in an amount of e.g., 0.1% (1000 ppm) is present together with other gases, thus which is deemed to be equivalent to the presence of 0.1% of NO.

The measurement is carried out basically under the following principle.

(1) At a high temperature (700° C. or above), the amount of NO2 contained as nNOx is dissociated into $nNO+n/2O_{1-x}$ and subjected to removal of the generated $n/2O_{1-x}$;

(2) nNO of step (1) is dissociated into $n/2 N_2+n/2O_2$.

This n/2 O2 is transmitted as oxygen ion through the oxygen ion conductor to measure a current caused by the oxygen ion transmission, through which a value proportionate to the current is obtained. Namely, by determining n of NO, the amount of NOx can be determined.

Ideally, the sensor should forward the NO generated at step (1) without subjecting to decomposition. However, a certain amount of dissociation of the generated NO at step (1) may occur oven under the best suited conditions dissociation rate between NO and (N+O) is governed by influences of various parameters, such as the applied voltage at step (1) and materials and design/configuration of the electrodes. Therefore, it is almost preferred to compensate for substantial decomposition of NO in the step (1). Typically, the composition can be performed by the inverse of the dissociation rate of NO into (N+O) (e.g., 60 to 95%).

Generally, the method for determining NOx concentration in a measurement gas is carried out as follows. The determination of the NOx concentration is carried out under a varying condition of the NOx gas concentration in the measurement gas in the course that the measurement gas is allowed to travel through a flow channel facing a ceramic body having electrically controllable conducting state of oxygen ions. The method comprises the following steps:

(1) introducing the measurement gas into the flow channel;

(2) forming in said flow channel a residual gas having a NOx concentration different from that before entrance into said flow channel by extracting an oxygen gas from the measurement gas of step (1) through the ceramic body to outside of the flow channel;

(3) dissociating NOx of said NOx-concentrated residual gas into nitrogen and oxygen by applying a voltage across electrodes formed on the ceramic body;

(4) measuring an electric current flowing through the ceramic body between the electrodes, said electric current being generated by the electrochemical action of the oxygen dissociated from NOx in step (3); and (5) determining a basic NOx concentration of the measurement gas, based on the electric current measured in step (4).

In step (1), the flow of the gas into the flow channel is restricted. Between steps (2) and (3), the flow of the residual gas to the electrode of the step (3) is restricted, too.

The flow channel may comprise a first flow channel and a second flow channel communicating with the first flow channel. The formation of the residual gas of step (2) is performed in the first flow channel, and wherein NOx in step (3) is dissociated in the second flow channel.

In step (2) the residual gas may be formed under the condition that allows and compensate for substantial decomposition of NOx in the flow channel.

In step (3) if the voltage is applied so as to dissociate $H_2O$ appropriate correction should be done. However, in step (3), the voltage may applied to an extent that does not substantially dissociate $H_2O$ in the residual gas.

Further modifications are possible generally as follows.

If a pre-set minor current, is allowed to flow in the oxygen concentration measurement cell, its electrode may be used as an auto-generating reference pole. The merit of this auto-generating reference pole is that the reference oxygen concentration is less susceptible to changes in oxygen concentration in air.

In the electrode structure, Au components may be carried by particles relatively coarser than the Au particles (that is zirconia particles as main electrode components) so that the Au components are dispersed finely. By adding a component carried by a catalyst adjustment method on the powders of an oxygen ion conductive solid electrolyte, in addition to the porous powders, such as Pt powders, the interface resistance generated across particles is lowered to improve the oxygen expelling capability. For example, one or more of Au, Ag, Ni Mn, Co, Cu, Ba, Mg, Ca, Na, K and Li may be selected and used as NOx dissociation suppressing capability, other than fine Au particles, as film, if so desired.

Various aspects of the present invention can be exploited under the general method for measuring the NOx concentration. Further modification of the various aspects and embodiments of the present invention can be made in view other technologies not disclosed herein as far as the basic concepts of the various aspects of the present invention are applicable. Particularly, combinations of any two or more aspects and/or embodiments are available within the entire disclosure of the present invention.

It should be noted modifications obvious in the art can be made without departing the gists and concepts as herein disclosed within the scope of the claims as appended.

What is claimed is:

1. A method for detecting the concentration of a specific gas in an engine exhaust gas with a gas sensor outputting a gas concentration detection signal, comprising:

estimating the amount of moisture in the exhaust gas from engine driving conditions;

estimating an air to fuel ratio supplied to said engine to correspond to the amount of moisture in said exhaust gas; and correcting the gas concentration detection signal output by the gas sensor based on the estimated air to fuel ratio.

2. The method as claimed in claim 1, wherein said correcting step comprises:

pre-formulating a map containing correction data for said gas concentration detection signal corresponding to said estimated ratio based on said estimated ratio, said gas concentration detection signal and true gas concentration value;

reading-out, from said map, specific correction data corresponding to said estimated ratio as determined by engine driving conditions; and correcting said gas concentration detection signal by the read-out correction data.

3. The method as claimed in claim 1, wherein said gas sensor is a NOx sensor.

4. A method for correcting a NOx concentration detection signal output from a NOx sensor, said NOx sensor having at least two solid electrolyte oxygen ion pump cells, in which a voltage is applied across a first oxygen ion pump cell for pumping out oxygen in the measurement gas, a current corresponding to the oxygen concentration in the measurement gas is caused to flow in said first oxygen ion pump cell, a second oxygen ion pump cell decomposes NOx in the gas not pumped by the first oxygen ion pump cell to pump out dissociated oxygen, with a current corresponding to the NOx gas concentration flowing in the second oxygen ion pump cell, said method comprising:

applying voltage across the first oxygen ion pump cell for sufficiently pumping out oxygen in the measurement gas to an extent not to allow all NOx to decompose in the measurement gas;

correcting a NOx concentration detection signal corresponding to the current flowing in the second oxygen ion pump cell based on current flowing in the first oxygen ion pump cell, to thereby remove or reduce the effect of the amount of moisture in the measurement gas from the NOx gas concentration as found based on said NOx gas concentration detection signal, said correcting step comprising:
estimating the current flowing in said first oxygen ion pump cell to correspond to the amount of the moisture in said measurement gas, pre-formulating a map containing correction data of said NOx gas concentration detection signal corresponding to current flowing in the first oxygen ion pump cell based on the current flowing in said first oxygen ion pump cell, reading out, from said map, pre-set correction data corresponding to current flowing in the first oxygen ion pump cell, and correcting the NOx gas concentration detection signal by the read-out correction data.

5. The method as claimed in claim 4, which comprises applying voltage across the first oxygen ion pump cell for sufficiently pumping out oxygen in the measurement gas to an extent substantially not to allow NOx in the measurement gas to decompose.

6. An apparatus for detecting the concentration of a specific gas in an engine exhaust gas, comprising:

a gas sensor for detecting the concentration of a specific gas in an engine exhaust gas and outputting a gas concentration signal;

means for estimating the amount of moisture in the exhaust gas from driving conditions of an engine;

means for estimating an air to fuel ratio supplied to said engine to correspond to the amount of moisture in said exhaust gas;

memory means for storing a map containing correction data for said gas concentration detection signal corresponding to said estimated air to fuel ratio based on said estimated ratio, said gas concentration detection signal and true gas concentration value;

reading means for reading out, from said map, specific correction data corresponding to said estimated ratio as determined by an engine driving condition; and correcting means for correcting said gas concentration detection signal by the read-out correction data.

7. The apparatus as claimed in claim 6, wherein said gas sensor is a NOx sensor.

8. A method for determining the NOx concentration in a measurement gas, under a varying condition of the NOx gas concentration in the measurement gas in the course that the measurement gas is allowed to travel through a flow channel facing a ceramic body having an electrically controllable conducting state of oxygen ions, comprising:

(1) introducing the measurement gas into the flow channel;

(2) forming in said flow channel a residual gas having a NOx concentration different from that before entrance into said flow channel by extracting an oxygen gas from the measurement gas of step (1) through the ceramic body to outside of the flow channel;

(3) dissociating NOx of said NOx-concentrated residual gas into nitrogen and oxygen by applying a voltage across electrodes formed on the ceramic body;

(4) measuring an electric current flowing through the ceramic body between the electrodes, said electric current being generated by the electrochemical action of the oxygen dissociated from NOx in step (3);

(5) determining a basic NOx concentration of the measurement gas, based on the electric current measured in step (4); and (6) correcting the basic NOx concentration wherein the amount of moisture in said measurement gas is estimated from a driving condition of an engine, and said NOx concentration of step (5) is corrected depending on an estimated amount of moisture.

* * * * *